US009937227B2

(12) United States Patent
Swerdloff et al.

(10) Patent No.: US 9,937,227 B2
(45) Date of Patent: Apr. 10, 2018

(54) HUMANIN, ANALOGS AND CANCER TREATMENT METHODS AND USES THEREOF

(71) Applicant: LOS ANGELES BIOMEDICAL RESEARCH INSTITUTE AT HARBOR-UCLA MEDICAL CENTER, Torrance, CA (US)

(72) Inventors: Ronald S. Swerdloff, Long Beach, CA (US); YanHe Lue, Torrance, CA (US); Christina Wang, Long Beach, CA (US)

(73) Assignee: LOS ANGELES BIOMEDICAL RESEARCH INSTITUTE AT HARBOR-UCLA MEDICAL CENTER, Torrance, CA (US)

(*) Notice: Subject to any disclaimer, the term of this patent is extended or adjusted under 35 U.S.C. 154(b) by 0 days.

(21) Appl. No.: 14/645,308

(22) Filed: Mar. 11, 2015

(65) Prior Publication Data
US 2016/0082080 A1 Mar. 24, 2016

Related U.S. Application Data

(60) Provisional application No. 61/951,198, filed on Mar. 11, 2014, provisional application No. 61/951,174, filed on Mar. 11, 2014.

(51) Int. Cl.
A61K 38/17 (2006.01)
C07K 14/47 (2006.01)
A61K 38/13 (2006.01)
A61K 45/06 (2006.01)
A61K 31/4188 (2006.01)
A61K 31/675 (2006.01)
A61K 31/495 (2006.01)
A61K 31/704 (2006.01)

(52) U.S. Cl.
CPC ...... A61K 38/1709 (2013.01); A61K 31/4188 (2013.01); A61K 31/495 (2013.01); A61K 31/675 (2013.01); A61K 31/704 (2013.01); A61K 38/13 (2013.01); A61K 38/17 (2013.01); A61K 45/06 (2013.01); C07K 14/47 (2013.01)

(58) Field of Classification Search
None
See application file for complete search history.

(56) References Cited

U.S. PATENT DOCUMENTS

2013/0053323 A1   2/2013  Ericksson et al. ........... 514/16.9

FOREIGN PATENT DOCUMENTS

WO   2011/076880   6/2011

OTHER PUBLICATIONS

Jia et al., Humanin is detected in the testis after intraperitoneal (ip) administration. Endocrine Reviews, vol. 33, No. 3, Supp. Jun. 2012, SAT-76.*
Arakawa T, Kita Y, Niikura T. (2008) A rescue factor for Alzheimer's diseases: discovery, activity, structure, and mechanism. Curr Med Chem 15(21): 2086-2098.
Arakawa T1, Niikura T, Kita Y. (2011) The biological activity of Humanin analogs correlates with structure stabilities in solution. Int J Biol Macromol 49(1): 93-97. doi: 10.1016/j.ijbiomac.2011.04.003.
Bachar A R, Scheffer L, Schroeder A S, Nakamura H K, Cobb L J, Oh Y K, Lerman L O, Pagano R E, Cohen P & Lerman A. (2010) *Humanin is expressed in human vascular walls and has a cytoprotective effect against oxidized LDL-induced oxidative stress.* Cardiovasc. Res. 88, 360-366.
Bar-Joseph H, Ben-Aharon I, Rizel S, Stemmer SM, Tzabari M, Shalgi R. Doxorubicin-induced apoptosis in germinal vesicle (GV) oocytes. Reprod Toxicol. 2010;30(4):566-72.
Ben-Aharon I, Bar-Joseph H, Tzarfaty G, Kuchinsky L, Rizel S, Stemmer SM, Shalgi R. Doxorubicin-induced ovarian toxicity. Reprod Biol Endocrinol. 2010;8:20. PMCID: Pmc2838903.
Biglia N, Peano E, Sgandurra P, Moggio G, Pecchio S, Maggiorotto F, Sismondi P. Body mass index (BMI) and breast cancer: impact on tumor histopathologic features, cancer subtypes and recurrence rate in pre and postmenopausal women. Gynecol Endocrinol. 2013;29(3):263-7.
Boekelheide K, Schoenfeld H A, Hall S J, Weng C C, Shetty G, Leith J, Harper J, Sigman M, Hess D L & Meistrich M L. (2005) Gonadotropin-releasing hormone antagonist (Cetrorelix) therapy fails to protect nonhuman primates (*Macaca arctoides*) from radiation-induced spermatogenic failure. J. Androl. 26, 222-234.
Bristol-Gould SK, Kreeger PK, Selkirk CG, Kilen SM, Mayo KE, Shea LD, Woodruff TK. Fate of the initial follicle pool: empirical and mathematical evidence supporting its sufficiency for adult fertility. Dev Biol. 2006;298(1)149-54.
Cai L, Hales BFf, Robaire B. (1997) Induction of apoptosis in the germ cells of adult male rats after exposure to cyclophosphamide. Biol Reprod 56(6): 1490-1497.
Chlebowski RT, Blackburn GL, Buzzard IM, Rose DP, Martino S, Khandekar JD, York RM, Jeffery RW, Elashoff RM, Wynder EL. Adherence to a dietary fat intake reduction program in postmenopausal women receiving therapy for early breast cancer. The Women's Intervention Nutrition Study. J Clin Oncol. 1993;11(11):2072-80.
Choy J T & Brannigan R E. (2013) *The determination of reproductive safety in men during and after cancer treatment.* Fertil. Steril. 100, 1187-1191.
Collisson E A, De A, Suzuki H, Gambhir S S & Kolodney M S. (2003) *Treatment of metastatic melanoma with an orally available inhibitor of the Ras-Raf-MAPK cascade.* Cancer Res. 63, 5669-5673.
Colon E, Strand M L, Carlsson-Skwirut C, Wahlgren A, Svechnikov K V, Cohen P & Soder O. (2006) *Anti-apoptotic factor humanin is expressed in the testis and prevents cell-death in leydig cells during the first wave of spermatogenesis.* J. Cell. Physiol. 208, 373-385.
Craft N, Bruhn K W, Nguyen B D, Prins R, Liau L M, Collisson E A, De A, Kolodney M S, Gambhir S S & Miller J F. (2005) *Bioluminescent imaging of melanoma in live mice.* J. Invest. Dermatol. 125, 159-165.
Delbes G, Vaisheva F, Luu T, Marcon L, Hales B F & Robaire B. (2010) *Reversibility of the effects of the chemotherapeutic regimen for non-Hodgkin lymphoma, cyclophosphamide, doxorubicin, vincristine, and prednisone, on the male rat reproductive system and progeny outcome.* Reprod. Toxicol. 29, 332-338.

(Continued)

Primary Examiner — Elly-Gerald Stoica
(74) Attorney, Agent, or Firm — Pillsbury Winthrop Shaw Pittman LLP

(57) ABSTRACT

Described herein are methods of enhancing chemotherapeutic treatment of a hyperproliferative disorder by, in part, administering a composition comprising one or more humanin polypeptides to a subject receiving chemotherapy.

18 Claims, 30 Drawing Sheets

(56) References Cited

OTHER PUBLICATIONS

Desai VG, Herman EH, Moland CL, Branham WS, Lewis SM, Davis KJ, George NI, Lee T, Kerr S, Fuscoe JC. Development of doxorubicin-induced chronic cardiotoxicity in the B6C3F1 mouse model. Toxicol Appl Pharmacol. 2013;266(1):109-21.
Dohle G R. (2010) *Male infertility in cancer patients: Review of the literature*. Int. J. Urol. 17, 327-331.
Doroshow JH. Anthracycline antibiotic-stimulated superoxide, hydrogen peroxide, and hydroxyl radical production by NADH dehydrogenase. Cancer Res. 1983;43(10):4543-51.
Drumond A L, Weng C C, Wang G, Chiarini-Garcia H, Eras-Garcia L & Meistrich M L. (2011) *Effects of multiple doses of cyclophosphamide on mouse testes: accessing the germ cells lost, and the functional damage of stem cells*. Reprod. Toxicol. 32, 395-406.
Erkkila K, Henriksen K, Hirvonen V, Rannikko S, Salo J, Parvinen M & Dunkel L. (1997) *Testosterone regulates apoptosis in adult human seminiferous tubules in vitro*. J. Clin. Endocrinol. Metab. 82, 2314-2321.
Garrisi VM, Tufaro A, Trerotoli P, Bongarzone I, Quaranta M, Ventrella V, Tommasi S, Giannelli G, Paradiso A. Body mass index and serum proteomic profile in breast cancer and healthy women: a prospective study. PLoS One. 2012;7(11):e49631. PMCID: Pmc3511468.
Goel S, Gupta N, Walcott BP, Snuderl M, Kesler CT, Kirkpatrick ND, Heishi T, Huang Y, Martin JD, Ager E, Samuel R, Wang S, Yazbek J, Vakoc BJ, Peterson RT, Padera TP, Duda DG, Fukumura D, Jain RK. Effects of vascular-endothelial protein tyrosine phosphatase inhibition on breast cancer vasculature and metastatic progression. J Natl Cancer Inst. 2013;105(16):1188-201. PMCID: Pmc3748004.
Gor PP, Su HI, Gray RJ, Gimotty PA, Horn M, Aplenc R, Vaughan WP, Tallman MS, Rebbeck TR, DeMichele A. (2010) Cyclophosphamide-metabolizing enzyme polymorphisms and survival outcomes after adjuvant chemotherapy for node-positive breast cancer: a retrospective cohort study. Breast cancer research 12: R26.
Guo B, Zhai D, Cabezas E, Welsh K, Nouraini S, Satterthwait AC, Reed JC. (2003) Humanin peptide suppresses apoptosis by interfering with Bax activation. Nature 423: 456-461.
Hartmann T B, Mattern E, Wiedemann N, van Doorn R, Willemze R, Niikura T, Hildenbrand R, Schadendorf D & Eichmuller S B. (2008) *Identification of selectively expressed genes and antigens in CTCL*. Exp. Dermatol. 17, 324-334.
Hashimoto Y, Kurita M, Aiso S, Nishimoto I, Matsuoka M. (2009) Humanin inhibits neuronal cell death by interacting with a cytokine receptor complex or complexes involving CNTF receptor α/WSX-1/gp130. Mol Biol Cell 20: 2864-2873.
Hashimoto Y, Niikura T, Ito Y, Sudo H, Hata M, Arakawa E, Abe Y, Kita Y & Nishimoto I. (2001) *Detailed characterization of neuroprotection by a rescue factor humanin against various Alzheimer's disease-relevant insults*. J. Neurosci. 21, 9235-9245.
Hashimoto Y, Niikura T, Tajima H, Yasukawa T, Sudo H, Ito Y, Kita Y, Kawasumi M, Kouyama K, Doyu M, Sobue G, Koide T, Tsuji S, Lang J, Kurokawa K & Nishimoto I. (2001) *A rescue factor abolishing neuronal cell death by a wide spectrum of familial Alzheimer's disease genes and Abeta*. Proc. Natl. Acad. Sci. U. S. A. 98, 6336-6341.
Hashimoto Y, Suzuki H, Aiso S, Niikura T, Nishimoto I, Matsuoka M. (2005) Involvement of tyrosine kinases and STAT3 in Humanin-mediated neuroprotection. Life Sci 77: 3092-3104.
Hashimoto Y, Terashita K, Niikura T, Yamagishi Y, Ishizaka M, Kanekura K, Chiba T, Yamada M, Kita Y, Aiso S, Matsuoka M & Nishimoto I. (2004) Humanin antagonists: mutants that interfere with dimerization inhibit neuroprotection by Humanin. Eur J Neurosci 19, 2356-2364.
Hoang P T, Park P, Cobb L J, Paharkova-Vatchkova V, Hakimi M, Cohen P & Lee K W. (2010) *The neurosurvival factor Humanin inhibits beta-cell apoptosis via signal transducer and activator of transcription 3 activation and delays and ameliorates diabetes in nonobese diabetic mice*. Metabolism. 59, 343-349.
Ikonen M, Liu B, Hashimoto Y, Ma L, Lee KW, Niikura T, Nishimoto I, and Cohen P. (2003) Interaction between the Alzheimer's survival peptide Humanin and insulin-like growth factor-binding protein 3 regulates cell survival and apoptosis. Proc Natl Acad Sci USA 100: 13042-13047.
Jia Y, Castellanos J, Wang C, Sinha-Hikim I, Lue Y, Swerdloff RS, Sinha-Hikim AP. (2009) Mitogen-Activated Protein Kinase Signaling in Male Germ Cell Apoptosis in the Rat: Biol.Reprod 80: 771-780.
Jia Y, Lee KW, Swerdloff R, Hwang D, Cobb LJ, Sinha Hikim A, Lue YH, Cohen P, and Wang C. (2010) Interaction of insulin-like growth factor-binding protein-3 and BAX in mitochondria promotes male germ cell apoptosis. J Biol Chem 285: 1726-1732.
Jia Y, Lue Y H, Swerdloff R, Lee K W, Cobb L J, Cohen P & Wang C. (2013) The cytoprotective peptide humanin is induced and neutralizes Bax after pro-apoptotic stress in the rat testis. Andrology 1, 651-659.
Jia Y, Sinha Hikim AP, Swerdloff RS, Lue YH, Vera Y, Zhang XS, Hu ZY, Li YC, Liu YX, Wang C. (2007) Signaling pathways for germ cell death in adult Cynomolgus monkeys (*Macaca fascicularis*) induced by mild testicular hyperthermia and exogenous testosterone treatment. Biol Reprod 77: 83-92.
Jimenez M, Spaliviero JA, Grootenhuis AJ, Verhagen J, Allan CM, Handelsman DJ. Validation of an ultrasensitive and specific immunofluorometric assay for mouse follicle-stimulating hormone. Biol Reprod. 2005;72(1):78-85.
Kamineni A, Anderson ML, White E, Taplin SH, Porter P, Ballard-Barbash R, Malone K, Buist DS. Body mass index, tumor characteristics, and prognosis following diagnosis of early-stage breast cancer in a mammographically screened population. Cancer Causes Control. 2013;24(2):305-12. PMCID: Pmc3557530.
Kim SY, Cordeiro MH, Serna VA, Ebbert K, Butler LM, Sinha S, Mills AA, Woodruff TK, Kurita T. Rescue of platinum-damaged oocytes from programmed cell death through inactivation of the p53 family signaling network. Cell Death Differ. 2013;20(8):987-97. PMCID: Pmc3705595.
Kuliawat R1, Klein L, Gong Z, Nicoletta-Gentile M, Nemkal A, Cui L, Bastie C, Su K, Huffman D, Surana M, Barzilai N, Fleischer N, Muzumdar R. (2013) Potent humanin analog increases glucose-stimulated insulin secretion through enhanced metabolism in the β cell. FASEB J 27(12): 4890-4898. doi: 10.1096/fj.13-231092. Epub Aug. 30, 2013.
Kunesová G, Hlavácek J, Patocka J, Evangelou A, Zikos C, Benaki D, Paravatou-Petsotas M, Pelecanou M, Livaniou E, Slaninova J. (2008) The multiple T-maze in vivo testing of the neuroprotective effect of humanin analogs. Peptides 29: 1982-1987.
Loren A W, Mangu P B, Beck L N, Brennan L, Magdalinski A J, Partridge A H, Quinn G, Wallace W H & Oktay K. (2013) *Fertility preservation for patients with cancer: American Society of Clinical Oncology clinical practice guideline update*. J. Clin. Oncol. 31, 2500-2510.
Lue Y H, Sinha Hikim AP, Swerdloff RA, Im P, Taing KS, Bui T, Leung A, Wang C. (1999) Single exposure to heat induces stage-specific germ cell apoptosis in rats: role of intratesticular testosterone (T) on stage specificity. Endocrinology 140: 1709-1717.
Lue Y, Swerdloff R, Liu Q, Mehta H, Hikim A S, Lee K W, Jia Y, Hwang D, Cobb L J, Cohen P & Wang C. (2010) *Opposing roles of insulin-like growth factor binding protein 3 and humanin in the regulation of testicular germ cell apoptosis*. Endocrinology 151, 350-357.
Lue Y, Wang C, Cui Y, Wang X, Sha J, Zhou Z, Xu J, Hikim A P & Swerdloff R S. (2009) *Levonorgestrel enhances spermatogenesis suppression by testosterone with greater alteration in testicular gene expression in men*. Biol. Reprod. 80, 484-492.
Lue Y, Wang C, Liu YX, Hikim AP, Zhang XS, Ng CM, Hu ZY, Li YC, Leung A, and Swerdloff RS. (2006) Transient testicular warming enhances the suppressive effect of testosterone on spermatogenesis in adult cynomolgus monkeys (*Macaca fascicularis*). J Clin Endocrinol Metab 91: 539-545.
Marcon L, Hales BF, Robaire B. (2008) Reversibility of the effects of subchronic exposure to the cancer chemotherapeutics bleomycin,

(56) References Cited

OTHER PUBLICATIONS etoposide, and cisplatin on spermatogenesis, fertility, and progeny outcome in the male rat. J Andrology 29: 4.
Marcon L, Zhang X, Hales B F, Robaire B & Nagano M C. (2011) *Effects of Chemotherapeutic Agents for Testicular Cancer on Rat Spermatogonial Stem/Progenitor Cells.* J. Androl.
Matsuoka M, Hashimoto Y. (2010) Humanin and the receptors for humanin. Mol Neurobiol 41: 22-28.
Maximov V, Martynenko A, Hunsmann G & Tarantul V. (2002) *Mitochondrial 16S rRNA gene encodes a functional peptide, a potential drug for Alzheimer's disease and target for cancer therapy.* Med. Hypotheses 59, 670-673.
Mayle A, Luo M, Jeong M, Goodell MA. Flow cytometry analysis of murine hematopoietic stem cells. Cytometry Part A : the journal of the International Society for Analytical Cytology. 2013;83(1):27-37. PMCID: Pmc3638885.
Meistrich M L, Finch M, da Cunha M F, Hacker U & Au W W. (1982) *Damaging effects of fourteen chemotherapeutic drugs on mouse testis cells.* Cancer Res. 42, 122-131.
Meistrich M L. (2013) *Effects of chemotherapy and radiotherapy on spermatogenesis in humans.* Fertil. Steril. 100, 1180-1186.
Meistrich ML. (2009) Male gonadal toxicity. Pediatr Blood Cancer 53:261-266.
Miao J, Zhang W, Yin R, Liu R, Su C, Lei G, Li Z. (2008) S14G HN ameliorates Abeta25-35-induced behavioral deficits by reducing neuroinflammatory responses and apoptosis in mice. Neuropeptides 42:557-567.
Moretti E, Giannerini V, Rossini L, Matsuoka M, Trabalzini L & Collodel G. (2010) *Immunolocalization of humanin in human sperm and testis.* Fertil. Steril. 94, 2888-2890.
Mottaghi-Dastjerdi N, Soltany-Rezaee-Rad M, Sepehrizadeh Z, Roshandel G, Ebrahimifard F & Setayesh N. (2014) *Genome expression analysis by suppression subtractive hybridization identified overexpression of Humanin, a target gene in gastric cancer chemoresistance.* Daru : journal of Faculty of Pharmacy, Tehran University of Medical Sciences 22, 14.
Muzumdar R H, Huffman D M, Calvert J W, Jha S, Weinberg Y, Cui L, Nemkal A, Atzmon G, Klein L, Gundewar S, Ji S Y, Lavu M, Predmore B L & Lefer D J. (2010) *Acute humanin therapy attenuates myocardial ischemia and reperfusion injury in mice.* Arterioscler. Thromb. Vac. Biol. 30, 1940-1948.
Nangia A K, Krieg S A & Kim S S. (2013) *Clinical guidelines for sperm cryopreservation in cancer patients.* Fertil. Steril. 100, 1203-1209.
Niikura et al. A humanin derivative reduces amyloid beta accumulation and ameliorates memory deficit in triple transgenic mice. PLoS One. 2011;6(1):e16259. PMCID: 3022031.
O'Brien PJ, Dameron GW, Beck ML, Kang YJ, Erickson BK, Di Battista TH, Miller KE, Jackson KN, Mittelstadt S. Cardiac troponin T is a sensitive, specific biomarker of cardiac injury in laboratory animals. Lab Anim Sci. 1997;47(5):486-95.
Ottewell PD, Monkkonen H, Jones M, Lefley DV, Coleman RE, Holen I. Antitumor effects of doxorubicin followed by zoledronic acid in a mouse model of breast cancer. J Natl Cancer Inst. 2008;100(16):1167-78.
Panosyan EH, Wang Y, Xia P, Lee WN, Pak Y, Laks DR, Lin HJ, Moore TB, Cloughesy TF, Kornblum HI, Lasky JL, 3rd. Asparagine depletion potentiates the cytotoxic effect of chemotherapy against brain tumors. Molecular cancer research : MCR. 2014;12(5):694-702. PMCID: Pmc4020976.
Perez GI, Knudson CM, Leykin L, Korsmeyer SJ, Tilly JL. Apoptosis-associated signaling pathways are required for chemotherapy-mediated female germ cell destruction. Nat Med. 1997;3(11):1228-32.
Prentice RL, Caan B, Chlebowski RT, Patterson R, Kuller LH, Ockene JK, Margolis KL, Limacher MC, Manson JE, Parker LM, Paskett E, Phillips L, Robbins J, Rossouw JE, Sarto GE, Shikany JM, Stefanick ML, Thomson CA, Van Horn L, Vitolins MZ, Wactawski-Wende J, Wallace RB, Wassertheil-Smoller S, Whitlock E, Yano K, Adams-Campbell L, Anderson GL, Assaf AR, Beresford SA, Black HR, Brunner RL, Brzyski RG, Ford L, Gass M, Hays J, Heber D, Heiss G, Hendrix SL, Hsia J, Hubbell FA, Jackson RD, Johnson KC, Kotchen JM, LaCroix AZ, Lane DS, Langer RD, Lasser NL, Henderson MM. Low-fat dietary pattern and risk of invasive breast cancer: the Women's Health Initiative Randomized Controlled Dietary Modification Trial. JAMA. 2006;295(6):629-42.
Roti Roti EC, Leisman SK, Abbott DH, Salih SM. Acute doxorubicin insult in the mouse ovary is cell- and follicle-type dependent. PLoS One. 2012;7(8):e42293. PMCID: Pmc3410926.
Rundberg Nilsson A, Bryder D, Pronk CJ. Frequency determination of rare populations by flow cytometry: a hematopoietic stem cell perspective. Cytometry Part A : The journal of the International Society for Analytical Cytology. 2013;83(8):721-7.
Russell L. (1977) Movement of spermatocytes from the basal to the adluminal compartment of the rat testes. Am J Anat 148: 313-328.
Schlueter AJ, Bhatia SK, Li X, Tygrett LT, Yamashita Y, de Vries P, Waldschmidt TJ. Delineation among eight major hematopoietic subsets in murine bone marrow using a two-color flow cytometric technique. Cytometry. 2001;43(4):297-307.
Serradj N, Jamon M. Age-related changes in the motricity of the inbred mice strains 129/sv and C57BL/6j. Behav Brain Res. 2007;177(1):80-9.
Simpson ER, Brown KA. Obesity and breast cancer: role of inflammation and aromatase. J Mol Endocrinol. 2013;51(3):T51-9.
Sinha Hikim AP, Rajavashisth TB, Sinha Hikim I, Lue Y, Bonavera JJ, Leung A, Wang C, Swerdloff RS. (1997) Significance of apoptosis in the temporal and stage-specific loss of germ cells in the adult rat after gonadotropin deprivation. Biol Reprod 57: 1193-1201.
Sloderbach A, Gorska A, Sikorska M, Misiura K & Hladon B. (2013) *Classical oxazaphosphorines—metabolism and therapeutic properties—new implications.* Postepy higieny i medycyny doswiadczalnej (Online) 67, 1235-1253.
Sponne I, Fifre A, Koziel V, Kriem B, Oster T, Pillot T. (2004) Humanin rescues cortical neurons from prion-peptide-induced apoptosis. Mol Cell Neurosci 25(1): 95-102.
Sprando R L, Santulli R, Awoniyi C A, Ewing L L & Zirkin B R. (1990) Does ethane 1,2-dimethanesulphonate (EDS) have a direct cytotoxic effect on the seminiferous epithelium of the rat testis? J. Androl. 11, 344-352.
Sun X, Zhou Z, Kang YJ. Attenuation of doxorubicin chronic toxicity in metallothionein-overexpressing transgenic mouse heart. Cancer Res. 2001;61(8):3382-7.
Tarantul V Z & Hunsmann G. (2001) *Mitochondrial polypeptides of the oxidative phosphorylation pathway as potential new targets for anti-cancer therapy.* Med. Hypotheses 56, 386-387.
Toppari J & Parvinen M. (1985) *In vitro differentiation of rat seminiferous tubular segments from defined stages of the epithelial cycle morphologic and immunolocalization analysis.* J. Androl. 6, 334-343.
Trost L W & Brannigan R E. (2012) *Oncofertility and the male cancer patient.* Current treatment options in oncology 13, 146-160.
Watring WG, Byfield JE, Lagasse LD, Lee YD, Juillard G, Jacobs M, Smith ML. (1974) Combination Adriamycin and radiation therapy in gynecologic cancers. Gynecol Oncol 2(4):518-526.
Yamada M, Chiba T, Sasabe J, Terashita K, Aiso S, Matsuoka M. (2008) Nasal colivelin treatment ameliorates memory impairment related to Alzheimer's disease. Neuropsychopharmaco 33: 2020-2032.
Yamagishi Y, Hashimoto Y, Niikura T, Nishimoto I. (2003) Identification of essential amino acids in Humanin, a neuroprotective factor against Alzheimer's disease-relevant insults. Peptides 24(4): 585-595.
Yen K, Lee C, Mehta H, Cohen P. (2013) The emerging role of the mitochondrial-derived peptide humanin in stress resistance. J Mol Endocrinol 50(1): R11-19. doi: 10.1530/JME-12-0203. Print Feb. 2013.
Zhai D, Luciano F, Zhu X, Guo B, Satterthwait AC, Reed JC. (2005) Humanin binds and nullifies Bid activity by blocking its activation of Bax and Bak. J Biol Chem 280: 15815-15824.
Aikoui, O. et al., Humanin Reduces Cyclophosphamide Induced Male Germ Cell Apoptosis in Mice, published on: Oct. 12, 2012;URL: http://sacnas.confex.com/sacnas/2012/webprogram/Paper7181.html Oct. 12, 2012 (Oct. 12, 2012).

(56) References Cited

OTHER PUBLICATIONS

Ohanyan, A., Humanin significantly reduces cyclophosphamide and doxorubicin induced germ cell apoptosis in-vivo and ex-vivo mice, published online: Jan. 22, 2014. URL: http://gradworks.umi.com/15/23/1523474.html Jan. 22, 2014 (Jan. 22, 2014)).

Jia, Yue, et al. "The cytoprotective peptide humanin is induced and neutralizes Bax after proapoptotic stress in the rat testis." Andrology 1.4 (May 20, 2013): 651-659. URL: http://onlinelibrary.wiley.com/doi/10.1111/j.2047-2927.2013.00091.k/full; cited in the document May 20, 2013 (May 20, 2013).

Eriksson, E., et al., Protective role of humanin on bortezomib-induced bone growth impairment in anticancer treatment, Journal of the National Cancer Institute 106.3 (Mar. 1, 2014): djt459. URL: http://jnci.oxfordjournals.org/content/106/3/djt459.full.html Mar. 1, 2014 (Mar. 1, 2014)).

Cohen, P., New Role for the Mitochondrial Peptide Humanin: Protective Agent Against Chemotherapy-Induced Side Effects, Journal of the National Cancer Institute (Mar. 1, 2014): dju006. URL: http://jnci.oxfordjournals.org/content//early/2014/02/28jnci.dju006.full Mar. 1, 2014 (Mar. 1, 2014).

\* cited by examiner

Fig. 4  Early and Late Stages of the Seminiferous Epithelium in Response to CP, HN and CP+HN
Fig. 4 A-D
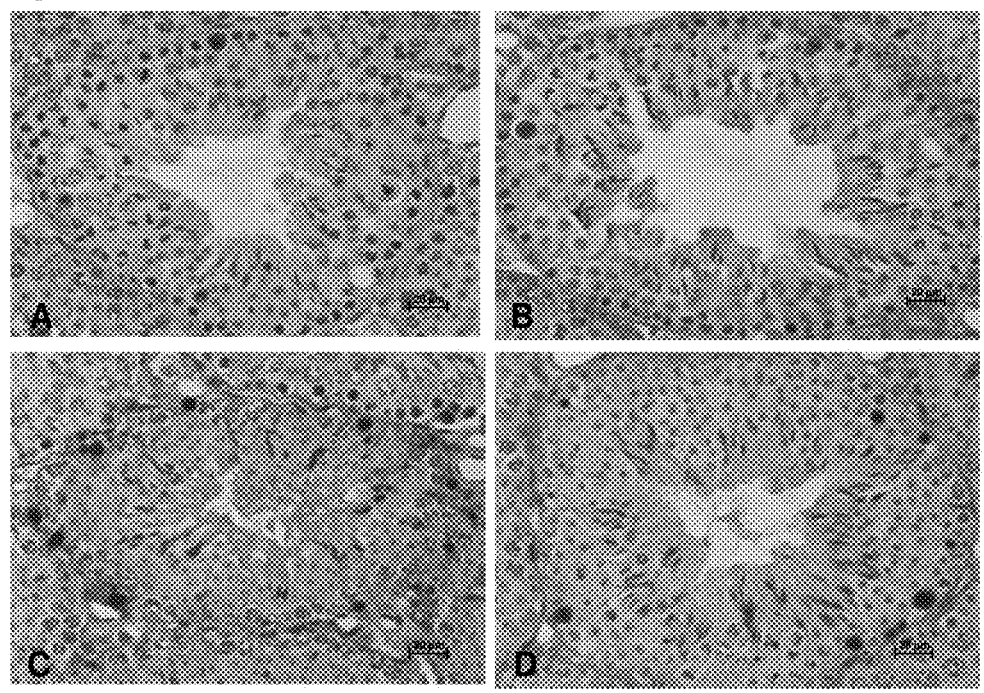
Fig. 4E
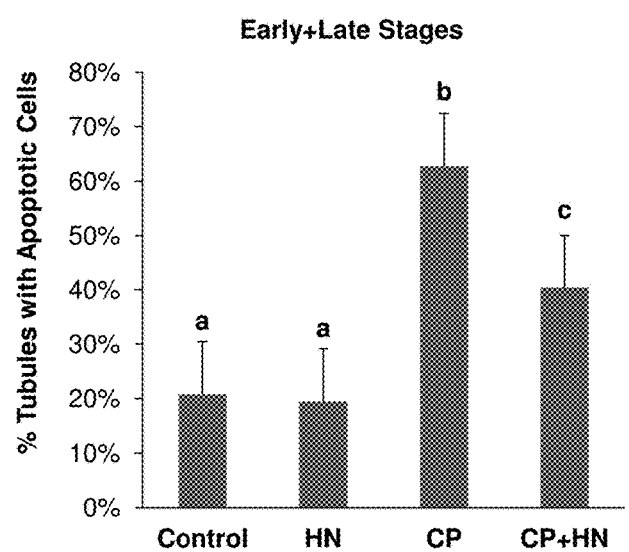

Fig. 5 Middle Stages of the Seminiferous Epithelium in Response to CP, HN and CP+HN
Fig. 5 A-D
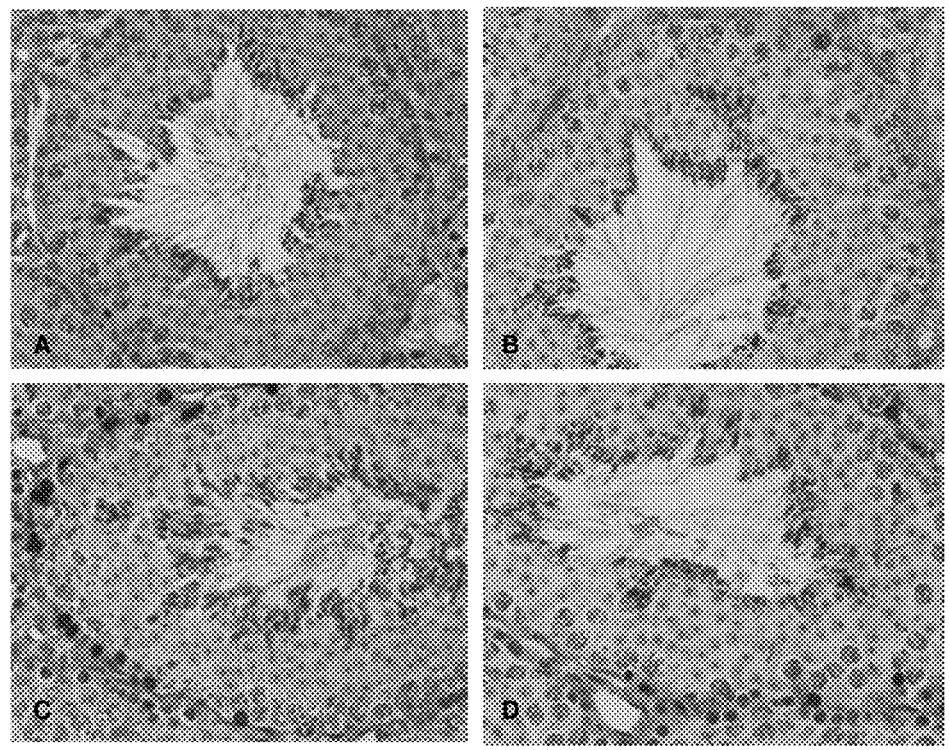
Fig. 5E
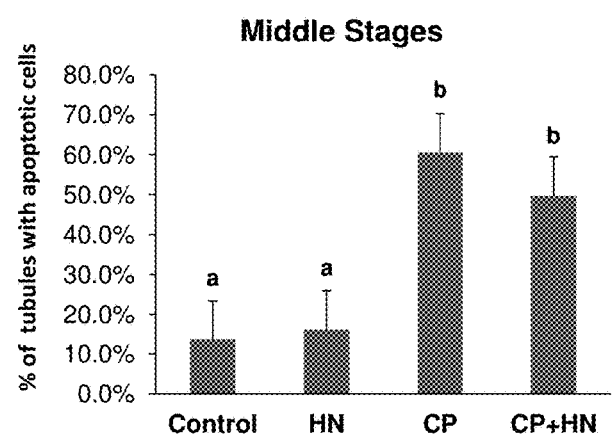

Body Weight Before and After B16 Cell Tail Vein Injection in Mice

Number of Lung Metastatic Tumors After 3 wks of B16 Cell Injection, and 2 wks After HNG, CP or CP+HNG Treatment in Mice HNG5: 5mg/kg BW
HNG15: 15mg/kg BW N=5 mice
N=6 mice in CPHNG5 group CP (100mg/kg BW, ip single injection); HNG (5mg/kg BW, daily for 2 wks), n=6

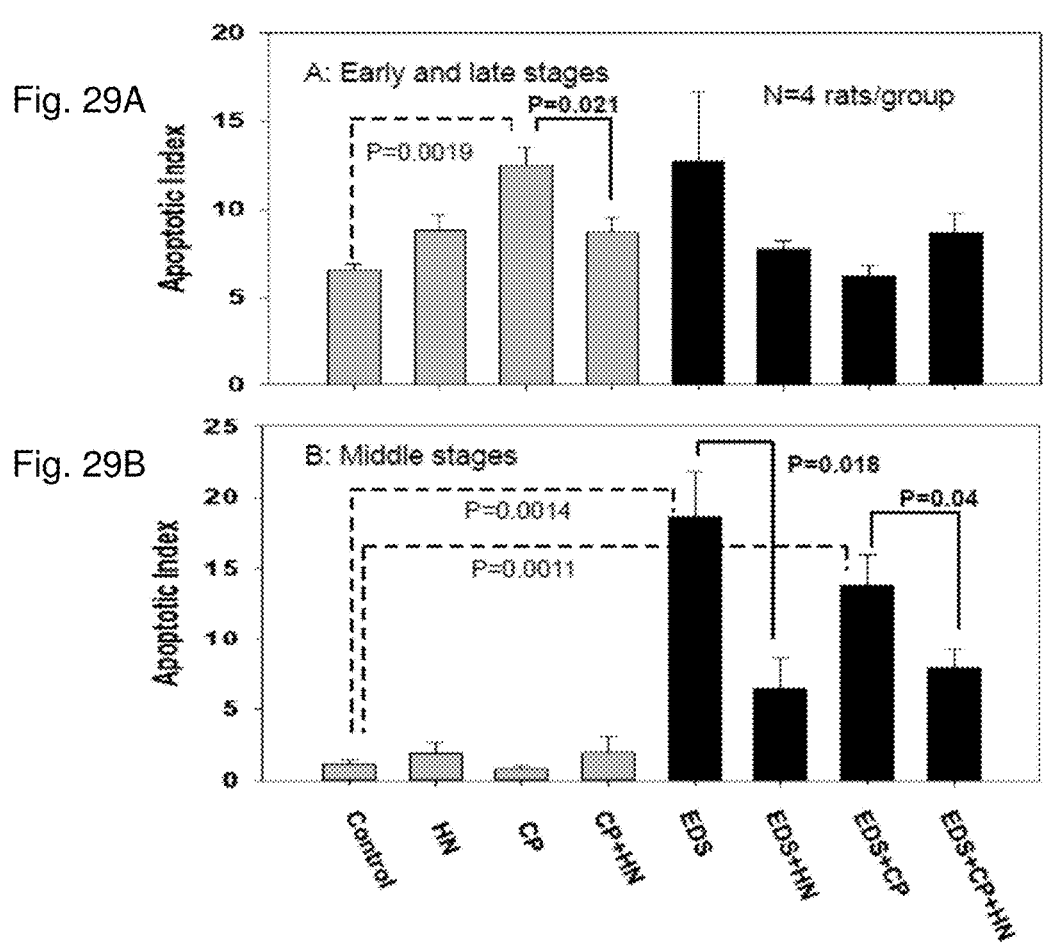

HUMANIN, ANALOGS AND CANCER TREATMENT METHODS AND USES THEREOF

RELATED PATENT APPLICATIONS

This patent application claims the benefit of U.S. Provisional Patent Application No. 61/951,198 filed on Mar. 11, 2014, and U.S. Provisional Patent Application No. 61/951,174 filed on Mar. 11, 2014, each of which applications are incorporated herein by reference in their entirety.

SEQUENCE LISTING

The instant application contains a Sequence Listing which has been submitted electronically in ASCII format and is hereby incorporated by reference in its entirety. Said ASCII copy, created Jun. 8, 2015, is named LaBioMed0437687.ST25txt and is 25,012 bytes in size.

FIELD

The technology relates in part to compositions that comprise humanin and/or humanin analogs and uses thereof.

INTRODUCTION

Chemotherapy is a relatively effective drug treatment designed to kill cancer cells in individuals with various forms of cancer. However, the administration of a chemotherapeutic agent (e.g., type, dosing and frequency of administration) must be weighed against certain adverse side effects of such a treatment. Chemotherapeutic agents sometimes kill cancer cells as well as "normal" non-cancerous cells. Thus there is a need for improving the efficacy of chemotherapeutic agents to more specifically target and/or to more effectively kill cancer cells while reducing the toxic affects of such agents on non-cancerous cells.

One problem associated with certain chemotherapeutic regimes is chemotherapy-induced sterility. Chemotherapy is often the first-line of treatment in men for many cancers, including for example leukemia, lymphoma, testicular tumors, central nervous system tumors, and melanomas. After cycles of combined cancer chemotherapy many young men have long term cancer-free survival but are infertile because chemotherapeutic drugs induced cell death of immature germ cells including spermatogonial stem cells.

Cyclophosphamide (CP) is an example of a chemotherapeutic agent used in men and in experimental animals. CP treatment causes germ cell damage in rodents and men but requires liver cytochrome P450 metabolism to generate an active metabolite, 4-hydroxy-cyclophosphamide, which circulates to cancer cells and damages DNA leading to apoptosis (Sloderbach, et al., 2013). During in vivo treatment with CP, all differentiated germ cells of mice are eliminated and about half of the undifferentiated germ cells remain. Once treatment is stopped, about 64% of germ cells regenerate from these undifferentiated stem cells (Drumond, et al., 2011). Even though CP does not completely eliminate stem cell spermatogonia in the short term, stem cell spermatogonia loss may not be completely reversible in cancer patients after multiple cycles of cancer chemotherapy. Some recovery has been reported in rodents (Delbes, et al., 2010) and men (Dohle, 2010; Meistrich, 2013; Trost & Brannigan, 2012). Currently in men, cryopreservation of spermatozoa is a recommended method to preserve male fertility in post-pubertal men and experimental cryopreservation of testicular tissue for prepubertal boys. However, in some cases where a cancer is metastatic and the patient is severely ill, spermatogenesis may be impaired and the quality of a sample collected before treatment may be poor and not suitable for use in assisted reproductive technologies (Choy & Brannigan, 2013; Loren, et al., 2013; Nangia, et al., 2013).

Compositions and methods disclosed herein can alter the effects of certain chemotherapeutic agents resulting in, for example, protection of germ cells from chemotherapy-induced death and/or enhancement of chemotherapy-induced death of cancer cells.

SUMMARY

Provided herein, in some aspects, is a method of enhancing treatment of a metastatic or non-metastatic neoplasia, tumor, cancer or malignancy in a subject, comprising administering to the subject an amount of humanin or a humanin analog and a chemotherapeutic agent thereby enhancing treatment of the metastatic or non-metastatic neoplasia, tumor, cancer or malignancy in the subject.

Provided herein, in some aspects, is a method of treating a subject having a metastatic or non-metastatic neoplasia, tumor, cancer or malignancy, comprising administering to the subject an amount of humanin or a humanin analog and a chemotherapeutic agent sufficient to reduce or inhibit proliferation of the metastatic or non-metastatic neoplasia, tumor, cancer or malignancy.

Provided herein, in some aspects, is a method of enhancing treatment of a hyperproliferative disorder in a subject, comprising administering to the subject an amount of humanin or a humanin analog and a chemotherapeutic agent thereby enhancing treatment of the hyperproliferative disorder in the subject.

Provided herein, in some aspects, is a method of treating a subject having a hyperproliferative disorder, comprising administering to the subject an amount of humanin or a humanin analog and a chemotherapeutic agent sufficient to treat the hyperproliferative disorder.

In some embodiments the treatment results in partial or complete destruction of the hyperproliferative cell, or the neoplastic, tumor, cancer or malignant cell mass, volume, size or numbers of cells; stimulating, inducing or increasing hyperproliferative cell or the neoplastic, tumor, cancer or malignant cell necrosis, lysis or apoptosis; reducing hyperproliferative cell or neoplasia, tumor, cancer or malignancy volume size or cell mass; inhibiting or preventing progression or an increase in hyperproliferative cell or neoplasia, tumor, cancer or malignancy volume, mass, size or cell numbers, reducing neoplasia, tumor, cancer or malignancy metastasis volume, size or cell mass; or prolonging lifespan. In some embodiments the treatment results in reducing or decreasing severity, duration or frequency of an adverse symptom or complication associated with or caused by the hyperproliferative cell or the neoplasia, tumor, cancer or malignancy. In some embodiments the treatment results in reducing or decreasing pain, discomfort, nausea, weakness or lethargy, or results in increased energy, appetite, improved mobility or psychological well being.

In some embodiments a humanin or humanin analog increases efficacy or activity of the chemotherapeutic agent. In certain embodiments, a humanin or humanin analog does not substantially reduce, decrease, suppress or inhibit efficacy or activity of the chemotherapeutic agent.

In certain embodiments a method described herein inhibits or reduces relapse or progression of the neoplasia, tumor, cancer or malignancy.

In some aspects, presented herein is a method of enhancing an anti-cancer effect of a chemotherapeutic agent in a subject comprising a) providing a subject having or suspected of having a hyperproliferative disorder, and b) administering a composition to the subject, where the composition comprises one or more humanin polypeptides of tables 1-4, where a chemotherapeutic agent is administered to the subject prior to, during or after administering the composition of (b), and where the composition is administered in an amount sufficient to enhance the cytotoxic effects of the chemotherapeutic agent on a hyperproliferative tissue.

In certain embodiments, a subject has a hyperproliferative disorder. In some aspects, a subject has a metastatic or non-metastatic neoplasia, tumor, cancer or malignancy. In certain aspects, a humanin or a humanin analog does not substantially reduce, decrease, suppress or inhibit efficacy or activity of the chemotherapeutic agent. Also, in some embodiments, the efficacy or activity of the chemotherapeutic agent comprises partial or complete destruction of a hyperproliferative cell, or a neoplastic, tumor, cancer or malignant cell mass, volume, size or numbers of cells; stimulating, inducing or increasing hyperproliferative cell or neoplastic, tumor, cancer or malignant cell necrosis, lysis or apoptosis; reduces hyperproliferative cell or neoplasia, tumor, cancer or malignancy volume size or cell mass; inhibits or prevents progression or an increase in hyperproliferative cell or neoplasia, tumor, cancer or malignancy volume, mass, size or cell numbers, reduces neoplasia, tumor, cancer or malignancy metastasis volume, size or cell mass; or prolongs lifespan.

In some embodiments humanin or a humanin polypeptide comprises the sequence: MAPRGFSCLLLLT-SEIDLPVKRRA. In some embodiments a humanin analog or humanin polypeptide comprises the sequence: MAPRGF-SCLLLLTGEIDLPVKRRA (HN-S14G), or any sequence set forth in Example 1 or Tables 1-4. In some embodiments a humanin polypeptide is selected from one or more of SEQ ID NO:1, SEQ ID NO:2, HNG-F6A, HN-F6A, HN-S7A and HN-C8P. In some embodiments a humanin polypeptide is SEQ ID NO:1. In some embodiments a humanin polypeptide is SEQ ID NO: 2.

In some aspects, the chemotherapeutic agent comprises an alkylating agent, an anthracycline, an anti-metabolite, plant extract, plant alkaloid, nitrosourea, hormone, nucleoside or nucleotide analog. In some aspects the chemotherapeutic agent comprises a DNA intercalating agent or an agent that attaches or bonds to DNA. In some aspects, the chemotherapeutic agent comprises cyclophosphamide, doxorubicin, azathioprine, cyclosporin A, prednisolone, melphalan, chlorambucil, mechlorethamine, busulphan, methotrexate, 6-mercaptopurine, thioguanine, 5-fluorouracil, cytosine arabinoside, 5-azacytidine (5-AZC) and 5-azacytidine related compounds, bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, a taxane, vinblastine, vincristine, dibromomannitol, gemcitabine, or pemetrexed. In some embodiments a chemotherapeutic agent comprises an alkylating anti-neoplastic agent. In some embodiments the alkylating anti-neoplastic agent comprises Temozolomide or cyclophosphamide. In some embodiments the chemotherapeutic agent comprises a DNA intercalating agent. In some embodiments a DNA intercalating agent comprises doxorubicin.

In some embodiments a neoplasia, tumor, cancer or malignancy is metastatic, non-metastatic or benign. In some embodiments a neoplasia, tumor, cancer or malignancy comprises a solid cellular mass. In some embodiments a neoplasia, tumor, cancer or malignancy comprises hematopoietic cells. In certain embodiments a neoplasia, tumor, cancer or malignancy comprises a carcinoma, sarcoma, lymphoma, leukemia, adenoma, adenocarcinoma, melanoma, glioma, glioblastoma, medulloblastoma, meningioma, neuroblastoma, retinoblastoma, astrocytoma, oligodendrocytoma, mesothelioma, reticuloendothelial, lymphatic or haematopoietic neoplasia, tumor, cancer or malignancy. In certain aspects a sarcoma comprises a lymphosarcoma, liposarcoma, osteosarcoma, chondrosarcoma, leiomyosarcoma, rhabdomyosarcoma or fibrosarcoma. In some aspects a haematopoietic neoplasia, tumor, cancer or malignancy comprises a myeloma, lymphoma or leukemia. In some aspects a neoplasia, tumor, cancer or malignancy comprises a metastatic melanoma. In some aspects a neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, or skin, lung, biliary tract, or hematologic neoplasia, tumor, or cancer.

In certain aspects a method herein further comprising administering a second, third or fourth chemotherapeutic agent.

In some embodiments a humanin or humanin analog is administered prior to, substantially contemporaneously with or following administration of the chemotherapeutic agent. In some embodiments a humanin or humanin analog is administered in combination with the chemotherapeutic agent.

In some aspects a subject has undergone surgical resection, chemotherapy, immunotherapy, ionizing or chemical radiotherapy, local or regional thermal (hyperthermia) therapy, or vaccination. In some aspects a subject is or is not a candidate for surgical resection, chemotherapy, immunotherapy, ionizing or chemical radiotherapy, local or regional thermal (hyperthermia) therapy, or vaccination.

Certain embodiments are described further in the following description, examples, claims and drawings.

BRIEF DESCRIPTION OF THE DRAWINGS

FIGS. 4A-D show TUNEL positive apoptotic germ cells (dark grey or brown in color) at stage XII (late stage) of seminiferous epithelial cycle in testis of control (FIG. 4A), HN treated (FIG. 4B), CP treated (FIG. 4C), and combined HN and CP treatment mice (FIG. 4D). Scale bar, 20 μm. FIG. 4E (Right Panel) shows quantification of germ cell apoptosis at early/late stages IX-IV as the percentage of tubules with apoptotic cells/100 tubules (y-axis, mean±SEM) in mice after receiving no treatment (Control), Humanin alone (HN), cyclophosphamide alone (CP), or cyclophosphamide and Humanin (CP+HN). Means with unlike superscripts (e.g., a, b and c as shown above the histograms) are significantly different (P<0.05).

FIGS. 5A-D show TUNEL positive apoptotic germ cells (dark grey or brown in color) at stages VII (middle stage) of seminiferous epithelial cycle in testis of control (FIG. 5A), HN treated (FIG. 5B), CP treated (FIG. 5C), and combined HN and CP treatment mice (FIG. 5D). Scale bar, 20 μm. FIG. 5E (Right Panel) shows quantification of germ cell apoptosis at middle stages IX-IV as the percentage of tubules with apoptotic cells/100 tubules (y-axis, mean±SEM) in mice after receiving no treatment (Control), Humanin alone (HN), cyclophosphamide alone (CP), or cyclophosphamide and Humanin (CP+HN). Means with unlike superscripts (e.g., a and b as shown above the histograms) are significantly different (P<0.05).

(FIGS. 16A and 16B): Apoptotic cell numbers were determined by TUNEL staining method. HN or HN-S7A alone did not change apoptosis compared with control. Compared with control, CP increased germ cell apoptosis both in early+late (I-IV and XI-XII, FIG. 16A) and middle (VII-VIII, FIG. 16B) stages. HN significantly suppressed CP-induced apoptosis in early+late stages but not in middle stages. HN-S7A prevented CP-induce apoptosis both in early+late and middle stages remarkably. Addition of HN-S7A to HN did not change the effect of HN on CP-induced apoptosis. Values are means±SEM. (FIGS. 16C and 16D): Change of STAT3 phosphorylation levels were detected by western blot (FIG. 16C) and presented by density ratio of phosphorylated STAT3/STAT3 (FIG. 16D). HN or HN-S7A alone did not change STAT3 phosphorylation compared with control. Compared with control, CP suppressed STAT3 phosphorylation. CP+HN, CP+HN-S7A, or CP+HN+HN-S7A all restored CP suppressed STAT3 phosphorylation. Density values are means±SEM. Values are means±SEM. Means with unlike superscripts (e.g., a and b as shown above the histograms) are significantly different (P<0.05).

(FIGS. 17A and 17B): Apoptotic cell numbers were determined by TUNEL staining method. HN or HN-C8P alone did not change apoptosis compared with control. Compared with control, CP induced massive germ cell apoptosis both in early+late (I-IV and XI-XII, FIG. 17A) and middle (VII-VIII, FIG. 17B) stages. CP+HN significantly suppressed CP-induced apoptosis in early+late stages but not in middle stages. CP+HN-C8P showed weaker preventive effect against CP-induce apoptosis in early+late (p<0.05, compared with CP+HN) but no protective effect in middle stages. Addition of HN-C8P did not change the preventive effect of HN on CP-induced germ cell apoptosis. Values are means±SEM. (FIGS. 17C and 17D): Changes of STAT3 phosphorylation levels were detected by western blot (FIG. 17C) and presented by density ratio of phosphorylated STAT3/STAT3 (FIG. 17D). HN or HN-C8P alone did not change STAT3 phosphorylation compared with control. Compared with control, CP suppressed STAT3 phosphorylation. CP+HN, CP+HN-C8P, or CP+HN+HN-C8P all restored CP suppressed STAT3 phosphorylation. Density values are means±SEM. Values are means±SEM. Means with unlike superscripts (e.g., a and b as shown above the histograms) are significantly different (P<0.05).

FIGS. 29A-29B show Apoptotic Index [% of cross sections of seminiferous tubules (ST) containing TUNEL positive germ cells/total cross sections of seminiferous tubules](y axis) at early (I-VI) and late (IX-XIV) stages of seminiferous epithelium cycle (FIG. 29A). In the groups of rats with the presence of Leydig cells (light bars), CP increased apoptosis compared to vehicle (p=0.0019, dashed bracket) control, and HN reduced the CP-induced apoptosis (p=0.021). EDS pre-treatment (dark bars) had a minimal effect on apoptosis of germ cells (p=0.169), and HN had no significant effect on apoptosis in the EDS (p=0.251) (FIG. 29A, dark bars) at early and late stages. FIG. 29B shows Apoptotic Index (y axis) at middle (VII-VIII) stages of seminiferous epithelium cycle. CP did not increase apoptosis in the middle stages in animals not pre-treated with EDS (FIG. 29B. light bars). In the EDS pre-treated rats (dark bars), EDS increased apoptosis of germ cells compared to control (p=0.0014, dashed bracket) and HN decreased apoptosis levels in EDS treated rats (p=0.018). Addition of CP to EDS did not further increased germ cell apoptosis. CP+EDS increased apoptosis compared to control (p=0.0011, dashed bracket) and HN prevented apoptosis EDS+CP treated rats (p=0.04) (FIG. 29B. Dark bars). There were 4 rats in each group.

DETAILED DESCRIPTION

Figure 1:
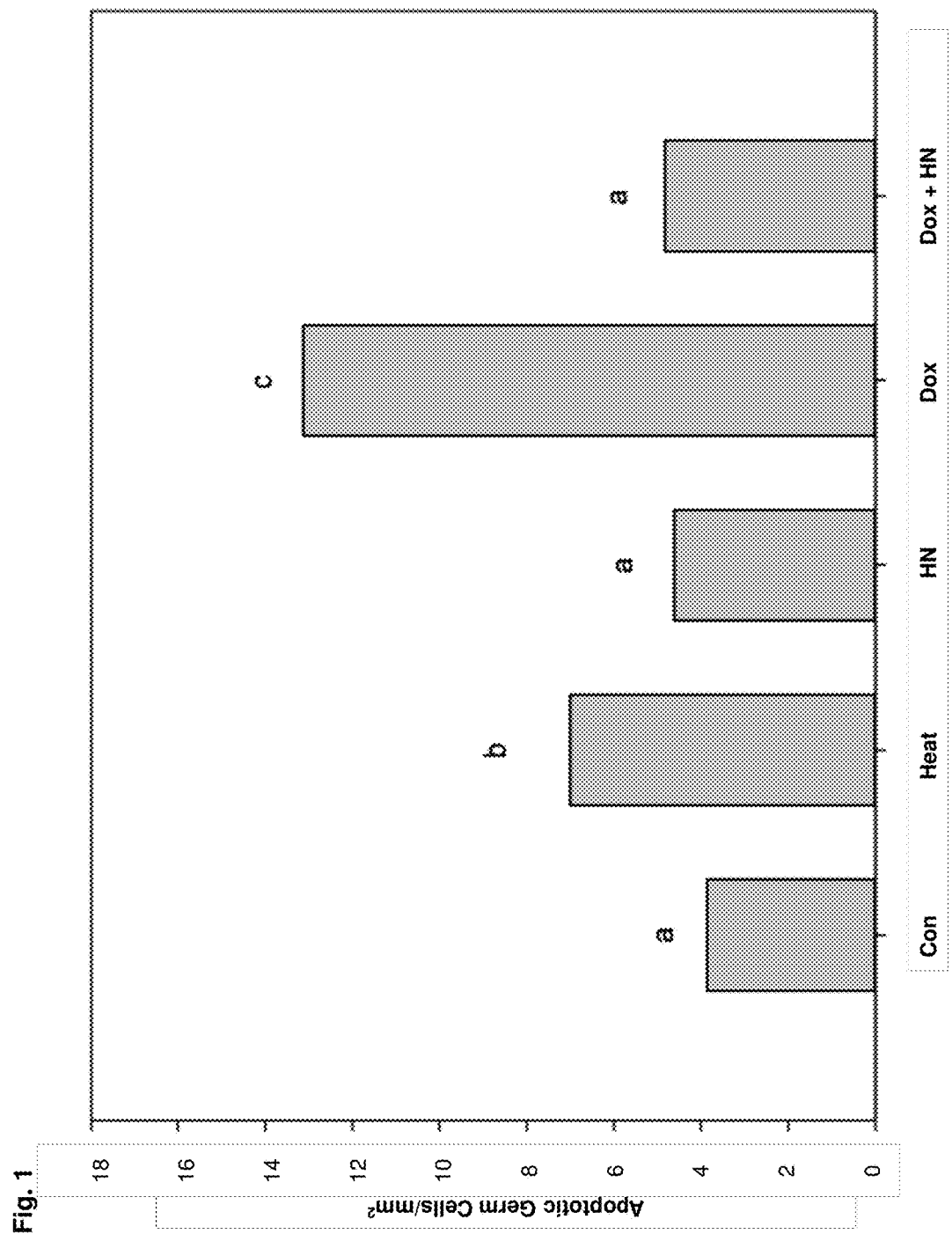
FIG. 1 shows a histogram of the quantity of apoptotic cells in squashed seminiferous tubules (y-axis, mean±SEM) after doxorubicin (DOX), Humanin (HN), Dox and HN (Dox+HN) or no treatment (Con) ex-vivo. Exposing the seminiferous tubules to 43 degrees served as a positive control (Heat). Means with unlike superscripts (e.g., a, b and c as shown above the histograms) are significantly different ($P<0.05$).

Described herein are compositions comprising humanin and/or one or more humanin analogs and method of use thereof. In some embodiments a composition comprises a humanin polypeptide and/or a polypeptide of a human analog. In some embodiments a composition described herein comprises one or more polypeptides comprising a humanin polypeptide and/or a polypeptide of a human analog. Humanin and/or a humanin analog or composition thereof can be incorporated into pharmaceutical compositions, e.g., a composition comprising a pharmaceutically acceptable carrier and/or excipient. Such pharmaceutical compositions are useful for, among other things, administration and/or delivery to a subject.

Humanin (HN) is a 24-amino acid mitochondrial derived peptide with the amino acid sequence of SEQ ID NO:1 (HN, humanin polypeptide). Humanin is an endogenous peptide found in many tissues including neurons (Hashimoto, et al., 2001; Hashimoto, et al., 2001), endothelial cells (Bachar, et al., 2010), pancreatic beta cells (Hoang, et al., 2010), and cardiomyocytes (Muzumdar, et al., 2010). HN is expressed in germ cells and Leydig cells in testes (Colon, et al., 2006; Moretti, et al., 2010). HN reportedly protects against male germ cell apoptosis induced by testicular hormonal deprivation (Jia, et al., 2013; Lue, et al., 2010). In addition to the finding of endogenous HN (peptide or gene) in normal tissues and cells, HN has been proposed as an potential oncopeptide (Maximov, et al., 2002) because HN gene is expressed in cutaneous T-cell lymphoma (Hartmann, et al., 2008), diffuse large B-cell lymphoma (Tarantul & Hunsmann, 2001), and gastric cancer (Mottaghi-Dastjerdi, et al., 2014).

In some embodiments, humanin comprises the amino acid sequence of SEQ ID NO: 1. A humanin analog can be a humanin variant or derivative thereof. Non-limiting examples of humanin, humanin analogs and/or variants applicable to the methods, uses and compositions set forth herein are shown and described in Example 1 and Tables 1-4. Humanin and humanin analogs (i.e., collectively referred to as humanin polypeptides), and/or derivatives thereof are contemplated for compositions and methods described herein. A derivative of humanin or a derivative of a humanin analog may comprise any suitable amino acid modification, and/or may comprise amino acid analogs or conjugates. For example, a derivative of humanin or humanin analogs may be conjugated to a label, an antibody, a tag, a carrier protein, a ligand, the like or combinations thereof.

As described herein, compositions comprising humanin and/or one or more humanin analogs can be used to alter the effects of chemotherapeutic agents. As disclosed herein, HN and HN analogs can be used as agents to protect germ cells from death and/or damage caused by chemotherapeutic agents that are sometimes used for treatment of cancer and tumors. For example, as shown herein HN and HN analogs are able to protect animals against chemotherapy induced germ cell apoptosis by cyclophosphamide (CP), doxorubicin (dox) and/or temozolomide (TMZ) treatment. In some embodiments, HN and/or HN analogs can be used to enhance chemotherapy induced tumor cell cytotoxicity. For example, as shown herein, HN and/or HN analogs can enhance tumor cell apoptosis induced by cyclophosphamide (CP), doxorubicin (dox) and/or Temozolomide (TMZ) treatment. These discoveries are clinically relevant, as methods, uses and compositions described herein can be used as an adjunct to treatments of certain hyperproliferative disorders, (e.g., neoplasias, tumors, cancers and malignancies) in which germ cell development is suppressed and/or where germ cells are killed by treatment with chemotherapy. In certain embodiments, method and compositions herein can protect a cancer patient from many common adverse effects of chemotherapy and/or enhance the desired anti-tumor effects of a chemotherapeutic agent.

Methods, uses and compositions herein are applicable to any subject. The term "subject" refers to animals, typically mammalian animals. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). A mammal can be any age or at any stage of development (e.g., an adult, teen, child, infant, or a mammal in utero). A mammal can be male or female. A mammal can be a pregnant female. In certain embodiments a mammal can be an animal disease model, for example, animal models used for the study of viral infections. In some embodiments a mammal is a human. In some embodiments a mammal is a human male. In some embodiments a mammal is a human female.

A patient can be any subject suspected of having, diagnosed with, suspected of having, or undergoing treatment for an ailment, disease or infection, or a subject who could benefit from a use or method herein. In certain embodiments a subject has a hyperproliferative disorder (e.g., a cancer) and/or is undergoing a treatment for a hyperproliferative disorder. A subject can have any type of hyperproliferative disorder. In some embodiments, a subject has, or is suspected of having a hyperproliferative disorder thought to be treatable by a chemotherapeutic agent.

In some embodiments a subject is undergoing, has undergone, or will undergo a treatment for a hyperproliferative disorder. In some embodiments a subject is a candidate for a treatment for a hyperproliferative disorder. Non-limiting examples of a treatment for a hyperproliferative disorder include a surgical resection, chemotherapy, targeted therapy (e.g., immunotherapy, antibody therapy), ionizing radiotherapy (e.g., radiation therapy, proton therapy and the like), chemical radiotherapy, local or regional thermal (hyperthermia) therapy, hormonal therapy, adjuvant therapy, a vaccination, the like, or combinations thereof.

In certain embodiments a subject is undergoing, has undergone or will undergo chemotherapy. In certain embodiments a subject is a candidate for a chemotherapy treatment. Chemotherapy comprises administration of one or more chemotherapeutic agents to a subject. A chemotherapeutic agent may be self-administered or administered by another (e.g., by a health care professional). A chemotherapeutic agent can be administered by any suitable method (e.g., by any suitable route, at any suitable dose, for any suitable amount of time (e.g., continuously, periodically, and the like)).

In some embodiments a subject is not undergoing or has not undergone a treatment for a hyperproliferative disorder. In some embodiments a subject is not a candidate for one or more treatments for a hyperproliferative disorder, non-limiting examples of which include a surgical resection, targeted therapy (e.g., immunotherapy, antibody therapy), ionizing radiotherapy (e.g., radiation therapy, proton therapy and the like), chemical radiotherapy, local or regional thermal (hyperthermia) therapy, hormonal therapy, adjuvant therapy, a vaccination, the like, or combinations thereof. In some embodiments a subject is not a candidate for chemotherapy.

In some embodiments a hyperproliferative disorder is characterized or named according to the presence of a hyperproliferative tissue or cell type. Non-limiting examples of a hyperproliferative disorder and/or hyperproliferative tissue/cell types include melanoma, lymphoma (e.g., Hodgkin lymphoma, non-Hodgkin lymphoma, a B-cell neoplasm, a T-cell neoplasm, an NK cell neoplasm), leukemia, reticuloendothelial hyperplasia (e.g., reticuloendothelial neoplasia), lymphatic neoplasia, hematopoietic neoplasia, myeloma, multiple myeloma, an immunodeficiency-associated lymphoproliferative disorder, adenoma, adenocarcinoma, sarcoma (non-limiting examples of which include a lymphosarcoma, liposarcoma, osteosarcoma, chondrosarcoma, leiomyosarcoma, rhabdomyosarcoma, fibrosarcoma, the like or combinations thereof), carcinoma, breast cancer, colorectal cancer, gastrointestinal cancer, hepatocellular cancer, lung cancer, bone cancer, renal cancer, bladder cancer, hepatoma, neuroblastoma, retinoblastoma, astrocytoma, glioma, glioblastoma, medulloblastoma, meningioma, oligodendrocytoma, cervical cancer, testicular cancer, ovarian cancer, mesothelioma, esophageal cancer, pancreatic cancer, prostate cancer, the like or combinations thereof. A hyperproliferative disorder may be benign, malignant, metastatic, non-metastatic or undetermined.

In some embodiments a neoplasia, tumor, cancer or malignancy comprises a metastatic melanoma. In some embodiments a neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, or skin, lung, biliary tract, or hematologic neoplasia, tumor, or cancer. In some embodiments a neoplasia, tumor, cancer or malignancy comprises a solid cellular mass. In certain embodiments a malignant neoplasm comprises or consist of a fibrosarcoma, myxosarcoma, liposarcoma, chondrosarcoma, osteosarcoma, chordoma, malignant fibrous histiocytoma, hemangiosarcoma, angiosarcoma, lymphangiosarcoma, mesothelioma, leiomyosarcoma, rhabdomyosarcoma, squamous cell carcinoma, epidermoid carcinoma, malignant skin adnexal tumor, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma, glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, oat cell carcinoma, malignant pheochromocytoma, islet cell carcinoma, malignant carcinoid, retinoblastoma, chemodectoma, paraganglioma, malignant carcinoid, malignant paraganglioma, melanoma, malignant schwannoma, merkel cell neoplasm, cystosarcoma phylloides, wilms tumor, malignant ovarian tumors, malignant testicular tumors, the like, or combinations thereof. In certain embodiments a neoplasia, tumor, cancer or malignancy comprises a carcinoma, sarcoma, lymphoma, leukemia, adenoma, adenocarcinoma, melanoma, glioma, glioblastoma, medulloblastoma, Kaposi sarcoma, meningioma, neuroblastoma, retinoblastoma, astrocytoma, oligodendrocytoma, reticuloendothelial, lymphatic or haematopoietic neoplasia, tumor, cancer or malignancy. In certain embodiments a sarcoma comprises a lymphosarcoma, liposarcoma, osteosarcoma, chondrosarcoma, leiomyosarcoma, rhabdomyosarcoma or fibrosarcoma.

In certain embodiments a neoplasia, tumor, cancer or malignancy comprises a metastatic melanoma. In certain embodiments a neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, or skin, lung, biliary tract, or hematologic neoplasia, tumor, or cancer.

In some embodiments a leukemia is an acute lymphocytic leukemia (ALL), acute myeloid leukemia (AML), chronic lymphocytic leukemia (CLL), chronic myeloid leukemia (CML), or chronic myelomonocytic leukemia (CMML).

Any suitable chemotherapeutic agent can be administered to a subject. Chemotherapeutic agents are often administered to a subject (e.g., a patient) for the treatment of a hyperproliferative disease or disorder. Chemotherapeutic agents can include a variety of poisons, venoms, toxins, proteins, antibodies and inhibitors that can induce suppression of cellular activities and/or death of a mammalian cell by a variety of mechanisms, non-limiting examples of which include apoptosis (programmed cell death), activation-induced cell death, autophagy, necrosis, necroptosis, and the like). Cell death and/or viability can be determined by a suitable assay known in the art or described herein, non-limiting examples of which include a suitable membrane alteration assay (e.g., as measured by annexin-V binding, uptake of impermeable dyes such as propidium iodide, trypan blue, LDH release, the like or combinations thereof), caspase activation assays (e.g., as measured by peptide substrate cleavage, substrate cleavage (e.g., PARP, M30), caspase processing, the like or combinations thereof), DNA fragmentation assays (e.g., TUNEL assay, or assessment of DNA laddering, cytoplasmic nucleosomes, hypodipoloid DNA, and release of incorporated nucleotides (e.g., BrdU), the like, or combinations thereof), mitochondrial damage assays (e.g., measurements of cytochrome C release, mitochondrial membrane potential, ATP production, electron transport activity (e.g., WST-1 or MTT assays)), the like or combinations thereof.

In certain embodiments a cellular activity is suppressed by a chemotherapeutic agent. Non-limiting examples of cellular activities that may be suppressed by a therapeutic agent include growth, mitosis, meiosis, motility, respiration, maturation, differentiation, transcription, translation, DNA replication, mitochondrial respiration, certain catabolic or metabolic activities, secretion, endocytosis, phagocytosis, the like, or combinations thereof. In some embodiments, suppression and grammatical variations thereof, refers to an adverse effect of a chemotherapeutic agent on a cell that results in the inhibition, reduction or loss of one or more functions of the cell. In some embodiments the inhibition, reduction or loss of one or more cell functions refers to the loss of, or inhibition of, a cell's ability to replicate (e.g., proliferate) and/or undergo mitosis or meiosis. In some embodiments the inhibition, reduction or loss of one or more cell functions refers to the loss of, or inhibition of, a cell's ability to metabolize oxygen, proteins, fatty acids, carbohydrates and/or glucose. In some embodiments the inhibition, reduction or loss of one or more cell functions refers to the loss of, or inhibition of, a cell's ability to initiate, carry out, maintain or terminate an adaptive or innate immune response, or a portion thereof. In some embodiments the inhibition, reduction or loss of one or more cell functions refers to the loss of, or inhibition of, a cell's ability to initiate, carry out, maintain or terminate an immune function, non-limiting examples of which include antigen presentation; apoptosis; phagocytosis; pinocytosis; T-cell activation; B-cell activation; expressing, presenting, secreting and/or responding to an antigen, cytokine, chemokine, growth factors, TNF or TNF-related family members, interferon, porin, defensin, complement, protease, antibody, a hormone, and/or receptors thereof; the like; or combinations thereof.

Suppression and/or death of one or more cells can be induced by a chemotherapeutic agent. Suppression and/or death of cells can be induced when a cell comes into contact with one or more chemotherapeutic agents. In some embodiments a chemotherapeutic agent is cytotoxic to a cell. In certain embodiments, administration of a chemotherapeutic agent to a subject induces, promotes, increases and/or stimulates suppression and/or death of germ cells in the absence of a method described herein (e.g., in the absence of administering humanin or a humanin analog). In certain embodiments, administration of a therapeutic agent to a subject reduces, decreases, or inhibits maturation, proliferation and/or survival of germ cells in the absence of a method described herein (e.g., in the absence of administering humanin or a humanin analog). In certain embodiments, administration of a chemotherapeutic agent to a subject damages germ cells in the absence of a method described herein (e.g., in the absence of administering humanin or a humanin analog). Cell damage may include damage to genomic DNA, mitochondria or other organelles, mitochondrial DNA, mitochondrial cell walls or phospholipid membranes.

In some embodiments a chemotherapeutic agent comprises a cytotoxic compound. In some embodiments a chemotherapeutic agent comprises or consists of one or more cytotoxic compounds. Cytotoxic compounds can be organic or inorganic compounds. In some embodiments cytotoxic compounds are relatively small compounds with a molecular weight between 1 and about 20,000 Daltons, 1 and about 10,000 Daltons, 1 and about 5000 Daltons, 1 and about 2500 Daltons, 1 and about 1000 Daltons, 1 and about 500 Daltons or between about 50 and about 1000 Daltons.

In some embodiments a chemotherapeutic agents is a protein or polypeptide. In some embodiments a chemotherapeutic agents is an antibody (e.g., a monoclonal or polyclonal antibody). Chemotherapeutic agents can be polypeptides or fusion proteins. In some embodiments, chemotherapeutic agents are not cytotoxic until after they are administered to a subject wherein the chemotherapeutic agents are metabolized into a cytotoxic compound (e.g., cyclophosphamide). In some embodiments a cell is contacted with a chemotherapeutic agent and the cell metabolizes the chemotherapeutic agent into a cytotoxic compound. A cell can be contacted directly or indirectly (e.g., by a targeted approach) with a chemotherapeutic agent. In some embodiments a chemotherapeutic agents is autoimmune chemotherapeutic agents for treatment of an autoimmune disorder.

In some embodiments a chemotherapeutic agent comprises or consists of an alkylating agent, an anthracycline, cytoskeletal disruptors, epothilones (e.g., epothilone), histone deacetylase inhibitors (e.g., vorinostat, romidepsin), inhibitors of topoisomerase I (e.g., irinotecan, topotecan), inhibitors of topoisomerase II (e.g., etoposide, teniposide, tafluposidean), kinase inhibitors, peptide antibiotics (e.g., bleomycin, actinomycin), platinum-based agents (e.g., carboplatin, cisplatin, oxaliplatin), retinoids (e.g., tretinoin, alitretinoin, bexarotene), vinca alkaloids and derivatives (e.g., vinblastine, vincristine, vindesine, vinorelbine), anti-metabolites, plant extracts, plant alkaloids, nitrosourea, hormone, nucleoside or nucleotide analog and combinations thereof.

In some embodiments a chemotherapeutic agent comprises an alkylating anti-neoplastic agent (e.g., an alkylating anti-neoplastic agent. An alkylating antineoplastic agent is a class of chemotherapeutic agents that work, in part, by attaching an alkyl group (e.g., $C_nH_{2n+1}$) to DNA, a process known alkyation. Some alkylating antineoplastic agents are administered as a pro-drug that is converted in vivo to an active alkylating agent. An alkylating antineoplastic agent often alkylates a guanine base of DNA. Alkylating antineoplastic agents are most effective on proliferating cells (e.g., cancer cells) which, in general, proliferate faster and with less error-correcting than healthy cells. Without being limited to theory, it is thought that proliferating cells are more sensitive to DNA damage (e.g., alkylation), which often initiates a cell death pathway (e.g., apoptosis). However, Alkylating antineoplastic agents can also be toxic to normal cells (cytotoxic), in particular in cells that divide frequently, such as those in the gastrointestinal tract, bone marrow, and germ cells of the testicles and ovaries. Non-limiting examples of alkylating anti-neoplastic agents Altretamine (hexamethylmelamine, HEXALEN®), Busulfan, Carmustine (BCNU), Chlorambucil, Cyclophosphamide, Dacarbazine (DTIC), Ifosfamide, Lomustine (CCNU), Mechlorethamine, Melphalan, Procarbazine, Streptozotocin, Temozolomide, Thiotepa (triethylenethio-phosphoramide), Carboplatin, Cisplatin, Oxaliplatin, the like or combinations thereof. In some embodiments a chemotherapeutic agent comprises Altretamine (hexamethylmelamine, HEXALEN®), Busulfan, Carmustine (BCNU), Chlorambucil, Cyclophosphamide, Dacarbazine (DTIC), Fotemustine, Ifosfamide, Lomustine (CCNU), Mechlorethamine, Melphalan, Procarbazine, semustine (MeCCNU), Streptozotocin, Temozolomide, Thiotepa (triethylenethio-phosphoramide), Carboplatin, Cisplatin, and/or Oxaliplatin, monofunctional alkylators, nitrosoureas, temozolomide, the like, analogs or combinations thereof.

In some embodiments a chemotherapeutic agent comprises a DNA intercalating agent which is often an agent that attaches or bonds to DNA or RNA. In some embodiments a DNA intercalting agent comprises an anthracycline. In some embodiments a DNA intercalating agent comprises or consists of acrolein, phosphoramide, Actinomycin D, bleomycin, idarubicin, daunorubicin, doxorubicin, elsamicin A, epirubicin, ethidium, m-AMSA, mitoxantrone, doxorubicin (Adriamycin, Doxil, Myocet, hydroxydaunorubicin, hydroxydaunomycin), Epirubicin, Idarubicin, Valrubicin, TAS-103, MLN944 (XR5944), Obatoclax, mechlorethamine, methotrexate, 6-mercaptopurine, thioguanine, 5-fluorouracil, cytosine arabinoside, 5-azacytidine (5-AZC) and 5-azacytidine related compounds, mithramycin, mitomycin C, hydroxyurea, carboplatin, oxiplatin, mitotane, a taxane, vinblastine, vincristine, dibromomannitol, gemcitabine, pemetrexed, the like or a combination thereof. In some embodiments a DNA intercalating agent comprises or consists of Actinomycin D, bleomycin, daunorubicin, doxorubicin, elsamicin A, epirubicin, ethidium, m-AMSA, mitoxantrone, doxorubicin (Adriamycin, Doxil, Myocet, hydroxydaunorubicin, hydroxydaunomycin), Epirubicin, Idarubicin, Valrubicin, TAS-103, MLN944 (XR5944), and Obatoclax.

In some embodiments a chemotherapeutic agent comprises a cytoskeletal disruptor. Non-limiting examples of cytoskeletal disruptors (e.g., taxanes) include paclitaxel, taxol, and docetaxel.

In some embodiments a chemotherapeutic agent comprises a kinase inhibitor. Non-limiting examples of kinase inhibitors include bortezomib, erlotinib, gefitinib, imatinib, vemurafenib, vismodegib, the like, analogs and derivatives thereof.

In some embodiments a chemotherapeutic agent comprises one or more nucleotide analogs. Non-limiting examples of nucleotide analogs include azacitidine, azathioprine, capecitabine, cytarabine, doxifluridine, fluorouracil, gemcitabine, hydroxyurea, mercaptopurine, methotrexate, tioguanine (formerly thioguanine), the like, analogs and derivatives thereof.

In some embodiments a chemotherapeutic agent comprises one or more different chemotherapeutic agents. In some embodiments a chemotherapeutic agent comprises a cocktail of chemotherapeutic agents comprising two, three, four, five or more chemotherapeutic agents.

In some embodiments a chemotherapeutic agent induces partial or complete destruction of some or all hyperproliferative cells in a subject. In some embodiments a chemotherapeutic agent induces partial or complete destruction of a neoplastic, tumor, cancer or malignant cell mass in a subject. A chemotherapeutic agent can decrease the volume or size of a neoplasia, neoplastic tumor, cancer or malignancy and/or reduce the numbers of hyperproliferative cells in a subject. In some embodiments a chemotherapeutic agent stimulates and/or induces apoptosis, necrosis, and/or lysis of hyperproliferative cells or cells of a neoplastic tumor, cancer or malignant cell masses in a subject. In some embodiments a chemotherapeutic agent inhibits or prevents progression of or an increase in hyperproliferative cells or a neoplasia, tumor, cancer or malignancy. In some embodiments a chemotherapeutic agent prolongs lifespan of a subject comprising a hyperproliferative disease or disorder. The efficacy or activity of a chemotherapeutic agent can be determined according to one or more of 1) its ability and effectiveness to induce partial or complete destruction of some or all hyperproliferative cells in a subject, 2) induce partial or complete destruction of a neoplastic, tumor, cancer or malignant cell mass in a subject, 3) decrease the volume or size of a neoplasia, neoplastic tumor, cancer or malignancy and/or reduce the numbers of hyperproliferative cells in a subject, 4) stimulate and/or induces apoptosis, necrosis, and/or lysis of hyperproliferative cells or cells of a neoplastic tumor, cancer or malignant cell masses in a subject, 5) inhibit or prevent progression of or an increase in hyperproliferative cells or a neoplasia, tumor, cancer or malignancy in a subject, and/or 6) prolong the lifespan of a subject comprising a hyperproliferative disease or disorder. In certain embodiments, the administration of humanin or a humanin analog does not substantially reduce, decrease, suppress or inhibit efficacy or activity of a chemotherapeutic agent. In some embodiments, the administration of humanin or a humanin analog enhances, increases or substantially increases efficacy or activity of a chemotherapeutic agent.

A subject often comprises one or more germ cells. A germ cell can be any cell that is, or is destined to become, a sperm or egg. A germ cell can be diploid or haploid. In some embodiments a germ cell is haploid. In some embodiments a germ cell refers to a gametogonia (diploid), primary gametocyte (diploid), secondary gametocyte (haploid), gametid (haploid), and/or a gamete (haploid). In some embodiments a germ cell refers to a spermatogonia (diploid), spermatocyte, spermatid, spermatozoa, and/or a sperm cell. In some embodiments a germ cell refers to Oogonia (diploid), Oocyte (e.g., or a follicle containing an oocyte), and/or Ovum (egg cell). In some embodiments a germ cell is destined to undergo a process of oncogenesis or spermatogenesis. In some embodiments a germ cell is a sperm. In some embodiments a germ cell is an oocyte or ovum.

Administration of a chemotherapeutic agent to a subject can reduce the amount of viable germ cells (e.g., mature sperm, mature ovum or oocytes) in a subject thereby reducing or decreasing fertility in a subject. This is one of the deleterious effects (e.g., adverse effects) of administering a chemotherapeutic agent. Without being limited to theory, a chemotherapeutic agent may reduce the amount of germ cells by inhibiting or suppressing oogenesis and/or spermatogenesis, by inhibiting mitosis or meiosis of germ cells, and/or by inducing cell death of germ cells.

In some embodiments a method, use or composition described herein protects germ cells in a subject from suppression and/or death induced by a chemotherapeutic agent. In some embodiments a method, use or composition described herein inhibits and/or reduces germ cell suppression and/or death induced by a chemotherapeutic agent. Without being limited by theory, a method, use or composition described herein may protect germ cells by preserving germ cell viability and/or function of one or more germ cells from the deleterious effects (e.g., adverse effects) caused by administration of a chemotherapeutic agent. In some embodiments a method, use or composition described herein protects germ cells by inhibiting or blocking chemotherapy-induced (i.e., induced by administration of a chemotherapeutic agent) cell death of germ cells. A method, use or composition described herein may reduce or inhibit the cytotoxic effects of a chemotherapeutic agent on a germ cell, regardless of the mechanism of cytotoxicity. In some embodiments a method, use or composition described herein protects germ cells by inhibiting chemotherapy-induced apoptosis, necrosis, activation-induced cell death, autophagy, and/or necroptosis of germ cells. In some embodiments a method, use or composition described herein protects germ cells by inhibiting chemotherapy-induced apoptosis of germ cells. In certain embodiments a method, use or composition described herein may inhibit certain signaling pathways that may lead to apoptosis where the apoptotic pathway is activated by a chemotherapeutic agent. In some embodiments a method, use or composition described herein protects germ cells from chemotherapy-induced DNA damage (e.g., alkylation, cross-linking, intercalation and the like).

In some embodiments, a method of protecting germ cells reduces germ cell death induced by a chemotherapeutic agent by at least 1000%, 500%, at least 200%, at least 150%, at least 100%, at least 50%, at least 30%, at least 20%, at least 15%, at least 10%, or at least 5%, thereby protecting germ cells from cell death. In some embodiments, a method of protecting germ cells described herein increases the number of viable germ cell by at least 1000 fold, 500 fold, at least 200 fold, at least 150 fold, at least 100 fold, at least 50 fold, at least 30 fold, at least 20 fold, at least 15 fold, at least 10 fold, at least 5 fold, or by at least 2 fold, thereby protecting germ cells from chemotherapy-induced cell death. In some embodiments, a method of protecting germ cells described herein maintains the number of viable germ cells during or after a chemotherapeutic treatment within +/−50%, +/−40%, +/−30%, +/−20%, or +/−10% of the number of viable germ cells existing prior to a chemotherapeutic treatment, thereby protecting germ cells from a chemotherapeutic treatment (e.g., chemotherapy-induced cell death).

Administration of a chemotherapeutic agent to a subject can result in a decrease or reduction of fertility of a male or female subject. Administration of a chemotherapeutic agent to a subject can result in infertility of a male or female subject. In some embodiments, a composition or method herein inhibits a decrease or reduction of fertility in a subject caused by treatment with a chemotherapeutic agent.

In some embodiments, a composition or method herein inhibits a decrease or reduction of fertility in a subject caused by treatment with a chemotherapeutic agent. In some embodiments, a composition or method herein inhibits a chemotherapy-induced decrease or reduction of fertility by at least 1000%, 500%, at least 200%, at least 150%, at least 100%, at least 50%, at least 30%, at least 20%, at least 15%, at least 10%, or by at least 5%. In some embodiments, a composition or method herein substantially inhibits a chemotherapy-induced decrease or reduction of fertility where fertility in a chemotherapy treated subject is maintained within +/−50%, +/−40%, +/−30%, +/−20%, or +/−10% of the fertility of the subject as measured or estimated prior to a chemotherapy treatment. Methods of measuring or estimating fertility of a male or female subject are known in the art.

In certain embodiments a method, use or composition described herein reduces or inhibits germ cell suppression (e.g., suppression of proliferation) induced by a chemotherapeutic agent by at least 200%, at least 150%, at least 100%, at least 50%, at least 30%, at least 20%, at least 15%, at least 10%, or by at least 5%.

In some embodiments a method, use or composition described herein decreases germ cell suppression and/or death. In some embodiments a method, use or composition described herein decreases germ cell suppression or death induced by a chemotherapeutic agent. In some embodiments a method, use or composition described herein decreases germ cell death induced by a chemotherapeutic agent by up to 100%, up to 50%, up to 30%, up to 20%, up to 15%, up to 10%, or up to 5%. In certain embodiments a method, use or composition described herein decreases germ cell suppression (e.g., suppression of proliferation) induced by a chemotherapeutic agent by at least 200%, at least 150%, at least 100%, at least 50%, at least 30%, at least 20%, at least 15%, at least 10%, or by at least 5%.

In some embodiments a method, use or composition described herein promotes and/or increases maturation, proliferation and/or survival of germ cells in a subject. In some embodiments a method, use or composition described herein promotes and/or increases maturation, proliferation and/or survival of germ cells in a subject that was administered a chemotherapeutic agent. In some embodiments administration or delivery of humanin or a humanin analog promotes and/or increases maturation, proliferation and/or survival of germ cells in a subject that was administered a chemotherapeutic agent. In certain embodiments, administration of a chemotherapeutic agent (e.g., a cytotoxic compound) to a subject reduces, decreases, or inhibits maturation, proliferation and/or survival of germ cells in the absence of administration or delivery of humanin or humanin analog, which reduction, decrease or inhibition can be reversed completely or partially by administration of humanin or a humanin analog. In some embodiments a method, use or composition described herein promotes and/or increases maturation, proliferation and/or survival of germ cells by up to 200%, up to 100%, up to 50%, up to 30%, up to 20%, up to 15%, up to 10%, or up to 5%.

In some embodiments a method, use or composition described herein reduces, decreases or inhibits damage to germ cells in a subject. In some embodiments a method, use or composition described herein reduces, decreases or inhibits damage to germ cells in a subject that was administered or delivered a chemotherapeutic agent. In some embodiments administration or delivery of humanin or a humanin analog reduces, decreases or inhibits damage to germ cells in a subject that was administered a chemotherapeutic agent. In some embodiments a method, use or composition described herein reduces, decreases or inhibits damage to the genomic DNA, mitochondrial DNA, mitochondria, cell organelles or cell membranes of germ cells in a subject that was administered or delivered a chemotherapeutic agent.

In some embodiments a method, use or composition described herein enhances treatment of a hyperproliferative disorder. In some embodiments a method, use or composition described herein enhances treatment of a metastatic or non-metastatic neoplasia, tumor, cancer or malignancy in a subject. In certain embodiments a method of enhancing treatment of a hyperproliferative disorder (e.g., a metastatic or non-metastatic neoplasia, tumor, cancer or malignancy) in a subject, comprises administering to the subject a composition comprising humanin and/or one or more humanin analogs (e.g., a human polypeptide to tables 1-4). In certain embodiments a method of enhancing treatment of a hyperproliferative disorder (e.g., a metastatic or non-metastatic neoplasia, tumor, cancer or malignancy) in a subject, comprises administering to the subject a composition comprising a humanin polypeptide (e.g., humanin and/or a humanin analog) and a chemotherapeutic agent. The efficacy of a treatment for a hyperproliferative disorder can be determined by any suitable method. Non-limiting examples of determining the efficacy of a treatment include determining the a change, or lack thereof, in the number of hyperproliferative cells and/or number of tumors, the size of tumors or the size of a hyperproliferative tissue mass, the viability of hyperproliferative cells, cancer progression/infiltration, for example by methods of cancer staging, determining the presence or extent of metastasis, the like or combinations thereof. Enhancing a treatment often comprises enhancing (e.g., improving) the efficacy of a chemotherapeutic agent against a hyperproliferative disorder. In some embodiments the efficacy of a treatment that includes administration of a chemotherapeutic agent can be enhanced or improved by administering a humanin polypeptide prior to, concurrently with, or soon after administration of the chemotherapeutic agent. In some embodiments the activity of a chemotherapeutic agent against a hyperproliferative disorder can be increased by the presence of a humanin polypeptide. Therefore, in some embodiments the activity of a chemotherapeutic agent against a hyperproliferative disorder is increased by administering a humanin polypeptide prior to, concurrently with, or soon after administration of the chemotherapeutic agent.

In certain embodiments, a method, use or composition herein comprises humanin and/or a humanin analog (e.g., a humanin polypeptide). In certain embodiments, a method or use includes administering or delivery of humanin or a humanin analog to subject. Humanin or a humanin analog can be administered or delivered to a subject prior to, during or after administration of a chemotherapeutic agent. Humanin or a humanin analog can be administered to a subject prior to, during or after treatment with a chemotherapeutic agent. In certain embodiments humanin or a humanin analog is administered or used prior to, substantially contemporaneously with or following administration of a chemotherapeutic agent. In certain embodiments humanin or a humanin analog is administered or used in combination with a chemotherapeutic agent.

In some embodiments humanin or a humanin analog is administered or delivered in an amount sufficient to protect germ cells from the cytotoxic effects of a chemotherapeutic agent. In some embodiments humanin or a humanin analog is administered or delivered in an amount sufficient to protect germ cells in a subject from suppression or death induced, promoted, increased, or stimulated by a chemotherapeutic agent. In some embodiments humanin or a humanin analog is administered or delivered in an amount sufficient to promote or increase maturation, proliferation or survival of germ cells in a subject (e.g., a subject treated with a chemotherapeutic agent). In some embodiments humanin or a humanin analog is administered or delivered in an amount sufficient to increase germ cell counts in a subject (e.g., a subject treated with an autoimmune, anti-cancer or anti-tumor chemotherapeutic agent). Methods of determining germ cell counts are known in the art and any suitable method of determining germ cell counts can be used.

In some embodiments a composition comprising humanin and/or a humanin analog is administered or delivered in an amount sufficient to inhibit a chemotherapy-induced decrease or reduction of fertility. In some embodiments a composition comprising humanin and/or a humanin analog is administered or delivered in an amount sufficient to prevent a reduction or loss of fertility due to administration of a chemotherapeutic agent.

In some embodiments humanin or a humanin analog is administered or delivered in an amount sufficient to reduce, decrease, or inhibit damage of germ cells in a subject (e.g., a subject treated with a chemotherapeutic agent).

As disclosed herein, compositions, methods and uses of the invention, can be administered or delivered prior to, contemporaneously with or after a chemotherapeutic agent is administered or delivered, for example to a subject. Accordingly, methods, uses and compositions of the invention can be delivered prior to suppression or death of germ cells in order to protect germ cells. Compositions comprising humanin and/or one or more humanin analogs can be administered to a subject prophylactically.

Compositions, methods and uses, such as treatment methods and uses, can provide a detectable or measurable increase in germ cell counts, improved germ cell viability (e.g., decreased apoptosis or cell death), and/or germ cell function in a subject. Compositions, methods and uses of the invention therefore include providing a therapeutic benefit or improvement to a subject, for example, as reflected by increased, stabilized or a less profound reduction in germ cell counts induced or promoted by a chemotherapeutic agent, pathogenic agent and/or mechanical activity.

In some embodiments, a composition or method described herein enhances an anti-cancer effect of a chemotherapeutic agent in a subject. In some embodiments, the method comprises identifying or providing a subject having or suspected of having a hyperproliferative disorder and administering a composition to the subject, wherein the composition comprises one or more humanin polypeptides of tables 1-4. In some embodiments, the method comprises identifying or providing a subject that is, has been or will receive a chemotherapy for treatment of a hyperproliferative disorder and administering a composition to the subject, wherein the composition comprises one or more humanin polypeptides of tables 1-4. In some embodiments, a chemotherapeutic agent is administered to a subject prior to, during or after administering a composition comprising a humanin polypeptide. For example, in certain embodiments, a chemotherapeutic agent is administered to a subject up to 8 weeks, 1 week, 72 hr., 48 hr., 24 hr., 12 hr., 6 hr., 4 hr., 2 hr. or 1 hour before administering a composition comprising a humanin polypeptide. In certain embodiments, a chemotherapeutic agent is administered to a subject up to 60 minutes, 45 minutes, 30 minutes, 15 minutes, 10 minutes, or up to 5 minutes before administering a composition comprising a humanin polypeptide. In certain embodiments, a chemotherapeutic agent is administered to a subject during, substantially contemporaneously with, or concurrently with administering a composition comprising a humanin polypeptide. A chemotherapeutic agent may be administered by the same or separate route as a composition comprising a humanin polypeptide. A composition comprising a chemotherapeutic agent may comprise one or more humanin polypeptides. In some embodiments, a chemotherapeutic agent is administered to a subject within about 72, 48, 24, 12, 6, 4, 2 or within about 1 hour after a composition comprising a humanin polypeptide is administered. In some embodiments, a chemotherapeutic agent is administered to a subject within about 60 minutes, 45 minutes, 30 minutes, 15 minutes, 10 minutes, or within about 5 minutes after a composition comprising a humanin polypeptide is administered.

In some embodiments, a composition comprising a humanin polypeptide is administered in an amount sufficient to enhance the cytotoxic effects of a chemotherapeutic agent on a hyperproliferative tissue. A composition comprising a humanin polypeptide may comprise one or more different humanin polypeptides. A composition comprising a humanin polypeptide may comprise one or more humanin polypeptides of Tables 1-4. In some embodiments, a composition comprises one or more humanin polypeptides selected from SEQ ID NO:1, SEQ ID NO:2, HNG-F6A, HN-F6A, HN-S7A and HN-C8P. In some embodiments, a composition comprises or consists of a humanin polypeptide of SEQ ID NO:1, which composition may also include a pharmaceutical acceptable carrier, salt, buffer and/or excipient. In some embodiments, a composition comprises or consists of a humanin polypeptide of SEQ ID NO:2, which composition may also include a pharmaceutical acceptable carrier, salt, buffer and/or excipient.

A therapeutic benefit or improvement can be any measurable or detectable, objective or subjective, transient, temporary, or longer-term benefit to a subject or improvement in the response, disorder or disease, or one or more adverse symptoms, disorders, illnesses, pathologies, diseases, or complications caused by treatment with a chemotherapeutic agent (e.g., cytotoxic compound or chemotherapeutic agent) and/or associated with a disorder or disease, such as an infection Therapeutic benefits and improvements include, but are not limited to, decreasing, reducing, inhibiting, suppressing, limiting or controlling the occurrence, frequency, severity, progression, or duration of an adverse symptom of undesirable or aberrant response, disorder or disease, such as an infection.

Compositions, methods and uses of the invention, can be administered or delivered in a sufficient or effective amount to a subject. An "effective amount" or "sufficient amount" refers to an amount that provides, in single or multiple doses, alone or in combination, with one or more other compositions (e.g., chemotherapeutic agents or drugs), treatments, protocols, or therapeutic regimens, a detectable response of any duration of time (long or short term), an expected or desired outcome in or a benefit to a subject of any measurable or detectable degree or for any duration of time (e.g., for minutes, hours, days, months, years, or cured).

The doses of a "sufficient amount" for treatment (e.g., to provide a therapeutic benefit or improvement) typically are effective to provide a response (e.g., a measurable increase and/or stabilization) of germ cell viability, meiosis, growth, respiration, motility (e.g., sperm motility) and/or cell numbers, and/or an desired measure of fertility (e.g., preserving fertility, preventing a loss of fertility). In some embodiments a cell viability is assayed, for example, by a reduction in cell death (e.g., necrosis or apoptosis).

In some embodiments a sufficient amount humanin or a humanin analog comprises an amount between about 0.01 to 100 mg/Kg (mg of humanin or a humanin analog per Kg of a subjects body weight) per day, between about 0.05 to 50 mg/Kg per day, between about 0.1 to 25 mg/Kg per day, between about 0.5 to 15 mg/Kg per day, between about 0.5 to 15 mg/Kg per day, or between about 1.0 to 10 mg/Kg per day. In some embodiments administering a sufficient amount of humanin or a humanin analog comprises administered one or more dose amounts of between about 0.01 to 100 mg/Kg per day, between about 0.05 to 50 mg/Kg per day, between about 0.1 to 25 mg/Kg per day, between about 0.5 to 15 mg/Kg per day, between about 0.5 to 15 mg/Kg per day, or between about 1.0 to 10 mg/Kg per day. A sufficient amount of humanin or a humanin analog may be administered in 1, 2, 3, 4, 5, 6, or 7 doses per day. In some embodiments a sufficient amount of humanin or a humanin analog is administered continuously or intermittently by a patch or suitable device (e.g., a pump). A sufficient amount of humanin or a humanin analog may be self-administered by a subject. For example a subject may use, in one or more doses, a sufficient amount of humanin or a humanin analog.

An effective amount or a sufficient amount can, but need not be, provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the response, disorder, or disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol.

As is typical for treatment methods and uses, some subjects will exhibit a greater response, or less or no response to a given treatment method or use. An effective amount or a sufficient amount therefore need not be effective in each and every subject treated, prophylactically or therapeutically, nor a majority of treated subjects in a given group or population. An effective amount or a sufficient amount means effectiveness or sufficiency in a particular subject, not a group or the general population. Accordingly, appropriate amounts will depend upon the condition treated, the therapeutic effect desired, as well as the individual subject (e.g., the bioavailability within the subject, gender, age, etc.).

Effectiveness of a method or use, such as a method of treatment herein can provide a potential therapeutic benefit or improvement that can be ascertained by various methods. Such methods include, for example, measuring germ cell counts or viability, germ cell maturation or a response or activity of germ cells. Measuring T or B cell activation and/or differentiation, cell infiltration of a region, cell accumulation or migration to a region, production of antibodies, cytokines, lymphokines, chemokines, interferons and interleukins, cell growth and maturation factors using various immunological assays, such as ELISA, also can be used to ascertain effectiveness of a method, use or composition as set forth herein.

Humanin and/or humanin analogs, including in combinations with other agents or drugs, can be packaged in a suitable pharmaceutical formulation and/or dosage unit form for ease of administration and uniformity of dosage. "Dosage unit form" as used herein refers to physically discrete units suited as unitary dosages; each unit contains a quantity of the composition optionally in association with a carrier, excipient, diluent, or vehicle calculated to produce the desired treatment or therapeutic (e.g., beneficial) effect. The unit dosage forms can be varied according to factors including, but not necessarily limited to, the particular composition employed, the disorder or disease treated, the effect to be achieved, and the subject to be treated. Exemplary unit doses range from about 25-250, 250-500, 500-1,000, 1,000-2,500, 2,500-5,000, 5,000-25,000, or 5,000-50,000 pg; from about 50-500, 500-5,000, 5,000-25,000 or 25,000-50,000 ng; from about 50-500, 500-5,000, 5,000-25,000 or 25,000-50,000 rig; from about 25-250, 250-500, 500-1,000, 1,000-2,500, 2,500-5,000, 5,000-25,000, or 5,000-50,000 mg; and from about 1-5, 5-10, 10-25, 25-50, 50-100, 100-250, 250-500, 500-1,000, 1,000-2,500, or 2,500-5,000 grams.

As set forth herein, humanin and/or humanin analogs and compositions thereof may be contacted or provided in vitro, ex vivo or administered or delivered in vivo to a subject or patient in various doses and amounts, and frequencies. For example, a humanin and/or humanin analog or a composition thereof can be administered or delivered to provide the intended effect, as a single or as multiple dosages, for example, in an effective or sufficient amount.

Single or multiple (e.g., 2, 3, 4, 5, 6, 7, 8, 9, 10, or more times) administrations or doses can be administered on the same or consecutive days, alternating days or intermittently. For example, a humanin and/or humanin analog or a composition thereof can be administered one, two, three, four or more times daily, on alternating days, bi-weekly, weekly, monthly, bi-monthly, or annually. A humanin and/or humanin analog or composition thereof can be administered for any appropriate duration, for example, for period of 1 hour, or less, e.g., 30 minutes or less, 15 minutes or less, 5 minutes or less, or 1 minute, or less.

A humanin and/or humanin analog or composition thereof can be administered to a subject and methods and uses may be practiced prior to, substantially contemporaneously with, or within about 1-60 minutes, hours (e.g., within 1, 2, 3, 4, 5, 6, 8, 12, 24 hours), or days (1, 2, 3, 4, 5, 6, 7, 7-14, 14-21, 21-28, 28-45, 45-60, 60-90, etc.) of administration of a chemotherapeutic agent.

A humanin and/or humanin analog or composition thereof can be administered or delivered and methods and uses may be practiced via systemic, regional or local administration, by any route. For example, a humanin and/or humanin analog or composition thereof may be administered or delivered systemically, regionally or locally, via injection, infusion, orally (e.g., ingestion or inhalation), topically, intravenously, intra-arterially, intramuscularly, intraperitoneally, intradermally, subcutaneously, intracavity, intracranially, transdermally (topical), parenterally, e.g. transmucosally or intrarectally (enema) catheter, or optically. Humanin and/or humanin analog, compositions, methods and uses of the invention including pharmaceutical formulations may be administered via a (micro)encapsulated delivery system or packaged into an implant for administration.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in a formulation for administering or delivering a humanin and/or humanin analog or composition thereof to a subject.

Such compositions include solvents (aqueous or non aqueous), solutions (aqueous or non aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, saline, dextrose, fructose, ethanol, animal, vegetable or synthetic oils.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Carriers which may be used include petroleum jelly, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Appropriate pharmaceutical compositions and delivery systems are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

The invention provides kits comprising humanin and/or humanin analogs, combination compositions and pharmaceutical formulations thereof, packaged into suitable packaging material. A kit optionally includes a label or packaging insert including a description of the components or instructions for use in vitro, in vivo, or ex vivo, of the components therein. Exemplary instructions include instructions for a method, treatment protocol or therapeutic regimen. The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics (PK) and pharmacodynamics (PD). Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods or uses, treatment protocols or therapeutic regimes set forth herein. Kits of the invention therefore can additionally include labels or instructions for practicing any of the methods and uses of the invention described herein.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Kits can additionally include other components. Each component of the kit can be enclosed within an individual container and all of the various containers can be within a single package. Invention kits can be designed for cold storage.

EXAMPLES

The examples set forth below illustrate certain embodiments and do not limit the technology.

Example 1: Experiments 1-4, HN, HN Analogs and Effects of HN and Analogs on Germ Cell Apoptosis Induced by Chemotherapeutic Drugs Humanin (HN), a 24-amino acid mitochondrial derived peptide, is an endogenous anti-apoptotic peptide in many tissues including the testis. Experiments were performed herein to explore the application of HN and its analogs as cytoprotective agents for protecting germ cells from chemotherapy-induced apoptosis (e.g., for fertility preservation). Studies were also performed to determine the ability of HN and its analogs to alter the effects of chemotherapeutic agents against cancer cells.

As disclosed herein, it was determined that HN has cytoprotective effects on two chemotherapeutic agents in two models: doxorubicin (DOX) to induce germ cell apoptosis in ex vivo seminiferous tubule cultures (Experiment 1) and CP in vivo treatment in adult mice (Experiment 2). Accordingly, HN is an effective protector of germ cell death in mice treated with chemotherapy and thus is a protector against chemotherapy induced infertility.

A potent humanin analog HNG was used with or without chemotherapeutic agent CP in a mouse melanoma lung metastasis model (Collisson, et al., 2003; Craft, et al., 2005) (Experiment 3 and 4). The synthetic HN analog, HNG, has a substitution of glycine for serine at position 14 (HNG-S14G) in the 24 amino acid sequence of HN, which enhances its cytoprotective activity (Hashimoto, et al., 2001).

Moreover, HN and its analogs HNG can be an effective adjunct to established chemotherapy to markedly enhance the anti-cancer effects of chemotherapy treatment of a metastatic melanoma mouse model. These discoveries indicate clinical relevance to markedly enhance treatment of cancer and at the same time protect the cured patient against treatment induced infertility.

Whether HN would prevent chemotherapy-induced germ cell apoptosis was investigated. Segments of seminiferous tubules isolated from adult mouse testis ex vivo were treated with either HN, doxorubicin (DOX) or HN+DOX for 12 hours. Young adult mice in vivo were treated with intraperitoneal (IP) injection of HN, cyclophosphamide (CP), or the combination. Humanin significantly reduced germ cell apoptosis in mice induced by DOX in seminiferous tubule cultures ex vivo and by CP in mice in vivo (both $p<0.05$). These data showed that HN reduces chemotherapy-induced germ cell apoptosis in mice. In some embodiments, synthetic HN or its analogs may reduce chemotherapy-induced cancer cell death while protecting germ cells from apoptosis. To verify this, a potent HN analog HNG (HN-S14G) was used with or without CP in a mouse melanoma with lung metastasis model. Five mice were used as control and 20 mice were inoculated intravenously with B16 murine melanoma cells. Of these mice five received no further treatment. A week later the remaining 15 mice (n=5 per group) were treated for additional 2 weeks with: 1) HNG daily IP injection for 2 weeks; 2) a single CP IP injection; 3) combined CP with HNG. All mice were sacrificed 3 weeks after tumor inoculation. Non-treated tumor-bearing mice had increased germ cells apoptosis when compared with control (p=0.001). CP treatment significantly increased germ cell apoptosis (P<0.001) in comparison with control and HNG treated mice. HNG treatment for 2 weeks attenuated CP induced germ cell apoptosis (p<0.001). While HNG treatment decreased the number of metastatic tumors in the lungs, CP treatment not only decreased number of tumors (p=0.006) but also regressed tumor size when compared with non-treated tumor-bearing mice. Importantly, combined HNG and CP treatment significantly decreased number of tumors (p<0.001) and led to more to differentiated melanin producing cells compared to CP treatment alone. This indicates that 1) HNG protects male germ cells from apoptosis induced by CP treatment; 2) HNG enhances the suppressive effects of CP on metastatic lung melanoma in mice and markedly increase number of differentiated melanoma cells compared to CP alone. The long term effects and the mechanisms of action of HNG on male fertility preservation and the regression of cancer progression will be determined in future planned experiments.

Materials and Methods

Animals

Adult male C57BL/6J (25 to 30 g) mice were obtained from Jackson Laboratory (Bar Harbor, Me.) and housed at the accredited animal facilities at Los Angeles Biomedical Research Institute. The mice had unlimited access to food and water and were provided housing at normal light-dark cycles (12 hr. each) at a constant temperature of 22° C. Animal handling, experimentation, and killing of the animals were in accordance with the recommendation of the American Veterinary Medical Association and were approved by the Animal Care and Use Review Committee of Los Angeles Biomedical Research Institute at Harbor-UCLA Medical Center.

Materials

HN and HNG were synthesized by CPC Scientific (Sunnyvale, Calif.), and DOX (doxorubicin hydrochloride) and CP (cyclophosphamide monohydrate) were obtained from Sigma Aldrich (St. Louis, Mo.).

Experimental Design and Procedures

Experiment 1: The Effects of HN on DOX-Induced Germ Cell Apoptosis in Mouse Seminiferous Tubule Cultures Ex Vivo A total of 15 young adult (12-13 week-old) mice were used for these ex vivo studies. The animals were sacrificed with a 5% pentobarbital (200 mg/Kg) IP injection. Testes were dissected and after removing the tunica albuginea, seminiferous tubules isolated from testes were cut into small segments under a dissecting microscope and light and dark segments were separated by dissection. Ten to twelve segments were placed (2 mm in length) in each well on a six well plate with 2 ml serum free Ham F-10 culture medium (GIBCO, Life Technologies, Thermo Fisher Scientific Corp., Carlsbad, Calif.) with the following treatments: control (Con, n=10), heat (43° C., 15 minutes, used as a positive control, n=10); HN 10 µg/mL (n=9); DOX 10 mcM (Dox10, n=10); and DOX 10 mcM+Humanin 10 µg/mL (Dox10+HN, n=10). For these experiments, n represents the total number of times the treatment was repeated using different animals. After 12 hours of incubation at 34° C. the seminiferous tubules from each treatment group were used to make "squashed" seminiferous tubule samples on a slide for TUNEL (TdT-mediated dUTP nick-end labeling) assay to detect germ cell apoptosis (Erkkila, et al., 1997; Toppari & Parvinen, 1985). To quantify the rate of germ cell apoptosis under a light microscope at 400× magnification, a square grid fitted within the eyepiece provided a reference area of 62,500 µm². The TUNEL positive apoptotic germ cells within the frame of grid were counted in 4 segments of seminiferous tubules in each group. The incidence of germ cell apoptosis was expressed as the number of apoptotic germ cells per mm².

Experiment 2: The In Vivo Effects of HN on CP Induced Male Germ Cell Apoptosis in Mice Young adult mice (12-13 weeks) were randomly divided into 4 groups with 4 or 5 mice per group and received an IP injection: control (Con) (saline), HN (40 mg/Kg BW), CP (200 mg/Kg BW), and the combination of CP+HN. These experiments were repeated four times. In the CP+HN group, mice received an injection of HN followed by an injection of CP about 15 minutes later. Twenty-four hours after injections animals were sacrificed using 5% pentobarbital (200 mg/kg BW) IP injection. Blood was collected and one testis was removed, weighed and frozen in liquid nitrogen. The mouse was next perfused with saline and then subsequently perfuse-fixed with Bouin's solution as previously described and apoptosis was assessed by TUNEL assay (Lue, et al., 2009).

Experiment 3: Effect of HNG on CP-Induced Germ Cell Apoptosis and Metastatic Lung Tumor Regression in a Mouse B16 Melanoma Model.

A total of 25 young adult mice (10-12 weeks) were randomly divided into 5 groups (n=5 per group). Five mice were used as control. Twenty mice were inoculated intravenously with B16 murine melanoma cells ($2 \times 10^5$ cells/mouse). Among these 20 tumor-inoculated mice, 5 mice received no further treatment. After one week, the remaining 15 mice were divided into 3 groups and injected with: 1) HNG daily IP (5 mg/Kg body weight) for 2 weeks; 2) CP (200 mg/Kg body weight IP single injection); 3) combined CP with HNG treatment (same doses as above). All mice were sacrificed 3 weeks after tumor inoculation, and 2 weeks after HNG and/or CP treatment. The animals were sacrificed with 5% pentobarbital (200 mg/kg body weight) IP injection after which blood was collected from the right atrium of the heart. One of the testes from each mouse was immersed fixed in Bouin's solution, and the mice were perfused with saline and subsequently perfuse-fixed with 5% glutaraldehyde in 0.05 M cacodylate buffer (pH 7.4). The lungs were dissected out and post fixed in 5% glutaraldehyde solution for 24 hours and stored in cacodylate buffer at 4° C. for the subsequent tumor count (Lue, et al., 2010; Lue, et al., 2009).

Experiment 4: Effect of Higher Doses of HNG on CP-Induced Germ Cell Death and Enhancement of CP in Suppressing Tumor Growth Experiment 3 was repeated after inoculation of B16 melanoma tumor at week 1 and then treated with the following treatment starting at week 2 (n=5 mice per group): 1). No treatment; 2). HNG IP injections 5 mg/Kg daily; 3) CP 200 mg/Kg single IP injection; 4) HNG 5 mg/Kg/day+CP; 5). HNG IP injections 15 mg/Kg daily; and 6). HNG 15 mg/Kg/day+CP. All animals were euthanized and perfused with 4% paraformaldehyde at the end of week 3. Lungs and testes were collected and processed as in experiment 3.

Methods

For detection of apoptosis in testicular sections, the paraffin embedded testis tissue was cut into 5 micron sections and stained with the TdT-mediated dUTP nick-end labeling assay (TUNEL Apoptosis Detection Kit, Millipore, Billerica, Mass.) to detect apoptosis of germ cells in the testis (Lue, et al., 2009). Testicular sections assayed by TUNEL were examined under a light microscope and the apoptotic germ cells were blindly and manually counted. The seminiferous tubules in the testis section under the microscope were grouped as stages IX-IV (early-late stages of spermatogenesis) and V-VIII (middle stages of spermatogenesis). Germ cell apoptosis was quantified as the number of seminiferous tubules containing apoptotic spermatogonia, spermatoctyes, round spermatids and spermatozoa per 100 seminiferous tubules (Drumond, et al., 2011).

B16 melanoma tumors in the lung were quantified by counting the number of tumors on the surface of the lungs under stereomicroscopy (Collisson, et al., 2003; Craft, et al., 2005). The size of the tumor was measured using histomorphometry and expressed as average size of tumor. The appearance of the melanoma cells were reviewed and characterized by an expert pathologist.

Statistical Analysis

Statistical analyses of the majority of the data was performed using the Sigma Plot 12 program (Jandel, San Rafael, Calif.). The data were analyzed by using t-tests and one-way ANOVA followed by Student-Newman-Keuls Method. P-values of less than 0.05 (P<0.05) were considered significant. In in vivo experiments when the testicular sections were assessed for apoptosis, a mixed model used the percentage of tubules with apoptosis as the dependent variable. Two different stages (Early or Late Vs Middle) and four treatment groups (Control, HN CP, CP+HN) as well as the interaction term were included in the model as independent variables. Persons who did the experiment were considered as a random effect to accommodate a potential heterogeneous variance in the model. Least Square Means and their differences were computed and tested using the Tukey's adjustment for multiple pair-wise comparisons. A residual analysis was done to check for the model assumptions. All the data analysis was carried out using SAS 9.3 (Cary, N.C. USA).

Results

Experiment 1 Results: Effect of Doxorubicin on Germ Cell Apoptosis in Ex Vivo Seminiferous Tubule Cultures It was indicated in short term (12 hours) ex vivo seminiferous tubule cultures that HN (10 µg/mL) treatment alone had no effect on germ cell apoptosis when compared with control. As expected, heat exposure serving as a positive control (43° C., 15 minutes), significantly increased the rate of apoptosis compare to control and HN treated groups (p<0.05). Addition of DOX at 10 micromole induced a significantly higher number of apoptotic germ cells when compared to control and HN treated groups (p<0.05) (FIG. 1). Treatment with HN (10 µg/ml) significantly reduced the number of apoptotic germ cells induced by DOX treatment (p<0.05) (FIG. 1).

Experiment 2 Results: Effect of HN on CP-Induced Germ Cell Apoptosis In Vitro

Figure 2B:
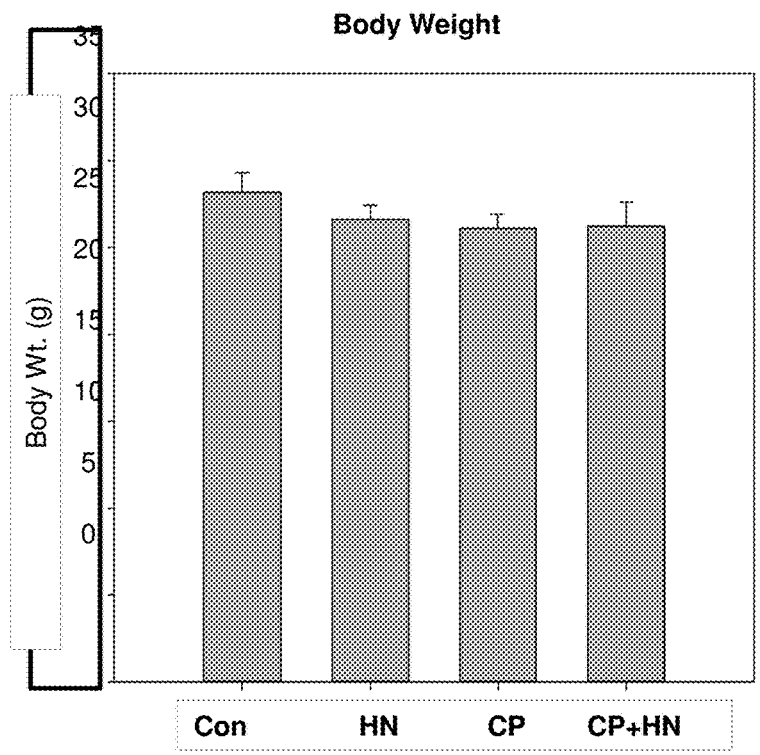
FIGS. 2A-2B show a histogram of body weight (FIG. 2A, x-axis, grams (g)) and testis weight (FIG. 2B, y-axis, grams (g)) of mice 24 hours after receiving no treatment (Con, control), HN 40 mg/Kg IP alone (HN), cyclophosphamide (200 mg/Kg IP) alone (CP), or cyclophosphamide and Humanin (CP+HN).
Figure 2A:
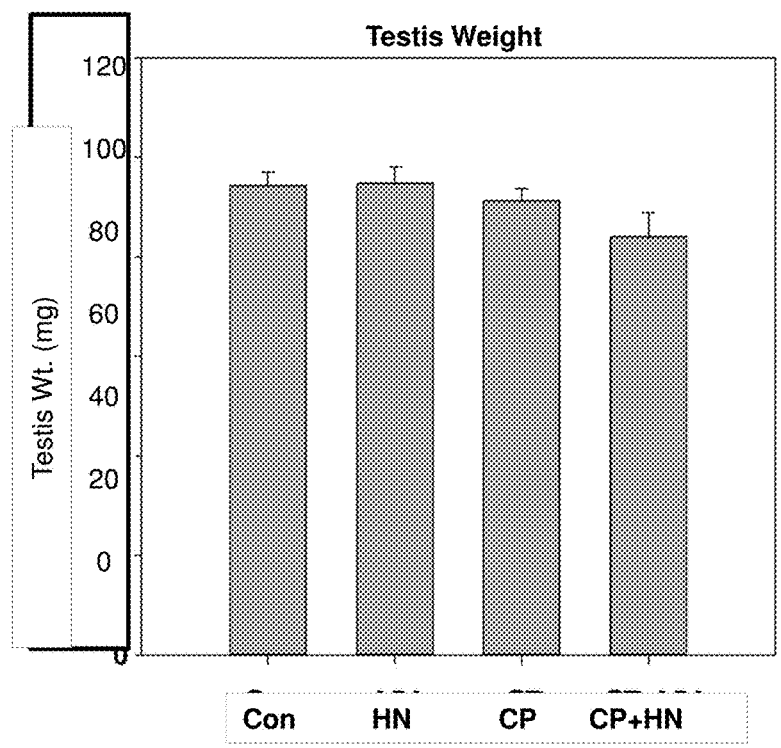
Figure 3:
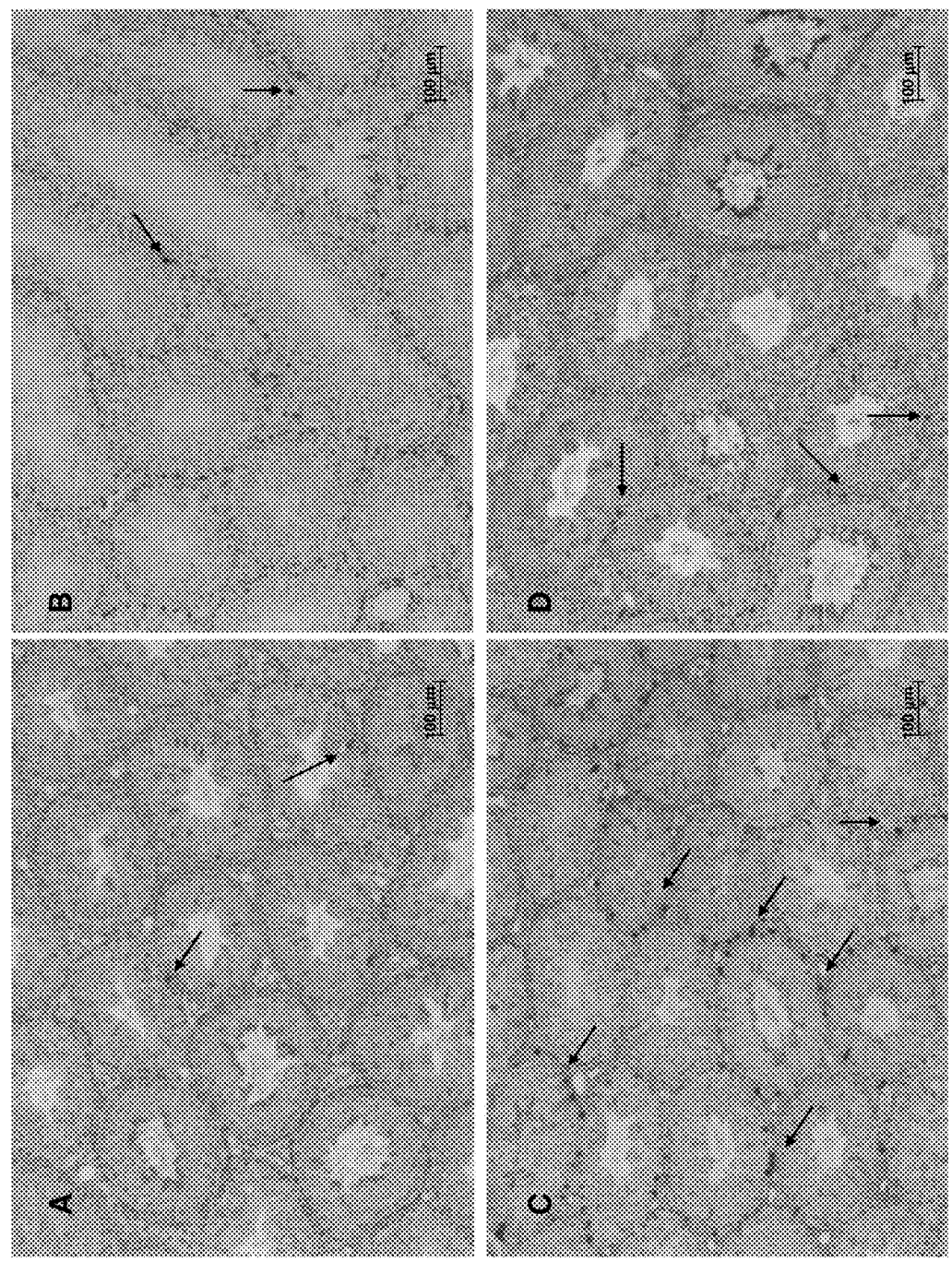
FIGS. 3A-3D show micrograph images of apoptotic cells stained by Terminal deoxynucleotidyl transferase dUTP nick end labeling (TUNEL), a method for detecting DNA fragmentation by labeling the terminal end of nucleic acids. TUNEL positive cells (dark grey or brown in color, arrows) are shown in testis of control treated (FIG. 3A), HN treated (FIG. 3B), cyclophosphamide (CP) treated (FIG. 3C), and combined HN and cyclophosphamide treated mice (FIG. 3D). Scale bar, 100 μm.

In experiment 2, the body and testis weights of mice from the 4 experimental groups were not significantly different 24 hours after treatment (FIG. 2). As shown in the testicular cross sections stained with TUNEL (FIG. 3), compared to the control group (FIG. 3A), HN (40 mg/Kg, IP single injection) alone (FIG. 3B) had no significant effect on germ cell apoptosis. CP treatment (FIG. 3C) significantly increased germ cell apoptosis. HN treatment attenuated the CP-induced germ cell apoptosis (FIG. 3D). Examination of the effect of HN on stage-specific germ cell apoptosis showed that in early-late stages of spermatogenesis (Stages XI-IV) (FIG. 4), CP treatment significantly increased germ cell apoptosis compared to control (p=0.003) and HN (p–0.003) (FIG. 4). The CP-induced apoptosis was ameliorated by concomitant treatment with HN (CP+HN, p<0.033) but not to the extent of apoptosis observed in control (p=0.052) and HN (p=0.046) treated mice (FIG. 4E). In the middle stages (V-VIII, FIG. 5) stages of spermatogenesis CP induced significant increase in apoptosis compared to control (p=0.002) and HN (p=0.003) groups. The CP-induced apoptosis in the middle stages was not significantly decreased by concomitant treatment with HN (CP+HN, p=0.29) and CP+HN remained higher than control (p=0.006) and HN (p=0.008) treated mice (FIG. 5E).

Figure 6A:
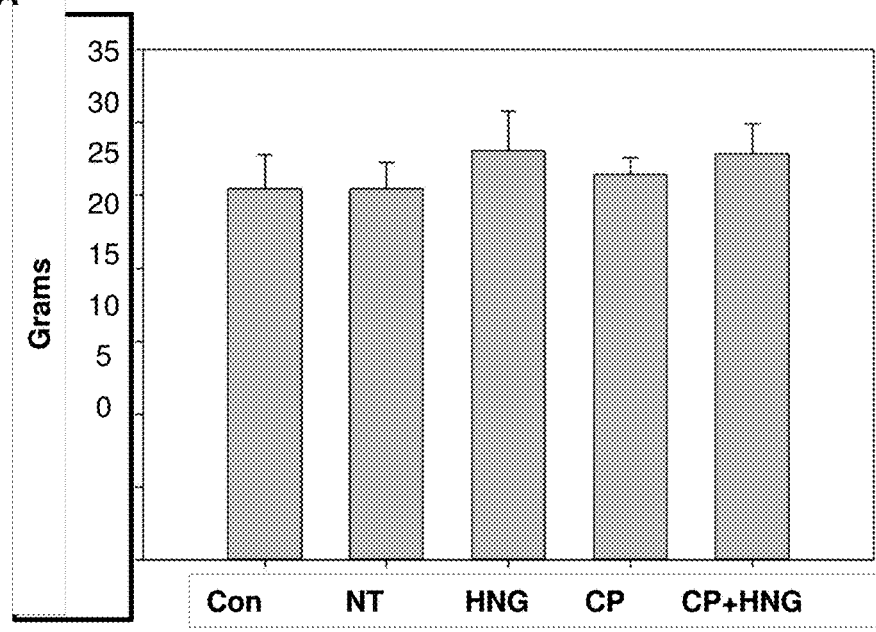
FIGS. 6A-6B show a histogram of mean body weight (y-axis) of control mice (FIG. 6A) and mice receiving a tail vein injection of B16 mouse melanoma cells (FIG. 6B). Body weights were measured 3 weeks after injection. Two weeks before measuring the body weights, mice were treated with a humanin analog (HNG), cyclophosphamide (CP) or HNG and cyclophosphamide (CP+HNG) or received no treatment (NT). Means with unlike superscripts (e.g., a and b as shown above the histograms) are significantly different (P<0.05).
Figure 6B:
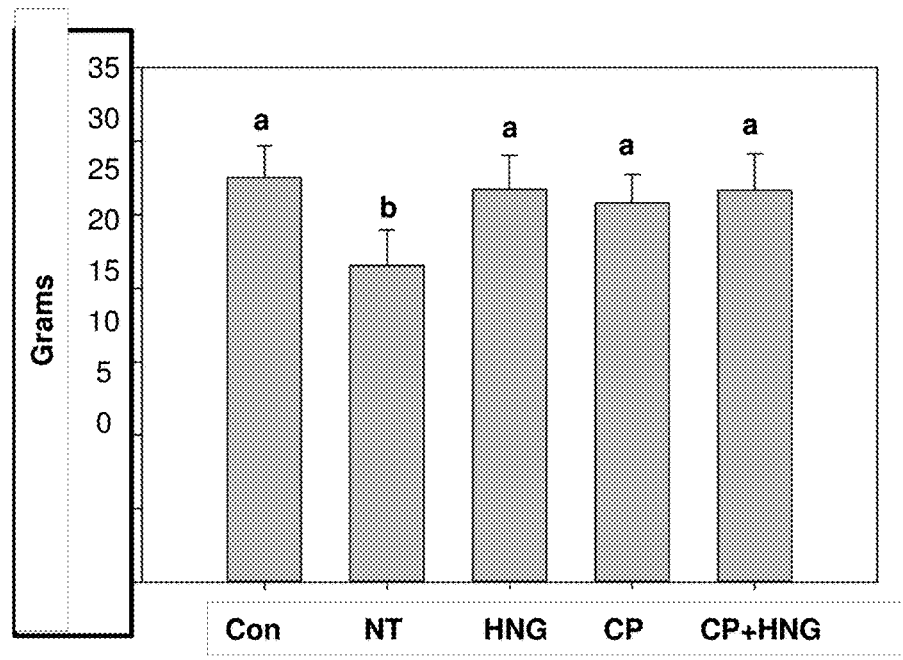
Figure 7:
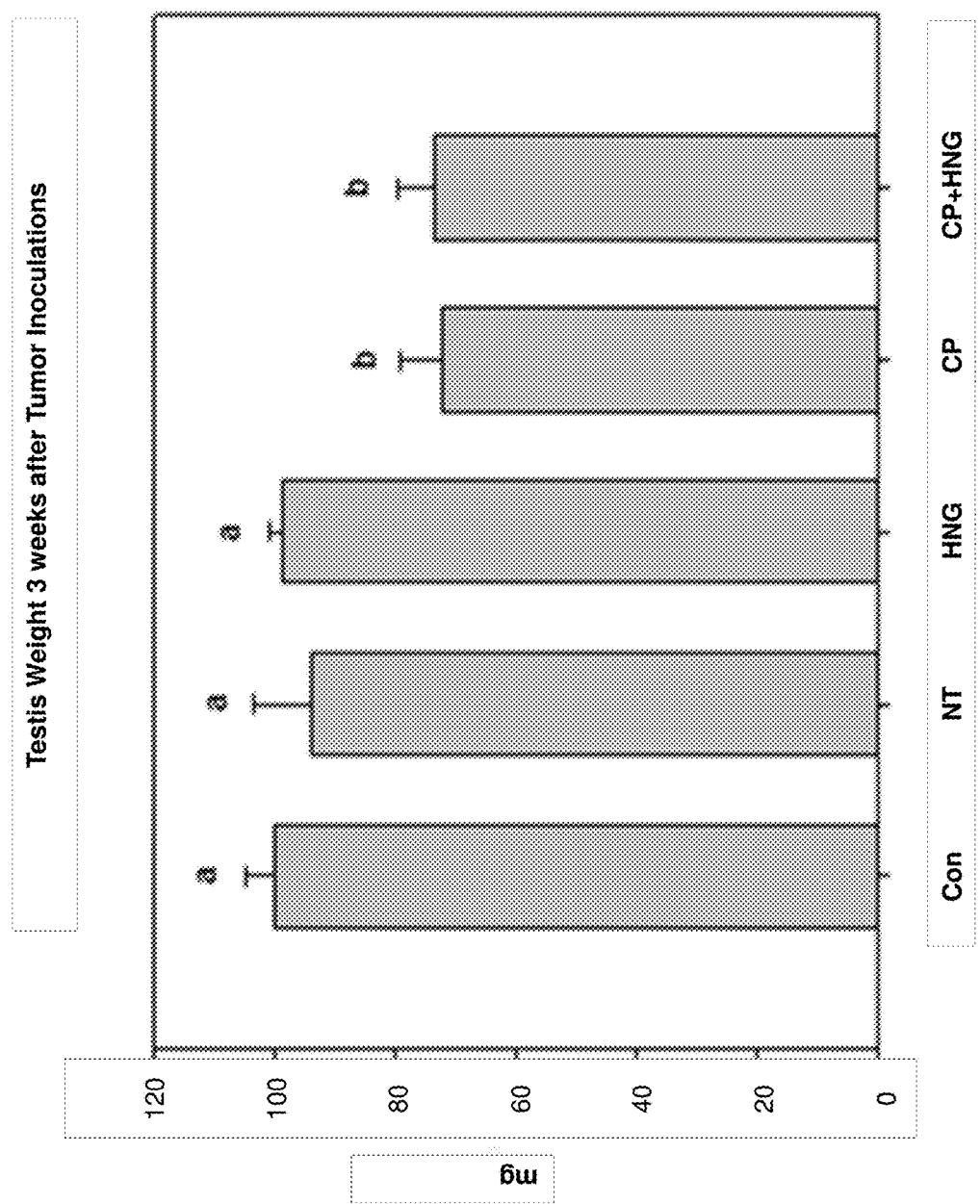
FIG. 7 shows a histogram of testis weight (y-axis) of mice receiving a tail vein injection of B16 mouse melanoma cells. Testis weights were measured 3 weeks after injection. Two weeks before measuring the testis weights, mice were treated with HNG (HNG), cyclophosphamide (CP) or HNG and cyclophosphamide (CP+HNG), or received no treatment (NT). Means with unlike superscripts (e.g., a and b as shown above the histograms) are significantly different (P<0.05).
Figure 8:
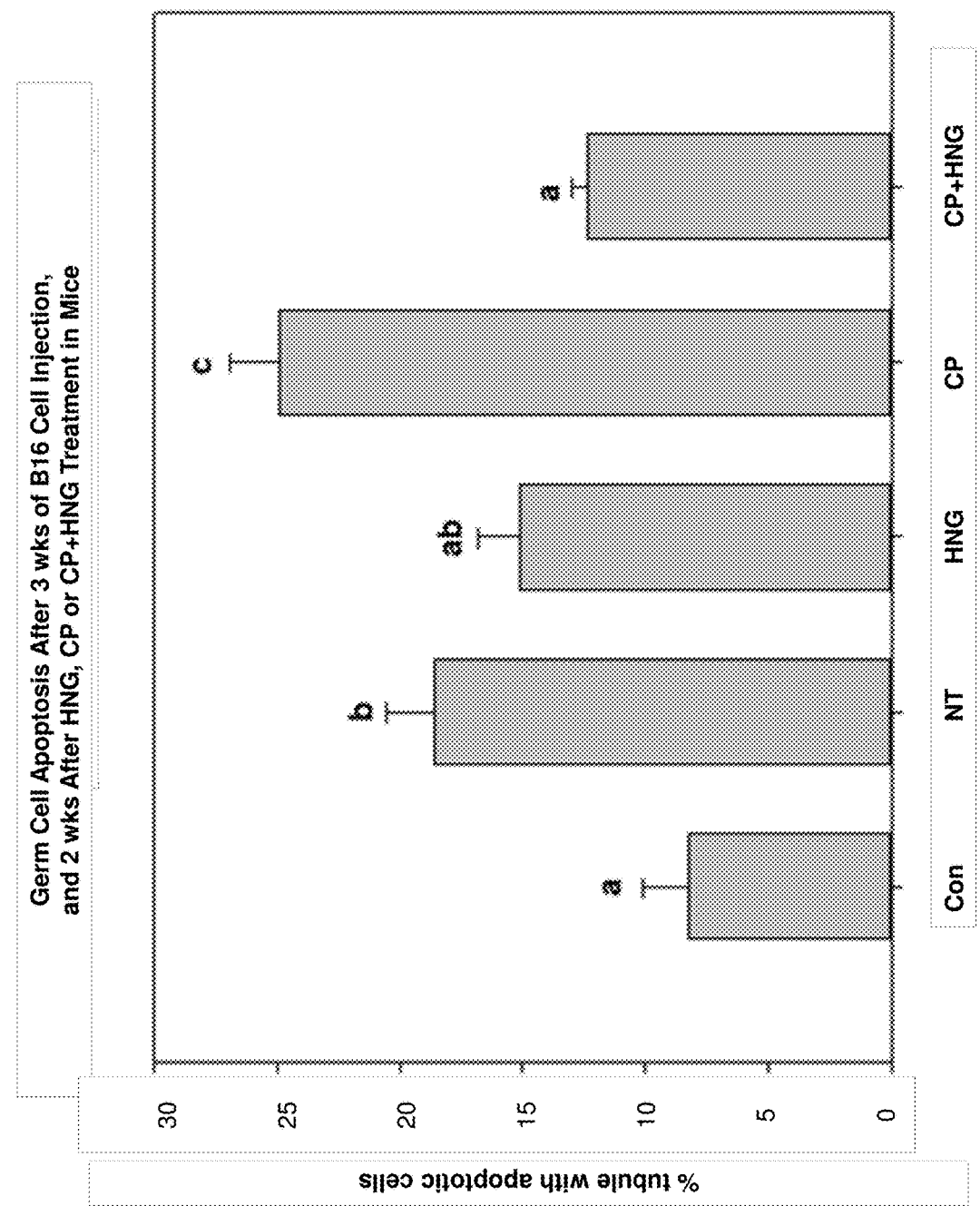
FIG. 8 shows a histogram of germ cell apoptosis of mice receiving a tail vein injection of B16 mouse melanoma cells. Germ cell apoptosis was measured 3 weeks after injection. Two weeks before measuring germ cell apoptosis, mice were treated with HNG (HNG), cyclophosphamide (CP) or HNG and cyclophosphamide (CP+HNG), or received no treatment (NT). Germ cell apoptosis is expressed as the percent of seminiferous tubules containing apoptotic germ cells (y-axis). Means with unlike superscripts (e.g., a, b, c and ab, as shown above the histograms) are significantly different (P<0.05).

Experiment 3 Results: Effect of HNG on CP Induced Germ Cell Apoptosis and Metastatic Lung Tumor Regression in a Mouse B16 Melanoma Model The mean body weight was similar in the five groups of mice before B16 mouse melanoma cell injection into the tail vein (FIG. 6A). Three weeks after tumor inoculation, mice that were not treated had significantly lower body weight when compared with control, HNG alone, CP alone and HNG+CP treated mice (FIG. 6B). CP treatment for 2 weeks significantly decreased the testis weight in comparison with control, non-treated tumor bearing, and HNG treated mice (FIG. 7). Addition of HNG to CP treatment failed to restore the testis weight to the control, non-treated, and HN treated groups (FIG. 7). Non-treated mice with metastatic melanoma had increased germ cells apoptosis when compared with control (FIG. 8). CP treatment further significantly increased germ cell apoptosis (P<0.001) when compared to control and HNG treated mice. Daily HNG treatment for 2 weeks significantly (p<0.001) attenuated CP-induced germ cell apoptosis (FIG. 8).

Figure 9:
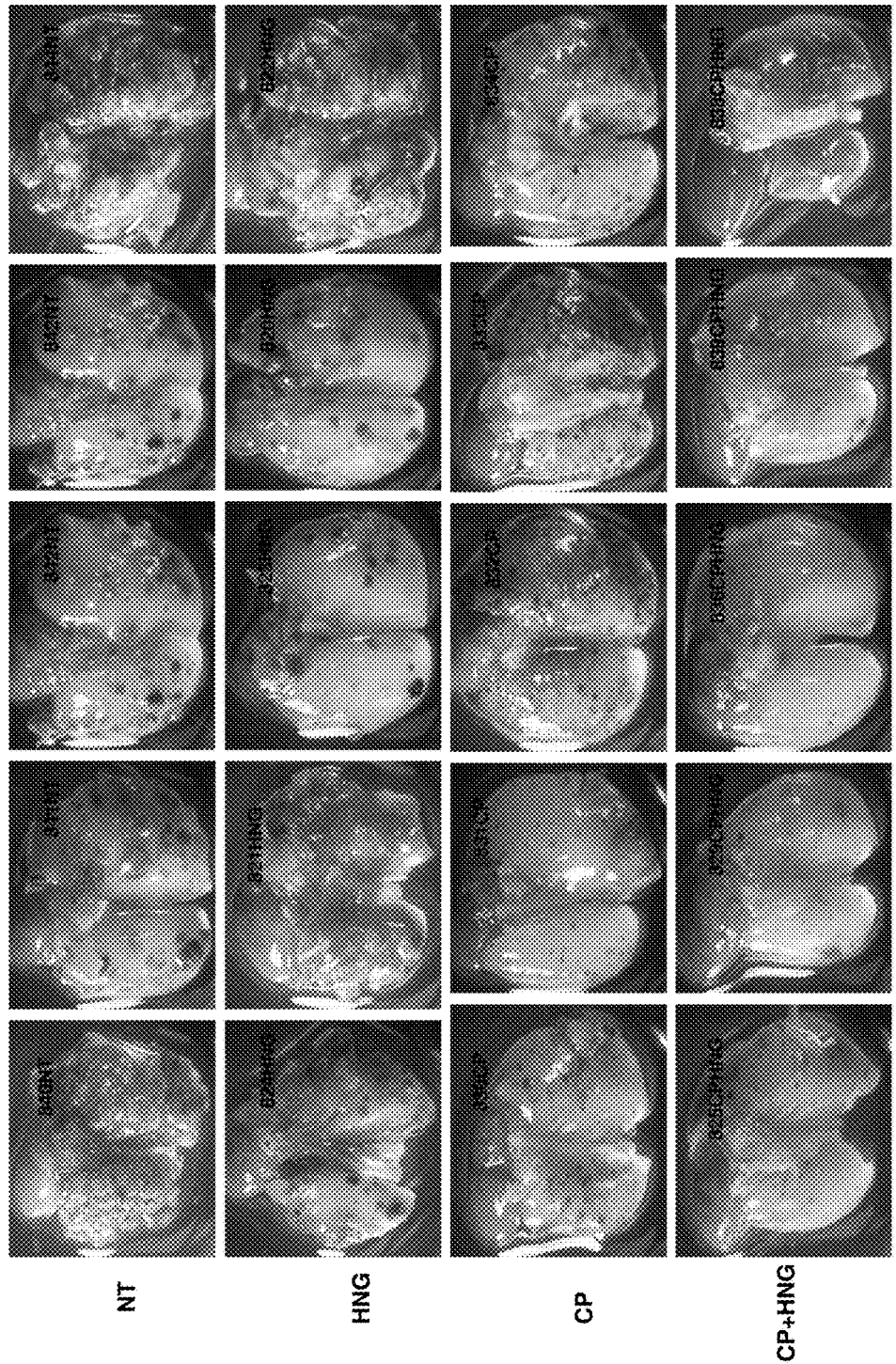
FIG. 9. shows micrograph images of metastatic lung melanomas in testis of mice receiving a tail vein injection of B16 mouse melanoma cells. Testis were harvested from mice receiving no-treatment (Row NT, images 840NT, 841 NT, 842NT, 843NT, 844NT) or mice treated with HNG (Row HNG, images 824HNG, 821 HNG, 823HNG, 820HNG, 822HNG), cyclophosphamide (Row CP, images 830CP, 831CP, 832CP, 833CP, 834CP) or HNG and cyclophosphamide (Row CP+HNG, 825CPHNG, 829CPHNG, 836CPHNG, 839CPHNG, 838CPHNG).
Figure 10:
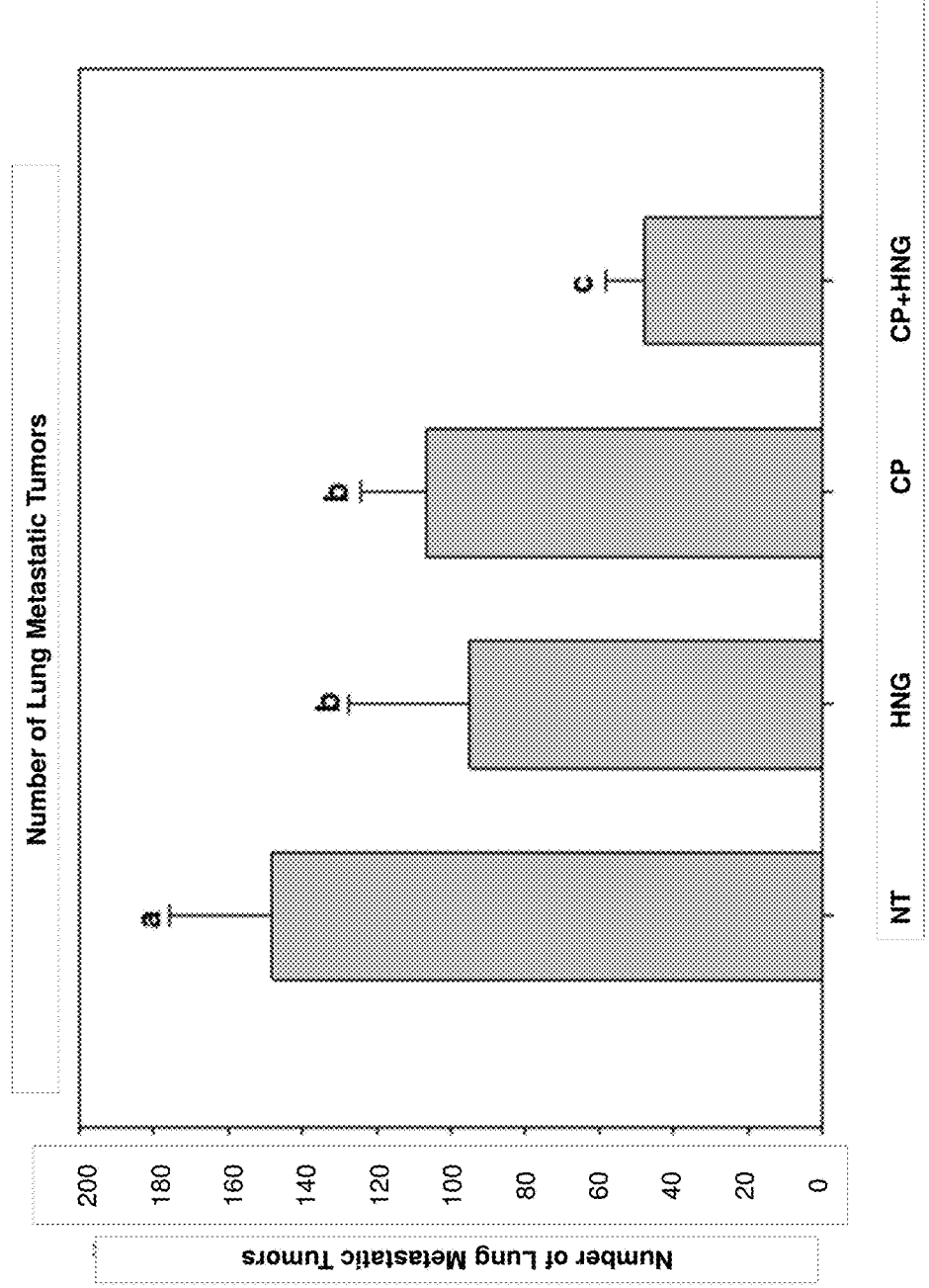
FIG. 10 shows a histogram of the number of lung metastatic tumors (y-axis) in mice receiving a tail vein injection of B16 mouse melanoma cells. The number of lung metastatic tumors were counted 3 weeks after injection. Two weeks before counting, mice were treated with HNG (HNG), cyclophosphamide (CP) or HNG and cyclophosphamide (CP+HNG), or received no treatment (NT). Means with unlike superscripts (e.g., a, b and c, as shown above the histograms) are significantly different (P<0.05).

The lungs were examined and the number of metastatic tumors on the surface of the lungs was quantified (FIG. 9). HNG treatment alone appeared to decrease the number of tumors but appeared to have no effect on the size of the melanoma metastasis on the surface of the lungs. On the other hand, CP treatment not only significantly (p=0.006) decreased number of tumors but also tumor size as compared with non-treated tumor-bearing mice (FIG. 9, row CP and FIG. 10). Importantly, addition of HNG to CP treatment significantly (p<0.001) (FIG. 9. row CP+HNG and FIG. 10) decreased the number of tumors as compared to CP treatment alone (FIG. 9, row CP). Tumor size was assessed by histomorphometry.

Experiment 4

Figure 11:
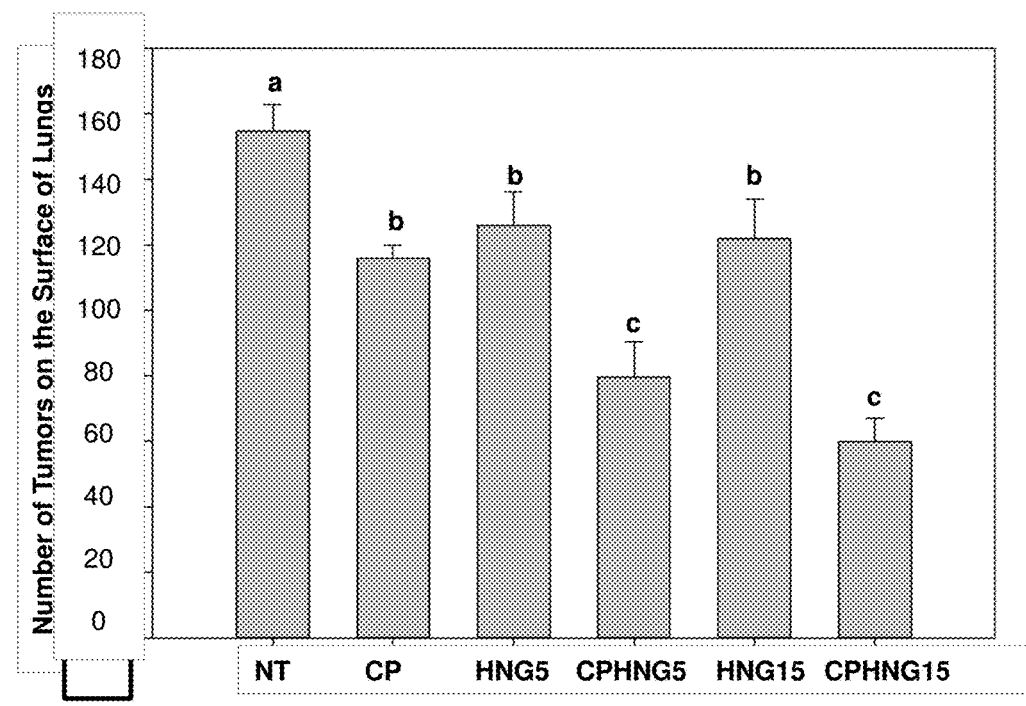
FIG. 11 shows a histogram of the number of lung metastatic tumors on the surface of lungs (y-axis) in mice receiving a tail vein injection of B16 mouse melanoma cells. The number of lung metastatic tumors were counted 3 weeks after injection. Two weeks before counting, mice were treated with 5 mg/kg HNG (HNG5), 15 mg/kg HNG (HNG15), cyclophosphamide (CP), 5 mg/kg HNG and cyclophosphamide (CPHNG5), 15 mg/kg HNG and cyclophosphamide (CPHNG15), or received no treatment (NT). Means with unlike superscripts (e.g., a, b and c, as shown above the histograms) are significantly different (P<0.05).
Figure 12:
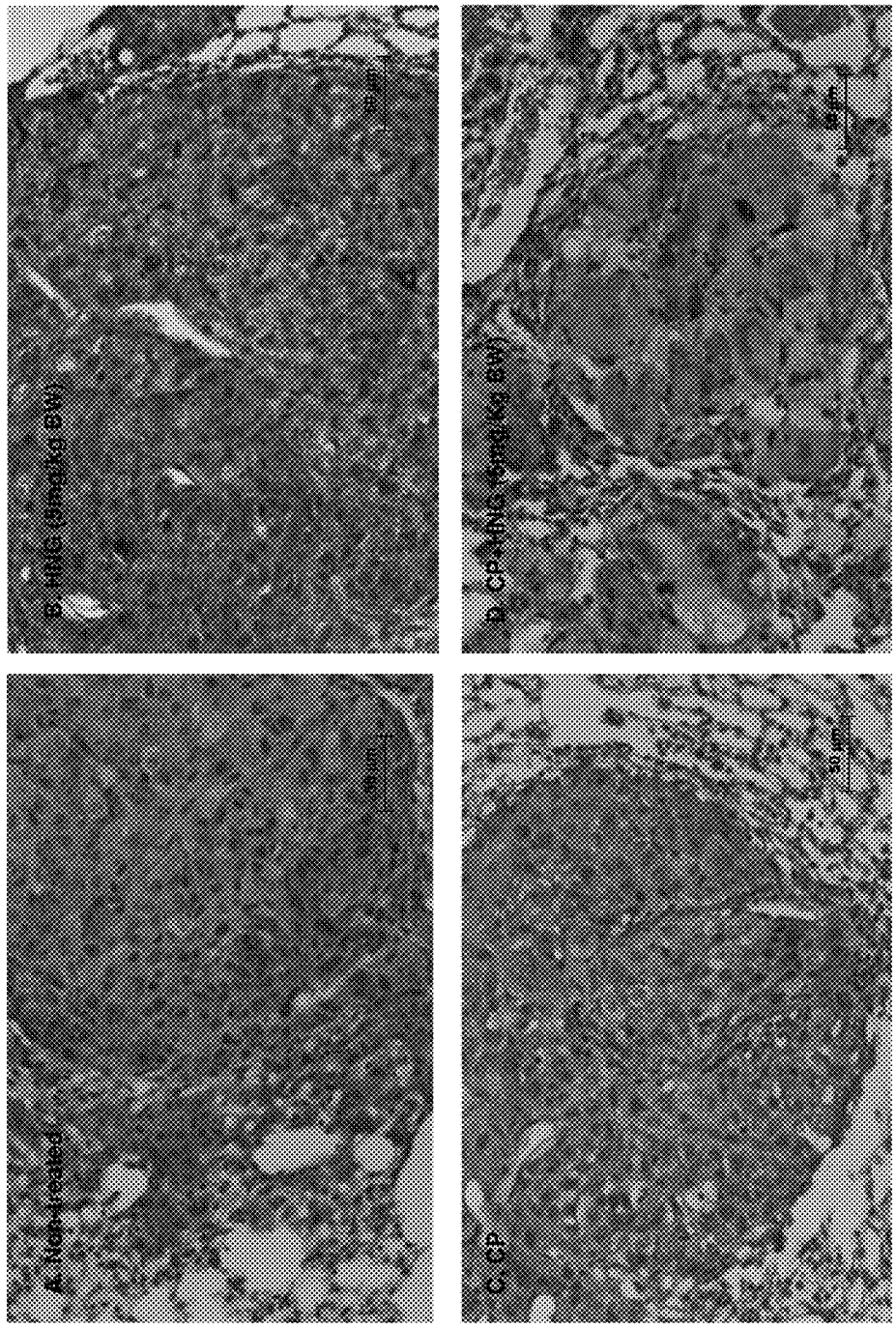
FIGS. 12A-12D show micrograph images of the lung metastatic melanoma histology in non-treated (FIG. 12A), HNG (5 mg/kg BW) alone (FIG. 12B), CP alone (FIG. 12C) and CP+HNG (FIG. 12D) treated mice. In the untreated mice, the undifferentiated melanoma cells were small with mitotic figures (FIG. 12A); HNG treatment alone did not change the histology of the melanoma cells (FIG. 12B); CP treatment induced minor differentiation of melanoma cells with more cytoplasm (FIG. 12C); and CP+HN treatment resulted marked increase in large differentiated cells with abundant cytoplasm and presence of melanin in some of these large cells (FIG. 12D).

Using the same methods as Experiment 3, the number of tumors on the surface of lungs of mice treated with saline as non-treated control were counted, CP alone, HNG (5 mg/Kg BW), HNG (5 mg/Kg BW)+CP, HNG (15 mg/Kg BW), and HNG (15 mg/kg BW)+CP. All animals were sacrificed 3 weeks after B16 Cell Injection, and 2 weeks after HNG, CP or CP+HNG treatment. As demonstrated in FIG. 11, HNG at both 5 mg/kg BW (p=0.0043) and 15 mg/kg BW (p=0.0029) doses significantly decreased the number of lung tumors but not size of the tumors when compared with non-treated tumor-bearing mice. CP significantly decreased both the number and size of the tumors compared to controls (p=0.013). HNG at both 5 mg/Kg BW and 15 mg/Kg BW when added concomitantly with CP significantly decreased the number of tumors than either treatment alone (P=0.001). The assessment of lung tumor area and testicular germ cell apoptosis is being assessed in the laboratory using histomorphometry. Histological examination of the metastatic lung tumor cells showed that CP decreased the number of metastatic melanoma cells, whereas HNG was added to the CP treatment resulted in much more differentiation of the metastatic lung tumor cells when compared to CP treatment alone (FIG. 12).

Discussion

Chemotherapeutic agents in combination can be very effective in treatment of leukemia, lymphoma, testicular cancers, brain tumors and melanoma. These cancers occur commonly in young men. Preservation of fertility in young patients with cancer after chemotherapy is important. DOX and CP or other anticancer drugs with similar mechanisms of action are currently used in combined chemotherapy regimens for cancer patients. Both DOX and CP administration induces cancer cell apoptosis but also damages testicular germ cells in both animal models and men (Dohle, 2010; Marcon, et al., 2011; Meistrich, 2013; Meistrich, et al., 1982; Trost & Brannigan, 2012). Prior studies indicate that HN can decrease male germ cell apoptosis induced by intratesticular hormonal deprivation (Jia, et al., 2013; Lue, et al., 2010).

The current study showed that DOX which has activity in vitro induced germ cell apoptosis in male germ cells which was attenuated when DOX was administered with HN. In addition, in vivo HN treatment reduced the cytotoxic effects of CP in the testis in mice. Results indicated that HN prevents CP-induced apoptosis mainly in the early and late stages of the seminiferous epithelium, as spermatogenesis progresses, germ cell from all stages will be protected by HN treatment as seen in experiment 3. Methods disclosed herein provide HN as a means of cytoprotective effect of on male germ cells after cancer chemotherapy. Synthetic HN administration may also reduce testicular stress induced germ cell apoptosis through interactions of endogenous HN with BAX in the cytoplasm preventing the entry of BAX to the mitochondria to prevent the initiation of the apoptotic cascade in the testis (Jia, et al., 2013).

HN's protective effect on male germ cells from CP-induced apoptosis in a mouse melanoma with lung metastasis model was studied. Non-treated tumor-bearing mice had increased germ cell apoptosis compared to controls (no melanoma), indicating lung metastases induced weight loss and poor health causing defective spermatogenesis. HNG treatment showed a trend to mitigate germ cell apoptosis in tumor-bearing mice. CP treatment mainly induces differentiated spermatogonia and spermatocytes apoptosis in mice (Drumond et al., 2011). Consistent with published data, most apoptotic spermatocytes were cleared by phagocytosis by Sertoli cells 2 weeks after CP treatment. The increased percentage of tubules with apoptotic germ cells 2 weeks after CP treatment indicate a prolonged effect of CP on germ cells or impaired clearance of dead cells by Sertoli cells in tumor-bearing mice. However, HNG induced decrease in germ cell apoptosis failed to prevent testis weight loss induced by CP treatment in 2 weeks. Thus, long term study is needed to investigate the effects of HN and its analog on fertility preservation, blocking spermatozoa DNA damage, and possible minimizing the adverse effects on the progeny in response to chemotherapy.

HN gene expression has been found abundantly in lymphoma and gastric cancer indicating that HN may be an oncopeptide protecting cancer cell from undergoing apoptosis (Hartmann, et al., 2008; Maximov, et al., 2002; Mottaghi-Dastjerdi, et al., 2014; Tarantul & Hunsmann, 2001). In the same mouse melanoma model the effect of HNG on tumor growth and progression with or without concomitant CP treatment was screened. It was indicated that HNG administration alone for 2 weeks moderately decreased the number of metastatic lung melanomas without affecting the size of the lung tumors. HNG enhances the anti-cancer effects of CP on metastatic lung melanoma formation in mice.

These data provide evidence that HNG may have opposing actions on normal versus cancer cells: HNG protects normal cells from stress-induced apoptosis and enhances cancer regression in response to chemotherapy in mice. Because of the large intra-group variations on number of tumors found on the surface after HNG treatment alone, the HNG effect on tumor growth and apoptosis has to be determined in a larger scale experiments with different doses of HNG administration. Furthermore, the mechanisms of the effect of HNG in conjunction with CP treatment on the suppression of metastatic lung melanoma formation remain to be determined. It appears that HNG may either has direct inhibitory action on metastatic melanoma proliferation or promote melanoma cell differentiation in the lung or indirect action by modulating the microenvironment of the metastatic lung melanoma such as decreasing angiogenesis or altering immune cells homing to the cancer. CP and HNG may activate different signaling pathways in melanoma cells which resulted in enhanced anti-tumor effects. CP has a direct action on DNA causing DNA breaks, HNG may accelerate tumor cell differentiation or death through mitochondrial pathways. Another unexplored mechanism is the effect of HNG on the host defense mechanisms against the invasion of the lungs by metastatic melanoma.

In summary, 1) HN and HNG protected germ cell from apoptosis induced by DOX and CP treatment; 2) HNG enhanced the anti-cancer effect on CP suppression of lung metastatic melanoma formation in mice (including decreasing the number and converting undifferentiated cancer to differentiated cancer cells). Differentiation of otherwise highly mitotic undifferentiated metastatic cells may imply conversion to less aggressive malignancy. The combination of greater reduction of number of metastatic cancer cells and the reversion to more differentiated residual cells by combined HNG and chemotherapy, predicts that this combined therapy will be advantageous over chemotherapy alone. The effects of HNG to reduce apoptosis of germ cells when treated with chemotherapy indicated that this combined therapy will reduce and perhaps prevent the infertility seen by chemotherapy alone.

Humanin (HN) Polypeptides and Analogs (Tables 1-4)

TABLE 1

HN polypeptides - Properties and Cytoprotective Action

| HN Mutant | Mutation | Characteristics | Cytoprotective Action |
| --- | --- | --- | --- |
| HN-F6A | Phe6 to Ala | Loss of IGFBP-3 binding | Similar/more effective than HN. |
| HN-S7A or HN-C8A | Ser7 to Ala Cys8 to Ala | Loss of membrane receptor binding | Not effective, prevents HN self-dimerization |
| HN-C8P | Cys8 to Pro | Loss of BAX binding | Not effective, blocks intracellular HN action |
| HN-L12A | Leu12 to Ala | Dimerizes with and inactivates HN | HN antagonist, forms inactive dimer with HN |
| HN-S14G | Ser14 to Gly | Same mechanisms of action as HN | 10 to 1000 times more potent than HN in some cells. |

TABLE 2

HN Polypeptides and Analogs

| Name | Amino acid sequence | SEQ ID NO |
| --- | --- | --- |
| Humanin (HN) | MAPRGFSCLLLLTSEIDLPVKRRA | SEQ ID NO: 1 |
| S14G-HN (HNG) | MAPRGFSCLLLLTGEIDLPVKRRA | SEQ ID NO: 2 |
| D-Ser14 HN | MAPRGFSCLLLLT(DS)EIDLPVKRRA | SEQ ID NO: 3 |

TABLE 2-continued

HN Polypeptides and Analogs

| Name | Amino acid sequence | SEQ ID NO |
|---|---|---|
| AGA-HNG | MAPAGASCLLLLTGEIDLPVKRRA | SEQ ID NO: 4 |
| AGA-(D-Ser14)HN | MAPAGASCLLLLT(DS)EIDLPVKRRA | SEQ ID NO: 5 |
| AGA-(D-Ser14)HN17 | PAGASCLLLLT(DS)EIDLP | SEQ ID NO: 6 |
| AGA-(C8R)HNG17 | PAGASRLLLLTGEIDLP | SEQ ID NO: 7 |
| EF-HN | EFLIVIKSMAPRGFSCLLLLTSEIDLPVKRRA | SEQ ID NO: 8 |
| EF-HNG | EFLIVIKSMAPRGFSCLLLLTGEIDLPVKRRA | SEQ ID NO: 9 |
| EF-AGA-HNG | EFLIVIKSMAPAGASCLLLLTGEIDLPVKRRA | SEQ ID NO: 10 |
| Colivelin | SALLRSIPAPAGASRLLLLTGEIDLP | SEQ ID NO: 11 |
| L9R-HN | MAPRGFSCRLLLTSEIDLPVKRRA | SEQ ID NO: 12 |
| Humania (7) | MTPRGFSCLLLPTSETDLPVKRRX | SEQ ID NO: 13 |
| Humania (5) | MAPRGFSCLLLSTSEIDLPVKRXX | SEQ ID NO: 14 |
| Humania (3/11) | MAPRGFSCLLLSTSEIDLPVKRRA | SEQ ID NO: 15 |
| SHLP1 | MCHWAGGASNTGDARGDVFGKQAG | SEQ ID NO: 16 |
| SHLP2 | MGVKFFTLSTRFFPSVQRAVPLWTNS | SEQ ID NO: 17 |
| SHLP3 | MLGYNFSSPPCGTISIAPGFNFYRLYFIWVNGLAKVVW | SEQ ID NO: 18 |
| SHLP4 | MLEVMFLVNRRGKICRVPFTFFNLSL | SEQ ID NO: 19 |
| SHLP5 | MYCSEVGFCSEVAPTEIFNAGLVV | SEQ ID NO: 20 |
| SHLP6 | MLDQDIPMVQPLIKVRLFND | SEQ ID NO: 21 |
| HN-F6A | MAPRGASCLLLLTSEIDLPVKRRA | SEQ ID NO: 22 |
| HNG-F6A | MAPRGASCLLLLTGEIDLPVKRRA | SEQ ID NO: 23 |
| HN-S7A | MAPRGFACLLLLTSEIDLPVKRRA | SEQ ID NO: 24 |
| HN-C8P | MAPRGFSPLLLLTSEIDLPVKRRA | SEQ ID NO: 25 |

TABLE 3

HN Polypeptides and Analogs

| Name | Amino acid sequence | SEQ ID NO |
|---|---|---|
| P-S14 HN 4 | MAPRGFSCLLLLT(p-S)EIDLPVKRRA | SEQ ID NO: 26 |
| P-S7 HN 5 | MAPRGF(p-S)CLLLLTSEIDLPVKRRA | SEQ ID NO: 27 |
| P-S7/14 HN 6 | MAPRGF(p-S)CLLLLT(p-S)EIDLPVKRRA | SEQ ID NO: 28 |
| D-Ser14 HN 7 | MAPRGFSCLLLLT(D-S)EIDLPVKRRA | SEQ ID NO: 29 |
| D-Ser7 HN 8 | MAPRGF(D-Ser)CLLLLTSEIDLPVKRRA | SEQ ID NO: 30 |
| D-Ser7/14 HN 9 | MAPRGF(D-Ser)CLLLLT(D-Ser)EIDLPVKRRA | SEQ ID NO: 31 |
| AGA-(D-Ser14) HN 10 | MAPAGASCLLLLT(D-Ser)EIDLPVKRRA | SEQ ID NO: 32 |
| AGA-(D-Ser14) HN17 11 | PAGASCLLLLT(D-Ser)EIDLP | SEQ ID NO: 33 |
| EF-(S7A)HN 15 | EFLIVIKSMAPRGFACLLLLTSEIDLPVKRRA | SEQ ID NO: 34 |
| EF-HNG-KKK 16 | EFLIVIKSMAPRGFSCLLLLTGEIDLPVKKKK | SEQ ID NO: 35 |
| EF-HN 17 | EFLIVIKSMAPRGFSCLLLLTSEIDLPVKRRA | SEQ ID NO: 36 |
| EH-HNA 18 | EFLIVIKSMAPRGFSALLLLTSEIDLPVKRRA | SEQ ID NO: 37 |
| EF-HNG 19 | EFLIVIKSMAPRGFSCLLLLTGEIDLPVKRRA | SEQ ID NO: 38 |
| EF-AGA-HNG 22 | EFLIVIKSMAPAGASCLLLLTGEIDLPVKRRA | SEQ ID NO: 39 |

TABLE 4

| | HN Polypeptides and Analogs |
|---|---|
| HN 1 | MAPRGFSCLLLLTSEIDLPVKRRA SEQ ID NO: 40 |
| HNG 2 | MAPRGFSCLLLLTGEIDLPVKRRA SEQ ID NO: 41 |
| HNA 3 | MAPRGFSALLLLTSEIDLPVKRRA SEQ ID NO: 42 |
| P-S14 HN 4 | MAPRGFSCLLLLT(p-S)EIDLPVKRRA SEQ ID NO: 43 |
| P-S7 HN 5 | MAPRGF(p-S)CLLLLTSEIDLPVKRRA SEQ ID NO: 44 |
| P-S7/14 HN 6 | MAPRGF(p-S)CLLLLT(p-S)EIDLPVKRRA SEQ ID NO: 45 |
| D-Ser14 HN 7 | MAPRGFSCLLLLT(D-S)EIDLPVKRRA SEQ ID NO: 46 |
| D-Ser7 HN 8 | MAPRGF(D-Ser)CLLLLTSEIDLPVKRRA SEQ ID NO: 47 |
| D-Ser7/14 HN 9 | MAPRGF(D-Ser)CLLLLT(D-Ser)EIDPPVKRRA SEQ ID NO: 48 |
| AGA-(D-Ser14) HN 10 | MAPAGASCLLLLT(D-Ser)EIDLPVKRRA SEQ ID NO: 49 |
| AGA-(D-Ser14) HN17 11 | PAGASCLLLLT(D-Ser)EIDLP SEQ ID NO: 50 |
| S7A HN 12 | MAPRGFACLLLLTSEIDLPVKRRA SEQ ID NO: 51 |
| S7A HNG17 13 | PRGFACLLLLTSEIDLP SEQ ID NO: 52 |
| HNG-KKK 14 | YMAPRGFSCLLLLTGEIDLPVKKKK SEQ ID NO: 53 |
| EF-(S7A)HN 15 | EFLIVIKSMAPRGFACLLLLTSEIDLPVKRRA SEQ ID NO: 54 |
| EF-HNG-KKK 16 | EFLIVIKSMAPRGFSCLLLLTGEIDLPVKKKK SEQ ID NO: 55 |
| EF-HN 17 | EFLIVIKSMAPRGFSCLLLLTSEIDLPVKRRA SEQ ID NO: 56 |
| EH-HNA 18 | EFLIVIKSMAPRGFSALLLLTSEIDLPVKRRA SEQ ID NO: 57 |
| EF-HNG 19 | EFLIVIKSMAPRGFSCLLLLTGEIDLPVKRRA SEQ ID NO: 58 |
| EFLIVIKS 20 | EFLIVIKS SEQ ID NO: 59 |
| AGA-HNG 21 | MAPAGASCLLLLTGEIDLPVKRRA SEQ ID NO: 60 |
| EF-AGA-HNG 22 | EFLIVIKSMAPAGASCLLLLTGEIDLPVKRRA SEQ ID NO: 61 |
| HNG-17 23 | PRGFSCLLLLTGEIDLP SEQ ID NO: 62 |

HNG: An HN derivative, which has a Gly substitution of Ser14 of HN.

HN derivatives can be selected from: Humanin with S14P, P-S7 HN, P-S7/14 HN, (D-Ser14)HN, (D-Ser7)HN, (D-Ser7/14)HN, AGA-(D-Ser14)HN, AGA-(D-Ser14) HN17, EFLIVIKS-HNG, EFLIVIKS-HNA, EFLIVIKS-HN, EFLIVIKS-HNG-KKK, EFLIVIKS-(S7A)HN, and EFLIVIKS-AGA-HNG, and chimeric combinations thereof. The "S14P" means that the S (serine) at location 14 in the wild-type HN has been replaced with P (proline). The same convention applies for other substitutions (e.g., S7A).

"D-Ser7" means that the Serine at location 7 has been switched (racemized) from a normal L-isomer to the D-isomer. "AGA-HN" is a shorthand name of the HN derivative in which the Arg4 and Phe6 amino acids are substituted with Alanine to form R4A/F6A-HN (this is named for the AGA triplet at locations 4, 5, and 6 in the HN derivative. "HN17" is a truncated form of HN that includes 17 amino acids from Pro3 to Pro19.

A polypeptide having an amino acid sequence of: Pro-Xn1-(Cys/bXaa)-(Leu/Arg)-Xn2-Leu-Thr-(Gly/Ser)-Xn3-Pro (I) wherein "Cys/bXaa" indicates Cys or a basic amino acid; "(Leu/Arg)" indicates Leu or Arg; "(Gly/Ser)" indicates Gly or Ser; and Xn1, Xn2, and Xn3 independently indicate arbitrary amino acid sequences not more than 10 residues in length, respectively;

A polypeptide having an amino acid sequence of: Pro-Xn1-(Cys/bXaa)-(Leu/Arg)-Xn2-Leu-Thr-(Gly/Ser)-Xn3-Pro (1).

Herein, "Cys/bXaa" indicates Cys or a basic amino acid; "(Leu/Arg)" indicates Leu or Arg; "(Gly/Ser)" indicates Gly or Ser; and Xn1, Xn2, and Xn3 independently indicate arbitrary amino acids not more than 10 residues, respectively.

A polypeptide that has the amino acid sequence of: Pro-(Xaa)1-10-(Cys/bXaa)-(Leu/Arg)-(Xaa)1-10-Leu-Thr-(Gly/Ser)-(Xaa)1-10Pro (wherein Xaa indicates an arbitrary amino acid; "(Xaa)m-n" indicates m to n residues of arbitrary amino acids; "bXaa" indicates a basic amino acid; "Cys/bXaa" indicates Cys or a basic amino acid; "(Leu/Arg)" indicates Leu or Arg; and "(Gly/Ser)" indicates Gly or Ser).

Basic amino acids refer to amino acids in which its R group (side chain) is positively charged at pH 7.0. Examples of natural basic amino acids include Arg, Lys, and His.

The amino acid sequences of a polypeptide that has Arg, Lys, or His as the basic amino acids can be represented, for example, as: Pro-Xn1-(Cys/Arg/Lys/His)-(Leu/Arg)-Xn2-Leu-Thr-(Gly/Ser)-Xn3-Pro (wherein "(Cys/Arg/Lys/His)" indicates Cys, Arg, Lys, or His; "(Leu/Arg)" indicates Leu or Arg; "(Gly/Ser)" indicates Gly or Ser; and Xn1, Xn2, and Xn3 independently indicate arbitrary amino acids not more than 10 residues, respectively). Herein, Arg and Lys can be the basic amino acid at this position.

Xn1, Xn2, and Xn3 are independently arbitrary amino acids of 2 to 6, 0 to 4, and 2 to 6 residues, respectively (that is, Xn1=(Xaa)2-6, Xn2=(Xaa)0-4, and Xn3=(Xaa)2-6); or 3 to 5, 1 to 3, and 3 to 5 residues, respectively (that is, Xn1=(Xaa)3-5, Xn2=(Xaa)1-3, and Xn3=(Xaa)3-5); or 4, 2, and 4 residues, respectively (that is, Xn1=(Xaa)4, Xn2=(Xaa)2, and Xn3=(Xaa)4). Added amino acids of about 6 residues sometimes forms an a-helix and behaves like a single amino acid residue. A polypeptide of the present invention may be a polypeptide wherein arbitrary amino acids with no more than 6 residues are added to all or any one of Xn1, Xn2, and Xn3 consisting of arbitrary amino acids of 4 residues, 2 residues, and 4 residues, respectively.

A sequence of Xn1 includes, for example, sequences consisting of (Arg/Ala)-(Gly/Ala)-(Phe/Ala)-(Ser/Ala), and sequences with conservative substitution thereof. Herein, for example, "Arg/Ala" indicates Arg or Ala ("I" indicates that it is either one of the residues; the same is indicated throughout the description herein). Examples of such sequences include Arg-Gly-Phe-Ser, Ala-Gly-Phe-Ser, Arg-Ala-Phe-Ser, Arg-Gly-Ala-Ser, Arg-Gly-Phe-Ala, and so on. Other examples include Arg-Gly-Ala-Ala, Arg-Ala-Phe-Ala, Arg-Ala-Ala-Ser, Arg-Ala-Ala-Ala, Ala-Gly-Phe-Ala, Ala-Gly-Ala-Ser, Ala-Gly-Ala-Ala, Ala-Ala-Phe-Ser, Ala-Ala-Phe-Ala, Ala-Ala-Ala-Ser, Ala-Ala-Ala-Ala, and such.

Conservative substitution can be exemplified by substitution within a group of amino acids, corresponding to conservative substitution. On the other hand, the sequence of Xn2 includes, for example, sequences consisting of (Leu/Ala)-(Leu/Ala), and sequences with conservative substitution thereof. Such sequences include Leu-Leu, Ala-Leu, Leu-Ala, and such. Ala-Ala can be also exemplified as such sequences. Furthermore, the sequence of Xn3 includes, for example, sequences consisting of (Glu/Ala)-(Ile/Ala)-(Asp/Ala)-(Leu/Ala), and sequences with conservative substitution thereof. Such examples include Glu-Ile-Asp-Leu, Ala-Ile-Asp-Leu, Glu-Ala-Asp-Leu, Glu-Ile-Ala-Leu, Glu-Ile-Asp-Ala, and so on. Other examples are Glu-Ile-Ala-Ala, Glu-Ala-Asp-Ala, Glu-Ala-Ala-Leu, Glu-Ala-Ala-Ala, Ala-Ile-Asp-Ala, Ala-Ile-Ala-Leu, Ala-Ile-Ala-Ala, Ala-Ala-Asp-Leu, Ala-Ala-Asp-Ala, Ala-Ala-Ala-Leu, Ala-Ala-Ala-Ala, and so on. The sequences of Xn1, Xn2, and Xn3 may be selected from arbitrary combinations.

Example 2: Experiment 5, The Effects of Humanin and Its Analogs on Male Germ Cell Apoptosis Induced by Chemotherapeutic Drugs Advanced chemotherapies of cancer patients have increased survival and life expectancy, and also increased expectations for a more favorable adverse effect profile. Of the long term adverse effects of chemotherapies on cancer survivors, infertility has emerged as one of the chief complaints (Marcon L, et al., 2008; Meistrich M L., 2009; Lee S H, et al., 2013). Accordingly, the role of HN and HN analogs in preventing male germ cell apoptosis induced by chemotherapeutic drugs in mouse models was explored. Doxorubicin (DOX) was chosen for the ex vivo study as an anthracycline antibiotic that acts by intercalating DNA to suppress proliferation and increase apoptosis and is active in vitro (Watring W G, et al., 1974). Cyclophosphamide (CP) was used in the in vivo animal experiments because it requires liver cytochrome P450 metabolism to become the activated form of the drug, 4-hydroxy-cyclophosphamide, which circulates to cancer cells and damages DNA leading to apoptosis (Gor P P, et al., 2010).

The effects of five HN analogs including HNG (HN-S14G, a potent agonist), HNG-F6A (no binding to IGFBP-3), HN-S7A (no self-dimerization), HN-C8P (no binding to BAX), and HN-L12A (a HN antagonist) on CP-induced male germ cell apoptosis in mice were studied. CP-induced germ cell apoptosis was inhibited by HN, HNG, HNG-F6A, HN-S7A, and HN-C8P (less effective), but not by HN-L12A. HN, HN-S7A, and HN-C8P restored CP-suppressed STAT3 phosphorylation. These results suggest that HN: 1) decreases DOX (ex vivo) and CP (in vivo) induced male germ cell apoptosis; 2) action is mediated by the membrane receptor/STAT3 with minor contribution by BAX-binding pathway; 3) self-dimerization or binding to IGFBP-3 may not be involved in HN's effect in testis. This data suggests that HN is an important molecule in the regulation of germ cell homeostasis after injury and agonistic analogs may be developed for treating male infertility or protection against chemotherapy side effects.

Materials and Methods
Materials

HN peptide and the HN analogs were synthesized by CPC Scientific (Sunnyvale, Calif.). A description of the characteristics of each of the HN analogs is provided in Table 1. In in vivo experiments, HN and five HN analogs were studied by using a CP-induced male germ cell apoptosis mouse model. These analogs include HNG (HN with a substitution of serine 14 to glycine, HN-S14G) (Kunesová G, et al., 2008; Miao J, et al., 2008; Yamada M, et al., 2008), HNG-F6A (HNG with a substitution of alanine for 6th phenylalanine, no binding to IGFBP-3) (Ikonen M, et al., 2003) HN-S7A (HN with a substitution of alanine for 7th serine, dimerization defective) (Yamagishi Y, et al., 2003), HN-C8P (HN with a substitution of proline for 8th cysteine, no binding to BAX) (Hashimoto Y, et al., 2001; Guo B, et al., 2003; Yamagishi Y, et al., 2003), and HN-L12A (HN with a substitution of alanine for 12th leucine, HN antagonist dimerizes with HN preventing HN binding to receptor) (Yamagishi Y, et al., 2003).

Mouse Seminiferous Tubule Ex Vivo Culture

A total of 15 mice were used for ex vivo studies. The animals were sacrificed and seminiferous tubules isolated from testes were cut into small segments under a dissecting microscope to identify light (early stages I-IV and late stages XI-XII) of the seminiferous epithelium) and dark (middle stages VII-VIII) segments. Ten to twelve light segments (2 mm in length) were placed per well on a six well plate with 2 ml serum free medium of F-10 Ham nutrient mixture (Gibco, Life Technologies, Grand Island, N.Y.) following these treatments: control (Con, n=15 where n is the number of times the treatment was repeated with segments obtained from different donor animals), heat (43° C., 15 min.; used as a positive control, n=10), HN 10 µg/mL (HN, n=9), doxorubicin 1 µM (Dox1, n=7), doxorubicin 1 µM+HN 10 µg/mL (Dox1+HN, n=7), doxorubicin 10 µM (Dox10, n=10), and doxorubicin 10 µM+HN 10 µg/mL (Dox10+HN, n=10). After 12 hours of incubation at 34° C. with 5% $CO_2$, the seminiferous tubules from the seven treatment groups were used to make "squashed" seminiferous tubule preparations on a slide for TUNEL assay to detect germ cell apoptosis (Erkkila K, et al., 1997). To quantify the rate of germ cell apoptosis, the squashed segments of seminiferous tubules were examined with an American Optical Microscope (Scientific Instruments, Buffalo, N.Y.) with a 40× objective and a 10× eyepiece lens. A square grid fitted within the eyepiece provided a reference area of 62,500 $\mu m^2$. The TUNEL positive apoptotic germ cells within the frame of grid were counted in 4 segments of seminiferous tubules in each group. The incidence of germ cell apoptosis was expressed as the number of apoptotic germ cells per $mm^2$.

Animals and In Vivo Experiments

Adult (12-week-old) male mice (C57BL/6J wild type, purchased from Jackson Laboratories, Bar Harbor, Me.) were used for animal experiments. All mice were housed in a standard animal facility under controlled temperature (22° C.) and photoperiod of twelve hours of light and twelve hours of darkness with free access to food and water. Animal handling and experimentation were in accordance with the recommendation of American Veterinary Medical Association and were approved by the animal care and use review committee at the Los Angeles Biomedical Research Institute at Harbor-University of California, Los Angeles (Harbor-UCLA) Medical Center.

For the HN analog experiments, male mice were divided into seven groups (n=4-5 per group) and received one of the following treatments and sacrificed after 24 hours: 1) vehicle (control); 2) a single intra-peritoneal (IP) injection of HN peptide [HN, 40 mg/Kg body weight (BW)]; 3) a single IP injection of CP (CP, 200 mg/Kg BW); 4) IP injection of CP and HN (CP+HN); 5) a single IP injection of each HN analog (HNG 5 mg/Kg BW, HNG-F6A 5 mg/Kg BW, HN-S7A 40 mg/Kg BW, HN-C8P 40 mg/Kg BW, or HN-L12A 40 mg/Kg BW); 6) IP injection of CP and each HN analog (CP+HNG, HNG-F6A, HN-S7A, HN-C8P, or HN-L12A); and 7) IP injection of CP+HN+HN analog (HN-S7A, HN-C8P, or HN-L12A; to assess whether the analogs has enhancing or inhibitory effect on HN).

Tissue Preparation

To facilitate testicular fixation by using a whole-body perfusion technique, all animals were injected with heparin (130 IU/100 g BW, IP) 15 min before a lethal injection of sodium pentobarbital (200 mg/kg BW, IP) (Lue Y H, et al., 1999). One testis was removed and weighed after perfusion with saline. Portions of testicular parenchyma were snap frozen in liquid nitrogen, and stored at −80 C for Western blotting. The other testis was fixed by vascular perfusion with Bouin's solution, and processed with routine paraffin embedding for in situ detection of apoptosis.

Western Blotting Analysis

Western blotting was performed as described previously (Jia Y, et al., 2009). In brief, proteins were denatured and separated by sodium dodecyl sulfate-polyacrylamide gel electrophoresis (SDS-PAGE) system (Invitrogen, Carlsbad, Calif.). After transferring, the Immuno-blot PVDF Membrane (Bio-Rad, Hercules, Calif.) was blocked for 1 h and then probed using anti-STAT3 or anti-pSer727 STAT3 (Cell signaling Technology, Inc., Beverly, Mass.) overnight at 4 C with constant shaking. After washing, membrane was then incubated with an anti-mouse (for STAT3 antibody, Santa Cruz Biotechnology, Santa Cruz, Calif.) or anti-rabbit (for pSer727 STAT3 antibody, Amersham Biosciences, Piscataway, N.J.) IgG-HRP secondary antibody. All antibodies were diluted in blocking buffer. For immunodetection, membrane was incubated with enhanced chemiluminescence solutions per the manufacturer's specifications (Amersham Biosciences, Piscataway, N.J.), and exposed to Hyperfilm ECL (Denville Scientific Inc., Metuchen, N.J.).

Assessment of Apoptosis

Detection of apoptotic cells was performed in Bouin's'-fixed, paraffin-embedded testicular sections by the terminal deoxynucleotidyl transferase (TdT)-mediated deoxy-UTP nick end labeling (TUNEL) technique (Sinha Hikim A P, et al., 1997) using an ApopTag-peroxidase kit (Chemicon International, Inc., Temecula, Calif.). Enumeration of the Sertoli cell nuclei with distinct nucleoli and apoptotic germ cell population was quantified at stages I-IV (early stages), stages VII-VIII (middle stages) and stages XI-XII (late stages) of the seminiferous epithelial cycle using an Olympus BH-2 microscope (New Hyde Park, N.Y.). Stages were identified according to the criteria proposed by Russell et al for paraffin sections (Russell L, 1977). The rate of germ cell apoptosis (apoptotic index, AI) was expressed as the number of apoptotic germ cells per Sertoli cells (Sinha Hikim A P, et al., 1997).

Statistical Analysis

Statistical analyses were performed using the SigmaStat 2.0 Program (Jandel Cooperation, San Rafael, Calif.). The Student-Newman-Keuls test after one-way repeated measures ANOVA was used for statistical significance. The seminiferous tubule culture experiments were replicated 7-15 times and for animal experiments each group has 4-5 mice. Differences were considered significant if P<0.05.

Results

Effect of Doxorubicin on Germ Cell Apoptosis in Seminiferous Tubule Cultures

Figure 13:
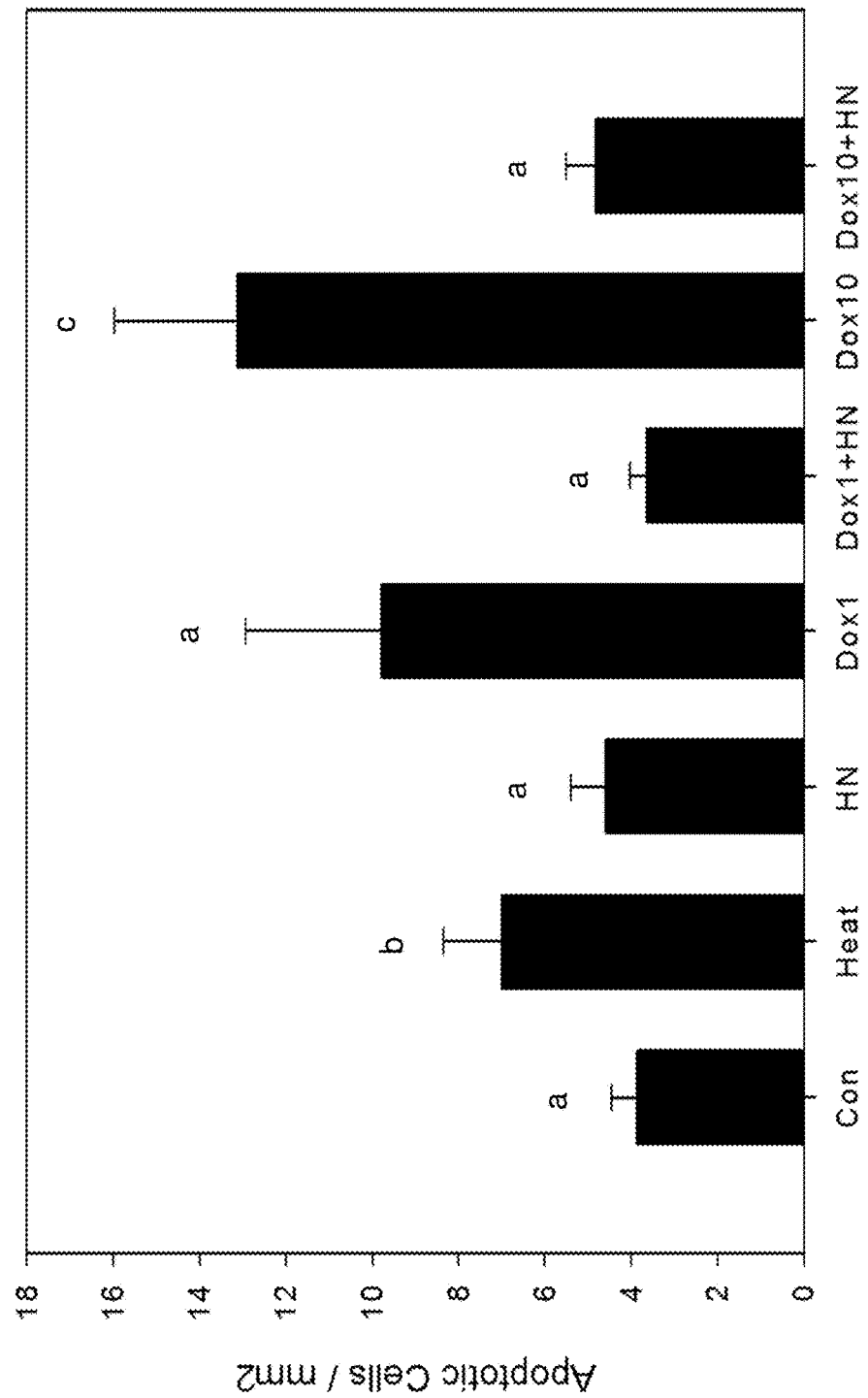
FIG. 13 shows a histogram of the quantity of apoptotic cells in squashed seminiferous tubules (y-axis, mean±SEM) after ex vivo treatment with low dose doxorubicin (DOX1), high dose doxorubicin (DOX10), Humanin (HN), low dose Dox1 and HN (Dox1+HN), high dose Dox10 and HN (Dox10+HN) or no treatment (Con) ex-vivo. Exposing the seminiferous tubules to 43 degrees served as a positive control (Heat). Means with unlike superscripts (e.g., a, b and c as shown above the histograms) are significantly different (P<0.05). The rate of germ cell apoptosis is similar between control and HN groups (p<0.05). High dose, but not low dose, of doxorubicin (DOX) significantly increased the number of apoptotic cells compared with control (p<0.05). Humanin treatment (HN) significantly attenuated germ cell apoptosis induced by high dose of DOX treatment (p<0.05).

In short term (12 hours) ex vivo seminiferous tubule cultures HN (10 μg/mL) treatment alone had no significant effect on germ cell apoptosis when compared with control. As expected, heat exposure (43° C., 15 min.) serving as a positive control significantly increased the rate of apoptosis compared to control and HN treated groups (p<0.05). HN (10 μg/mL) prevented the heat induced germ cell apoptosis. Low dose doxorubicin (1 μM) treatment increased apoptosis but did not reach statistical difference because of the large variations compared with control; addition of HN did not significantly decrease apoptosis (FIG. 13). High dose doxorubicin (10 μM) treatment significantly increased apoptosis compared to control (p<0.05); while HN (10 μg/mL) significantly reduced the number of apoptotic germ cells induced by high dose doxorubicin (p<0.05) (FIG. 13). In the squashed tubules, the germ cells undergoing apoptosis were mainly pachytene spermatocytes and round spermatids, no apoptotic spermatogonia were detected.

Effects of HN and HNG on CP-Induced Apoptosis in Testis

Figure 14A:
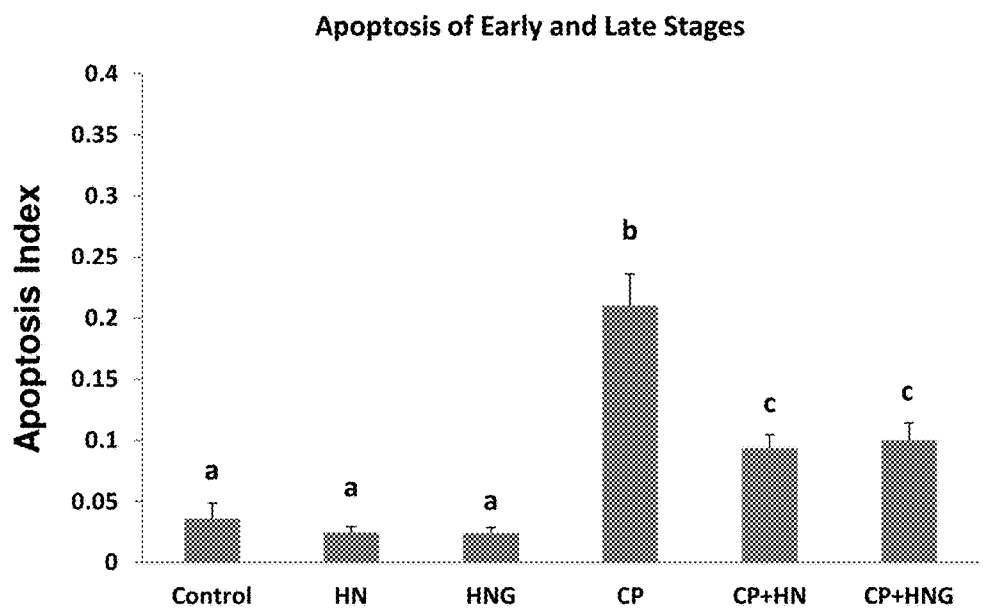
FIGS. 14A-14B show the effect of HN and HNG on Cyclophosphamide (CP)-induced male germ cell apoptosis. Mice were treated with vehicle control (Control), HN, HNG (Humanin-S14G), CP, CP and HN (CP+HN) or CP and HNG (CP+HNG) as described in experimental procedures (n=4 each group). Apoptotic Index (AI) stands for the ratio of TUNEL positive germ cells per Sertoli cell (also in following figures). HN or HNG alone did not change apoptosis compared with control. CP significantly increased germ cell apoptosis both in early+late stages (I-IV and XI-XII, FIG. 14A) and middle stages (VII-VIII, FIG. 14B) as compared to control. HN significantly suppressed CP-induced apoptosis in early+late stages but not in middle stages. HNG prevented CP-induce apoptosis both in early+late and middle stages but fail to reach significance in the middle stages (P>0.05). Values are means±SEM. Means with unlike superscripts (e.g., a, b and c as shown above the histograms) are significantly different (P<0.05).
Figure 14B:
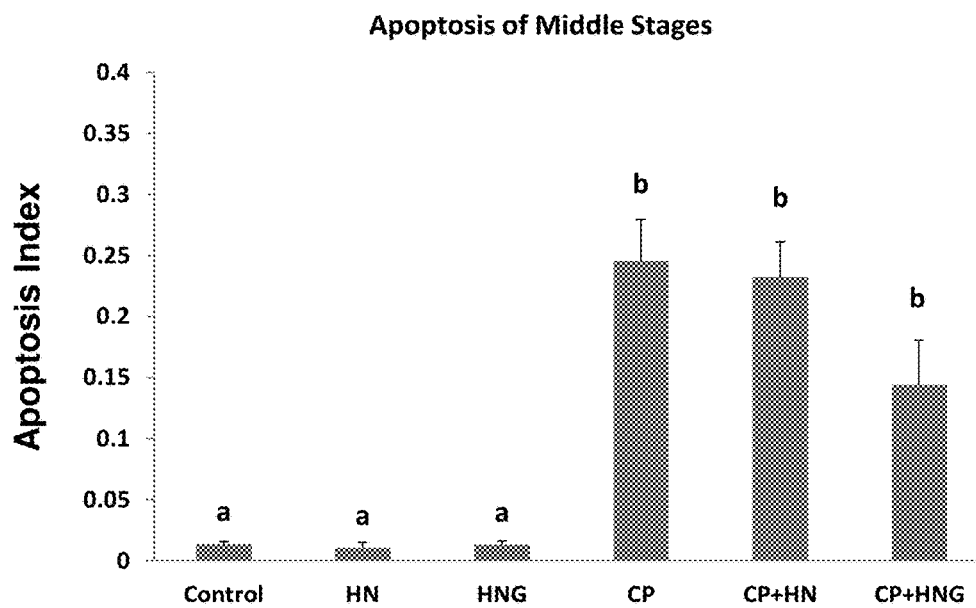
Figure 15A:
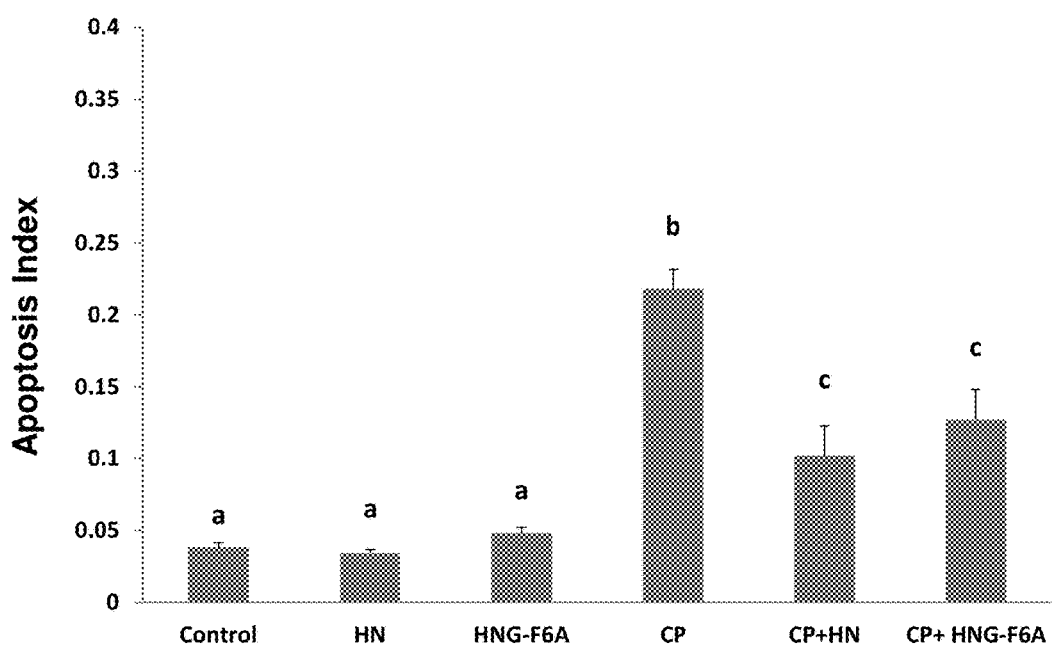
FIGS. 15A-15B show the effect of HN and HNG-F6A on Cyclophosphamide (CP)-induced male germ cell apoptosis. Mice were treated with vehicle control (Control), HN, HNG-F6A (Humanin-S14G-F6A), CP, CP+HN or CP+HNG-F6A as described in experimental procedures (n=4 each group). HN or HNG-F6A alone did not change apoptosis compared with control. Compared with control, CP increased germ cell apoptosis both in early+late (I-IV and XI-XII, FIG. 15A) and middle (VII-VIII, FIG. 15B) stages. HN significantly suppressed CP-induced apoptosis in early+late stages but not in middle stages. HNG-F6A prevented CP-induce apoptosis both in early+late and middle stages remarkably. Values are means±SEM. Means with unlike superscripts (e.g., a, b and c as shown above the histograms) are significantly different (P<0.05).
Figure 15B:
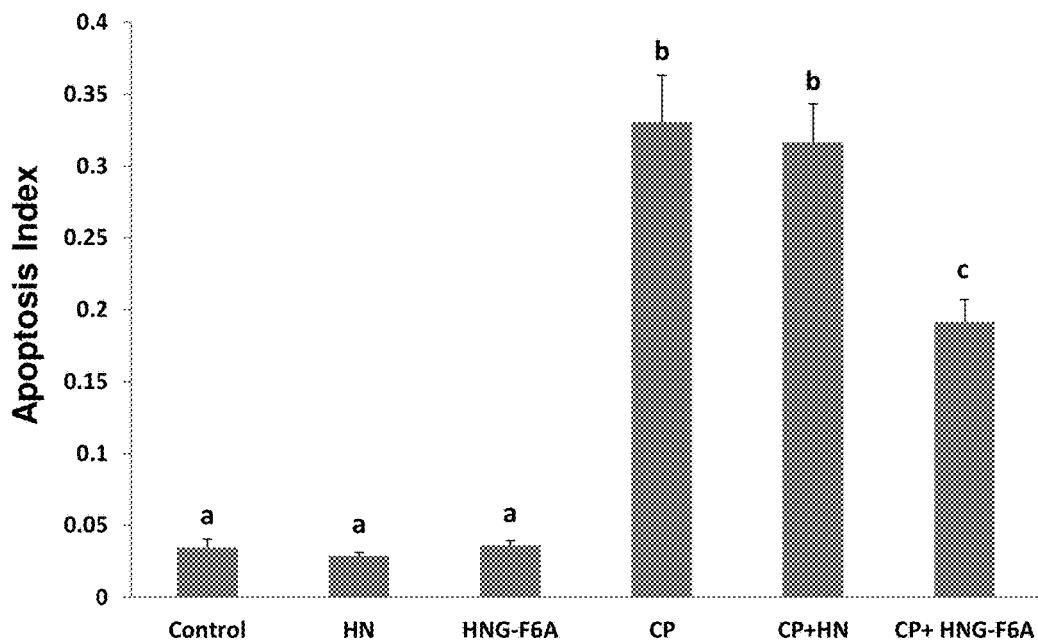

Synthetic HN or HNG peptide alone did not change the spontaneous germ cell apoptosis. CP treatment increased germ cell apoptosis at both early+late stages (I-IV and XI-XII) (FIG. 2 upper panel, CP: 0.21±0.03, p<0.01 compared with control group, 0.04±0.01) and middle stages (VII-VIII) of seminiferous epithelial cycle in mice (bottom panel, CP: 0.25±0.03; p<0.01 compared with control group, 0.01±0.01). CP-induced germ cell apoptosis was significantly (~57%) inhibited by HN administration (40 mg/kg BW) in early+late stages (stages I-IV and XI-XII) (FIG. 14A, CP+HN: 0.09±0.01, p<0.05 compared with CP treated group), but not in middle stages (stages VII-VIII) (bottom panel, CP+HN: 0.24±0.03; p>0.05 compared with CP treated group). Similarly, HNG at 5 mg/kg BW was able to significantly inhibit (~52%) the CP-induced germ cell apoptosis in stages I-IV and XI-XII (FIG. 14A, upper panel, CP+HNG: 0.10±0.01, p<0.05 compared with CP treated group) which was similar to the effect of HN at 8-fold higher dose in early+late stages. HNG also prevented ~36% of CP-induced germ cell apoptosis in middle stages (stages VII-VIII) (FIG. 14B, bottom panel, CP+HNG: 0.14±0.04 compared with CP group), although this effect did not reach statistical significance (p>0.05). In this and all subsequent in vivo experiments mainly pachytene spermatocytes and round spermatids but not spermatogonia underwent apoptosis Effect of HNG-F6A, a HN Analog that Does Not Bind to IGFBP-3, on Germ Cell Apoptosis In cell culture systems synthetic HNG-F6A peptide does not bind with IGFBP-3 (Ikonen M, et al., 2003). In present study, HNG-F6A alone did not change spontaneous germ cell apoptosis. Like HNG, HNG-F6A at 5 mg/kg BW dose was able to inhibit (~38%) the CP-induced germ cell apoptosis at stages I-IV and XI-XII (FIG. 15A, upper panel, CP+HNG-F6A: 0.13±0.02, p<0.05 compared with CP treated group: 0.21±0.01) which was similar to the effect of HN at 8-fold higher dose (40 mg/kg BW) in early+late stages (I-IV and XI-XII). In addition, HNG-F6A also prevented ~42% of CP-induced germ cell apoptosis in middle stages (VII-VIII) (FIG. 15B, bottom panel, CP+HNG-F6A: 0.19±0.02 vs CP: 0.33±0.03, p<0.05).

Figure 16A:
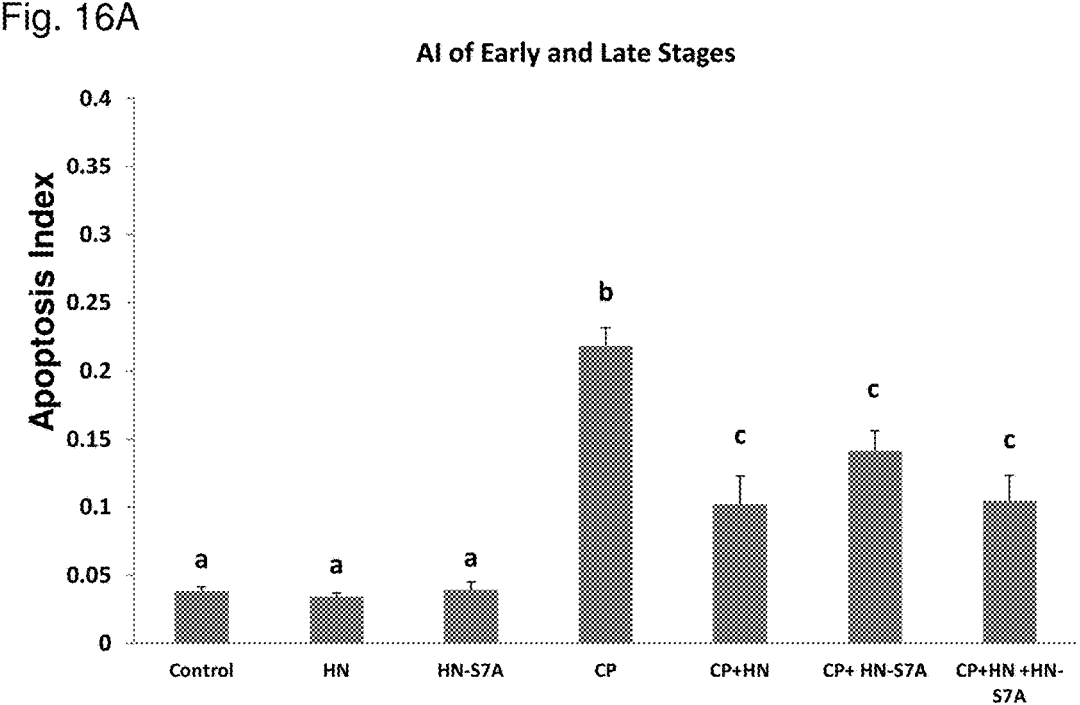
FIGS. 16A-16D show the effect of HN and HN-S7A on Cyclophosphamide (CP)-induced male germ cell apoptosis and changes of STAT3 phosphorylation. Mice were treated with vehicle (Control), HN, HN-S7A, CP, CP+HN, CP+HN-S7A, or CP+HN+HN-S7A as described in experimental procedures (n=5 each group).
Figure 16B:
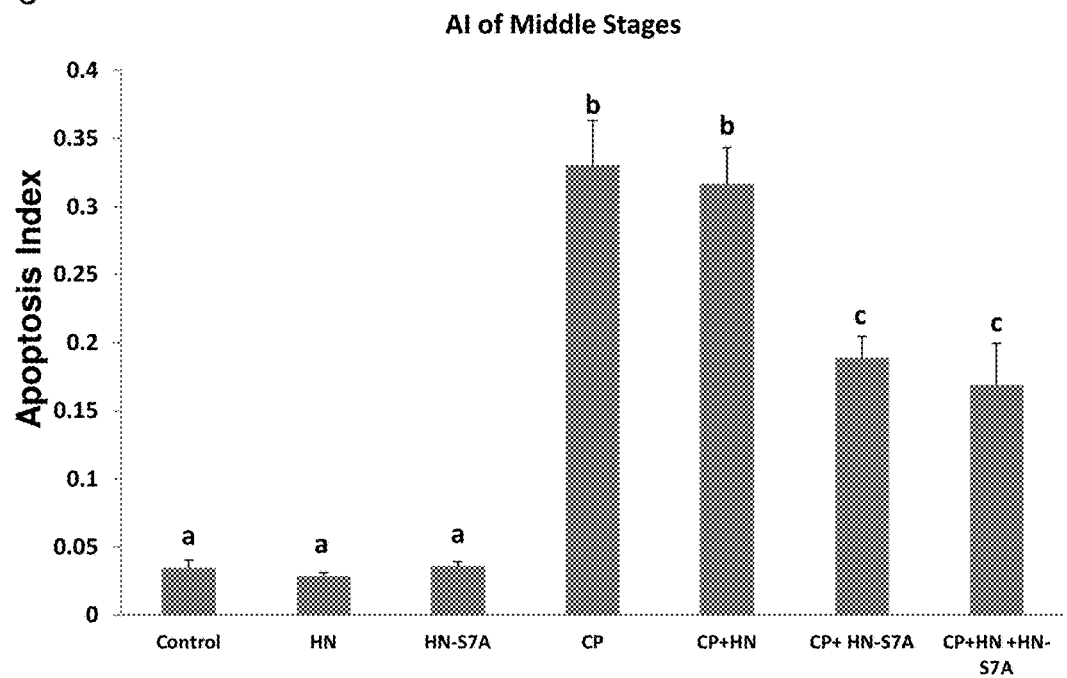
Figure 16C:
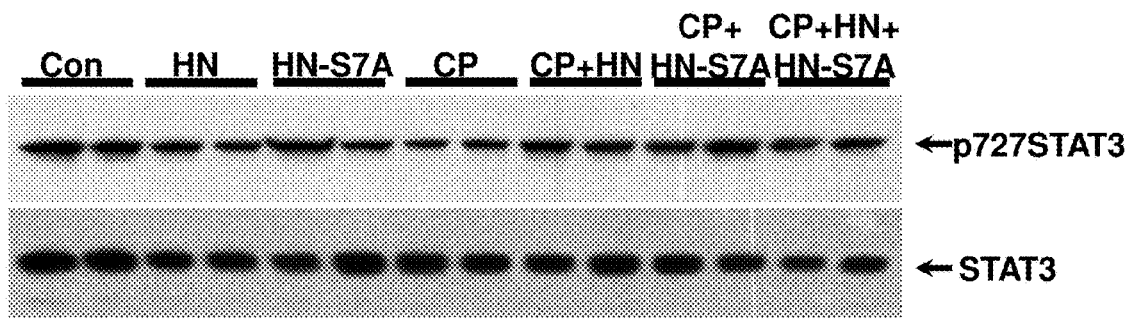
Figure 16D:
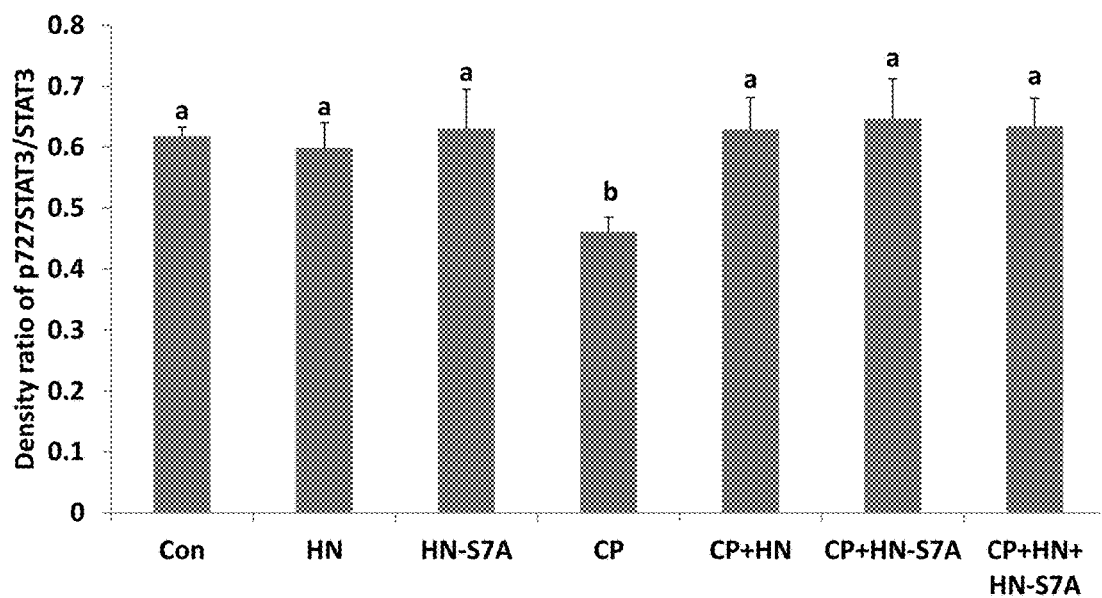
Figure 17A:
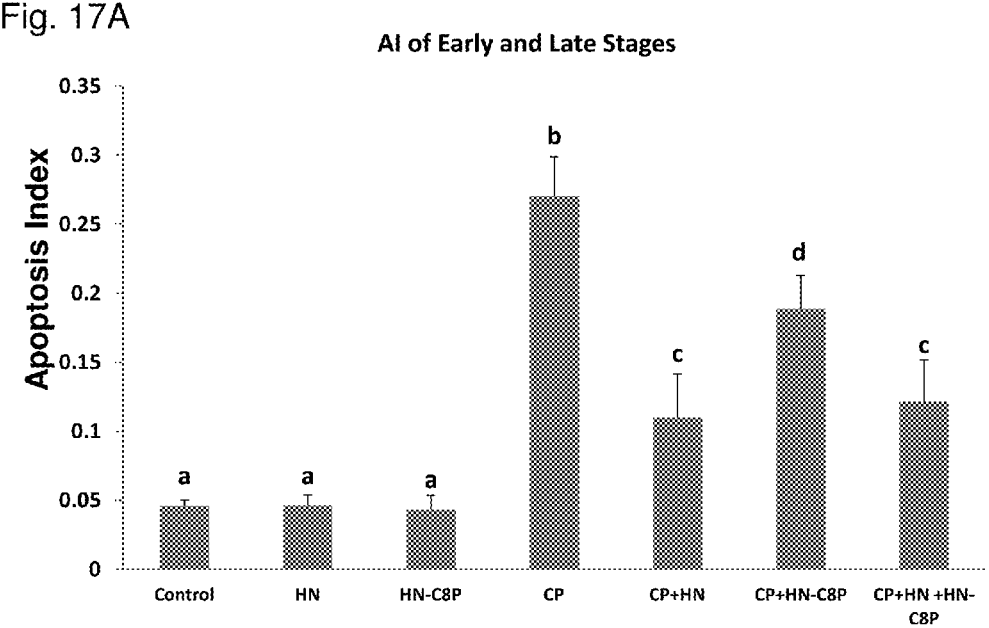
FIGS. 17A-17D show the effect of HN and HN-C8P on Cyclophosphamide-induced male germ cell apoptosis and changes of STAT3 phosphorylation. Mice were treated with vehicle (Control), HN, HN-C8P, CP, CP+HN, CP+HN-C8P or CP+HN+HN-C8P as described in experimental procedures (n=5 each group).
Figure 17B:
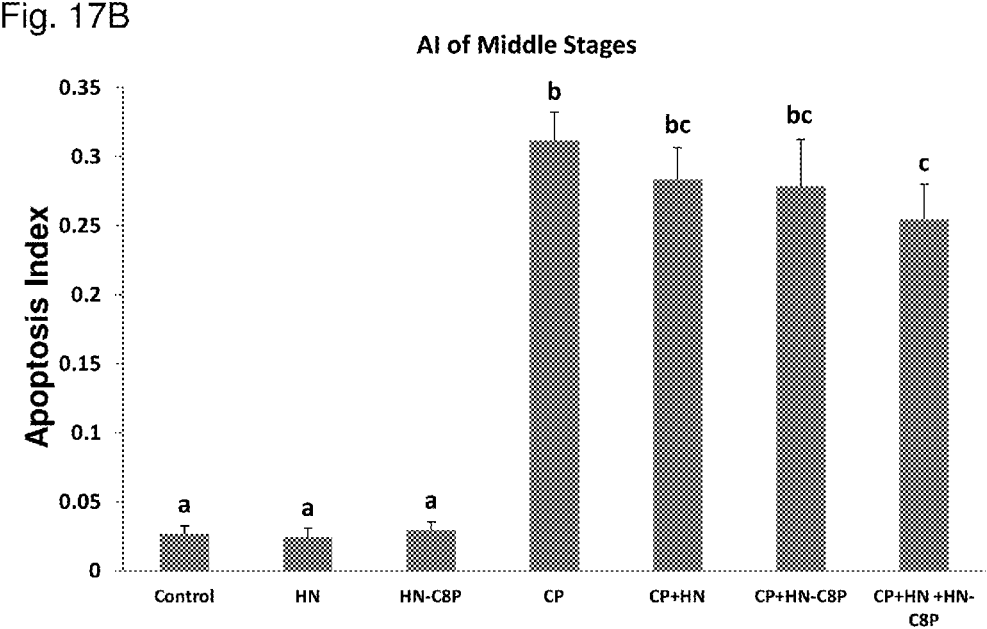
Figure 17C:
Figure 17D:
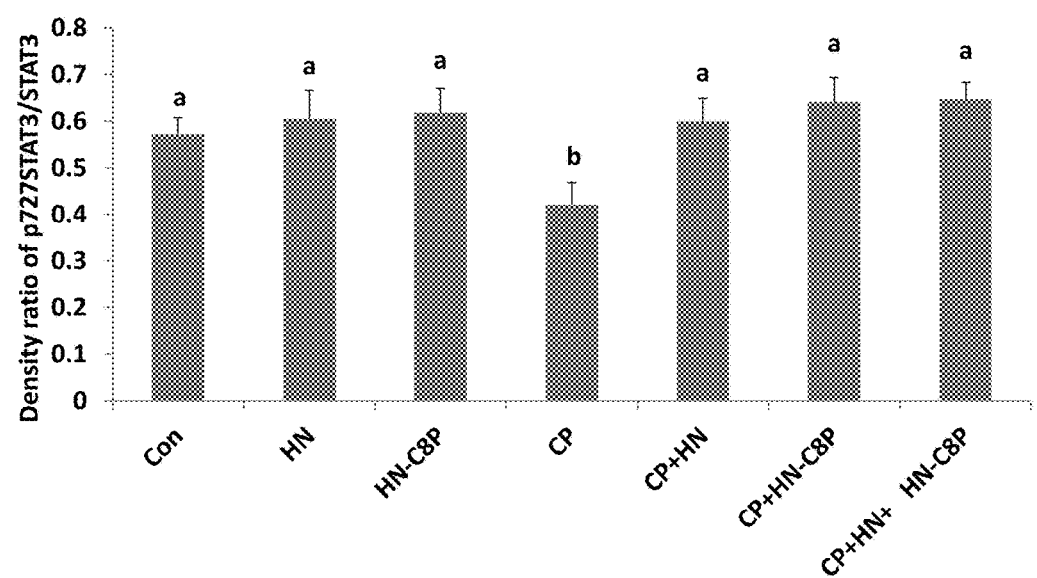

Effects of HN Analogs that Do Not Dimerize (HN-S7A) or Bind to BAX (HN-C8P) on Male Germ Cell Apoptosis Synthetic HN-S7A or HN-C8P peptide alone did not change the spontaneous germ cell apoptosis. Similar to HN, CP-induced germ cell apoptosis in the early and late stages (I-IV and XI-XII) was inhibited by same dose (40 mg/kg BW) of HN-S7A (FIG. 16A, CP+HN: 0.10±0.02 vs CP+HN-S7A: 0.14±0.01, both p<0.05 when compared with CP group: 0.22±0.01). But in middle stages (VII-VIII), HN-S7A had better protective effect than HN (FIG. 16B, CP:

0.33±0.03, CP+HN: 0.32±0.03, CP+HN-S7A: 0.19±0.02, CP Vs CP+HN-S7A p<0.05). Adding HN to HN-S7A+CP had no additional effect both in early+late and middle stages (FIGS. 16A and 16B). HN-C8P on its own had no effect on germ cell apoptosis and showed less protection against CP-induced apoptosis (FIG. 17A, HN-C8P ~30% protection, vs ~60% in HN, p<0.05), and no significant effect in middle (VII-VIII) stages which was similar to HN (FIG. 17B). Adding HN to HN-C8P+CP showed decreased CP-induced apoptosis as CP+HN both in early+late (I-IV and XI-XII) and middle stages (VII-VIII) (FIGS. 17A and 17B).

Phosphorylation of Ser727 and Tyr705 leads to activation of STAT3. Immuno-blot analyses on testis homogenates showed that STAT3 phosphorylation had no significant change with HN or either HN analog treatment under basal conditions in mice (FIGS. 16C, 16D, 17C and 17D). CP treatment suppressed Ser727-phosphorylated STAT3 in testes (p<0.05, FIGS. 16C, 16D, 17C and 17D). HN, HN-S7A, and HN-C8P treatment restored CP-induced Ser 727-phosphorylation of STAT3 (all p<0.05) (FIGS. 16C, 16D, 17C and 17D). Adding HN to the combination of CP+HN-S7A or CP+HN-C8P did not further enhance STAT3 phosphorylation.

Effects of HN Antagonist, HN-L12A, on CP Induced Male Germ Cell Apoptosis

Figure 18A:
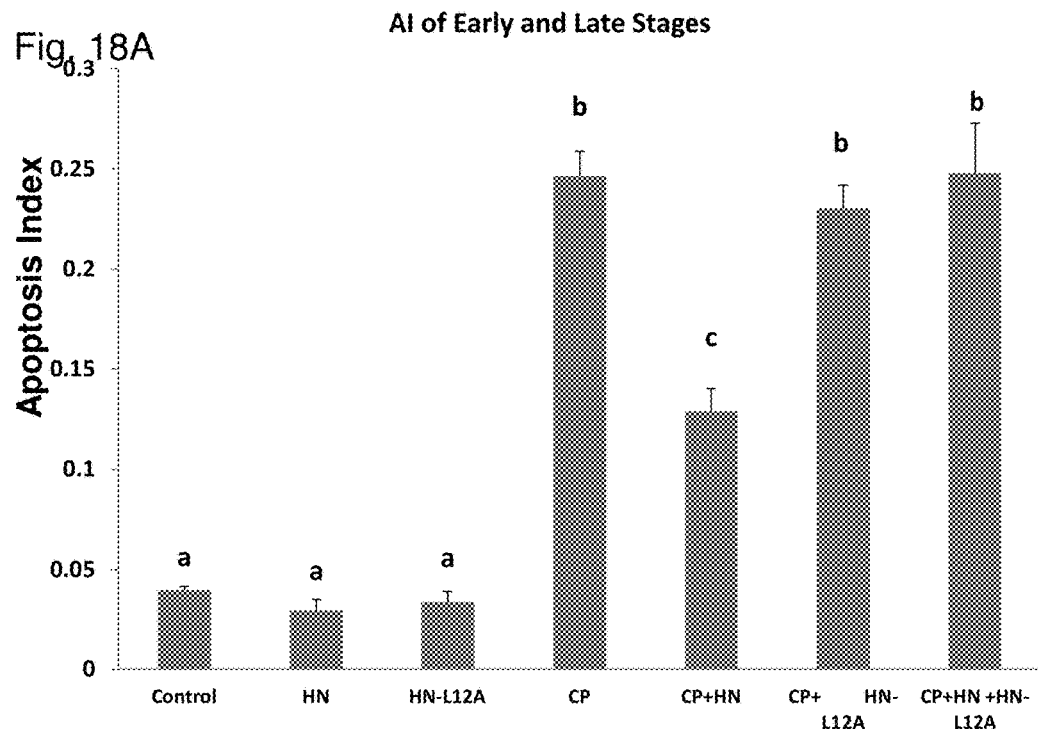
FIGS. 18A-18B show the effect of HN and HN-L12A on Cyclophosphamide-induced male germ cell apoptosis. Mice were treated with vehicle (Control), HN, HN-L12A, CP, CP+HN, CP+HN-L12A, or CP+HN+HN-L12A as described in experimental procedures (n=5 each group). Apoptotic cell numbers were determined by TUNEL staining method. HN or HN-L12A alone did not change apoptosis compared with control. Compared with control, CP increased germ cell apoptosis both in early+late (I-IV and XI-XII, FIG. 18A) and middle (VII-VIII, FIG. 18B) stages. CP+HN significantly suppressed CP-induced apoptosis in early+late stages but not in middle stages. CP+HN-L12A showed no preventive effect against CP-induced apoptosis in neither early+late or middle stages. CP+HN's preventive effect was completely blocked by CP+HN+HN-L12A. Values are means±SEM. Means with unlike superscripts (e.g., a, b and c as shown above the histograms) are significantly different (P<0.05).
Figure 18B:
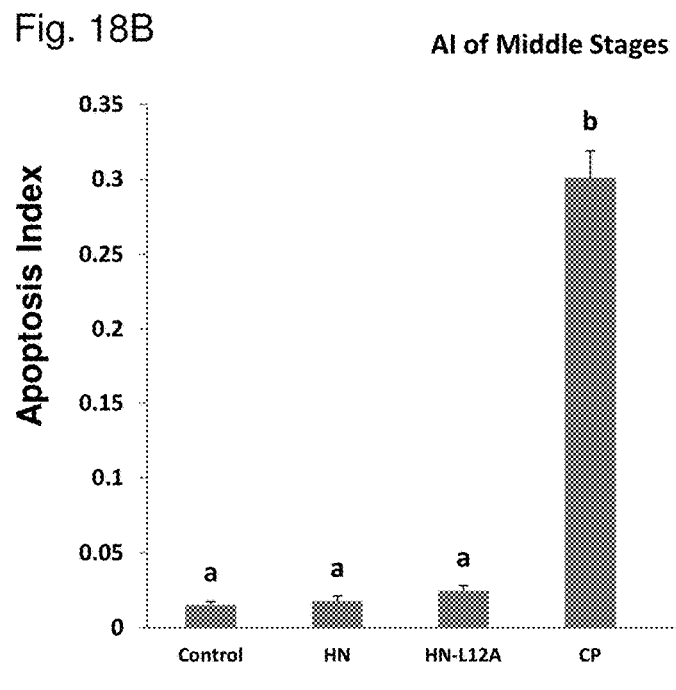

Synthetic HN analog HN-L12A alone did not change the spontaneous germ cell apoptosis. CP-induced germ cell apoptosis was significantly (~57%) inhibited by HN administration (40 mg/kg BW) in early+late stages (stages I-IV and XI-XII) (FIG. 18A, upper panel, AI of CP+HN: 0.13±0.01, p<0.05 compared with AI of CP group: 0.25±0.01), but not in middle stages (VII-VIII, FIG. 18B). HN-L12A was unable to rescue the CP-induced germ cell apoptosis either in middle (VII-VIII) or early+late stages (I-IV and XI-XII) (FIG. 18). Adding HN-L12A at the same dose as HN (40 mg/kg BW) completely blocked the preventive effect of HN against CP-induced germ cell apoptosis in early+late stages (I-IV and XI-XII) (FIG. 18A, CP: 0.25±0.01, CP+HN: 0.13±0.01, CP+HN+HN-L12A: 0.25±0.03). The blocking effect of HN-L12A on HN action was not shown in middle stages (VII-VIII, FIG. 18B) because HN and HN-L12A had no effect of apoptosis in the middle stages.

Discussion

Infertility and sub-fertility are among the most common long-term side effects of chemotherapy. Studies in men and rodents show that chemotherapy can result in decreased sperm count and reproductive capacity (Marcon L, et al., 2008; Meistrich M L., 2009; Delbes G, et al., 2010; Dohle G R, 2010; Trost L W, et al., 2010). Increased survival with modern chemotherapeutics has elevated the expectation of fertility preservation in cancer survivors (Lee S H, et al., 2013). CP and DOX are two drugs which are commonly used in the treatment of cancers, either alone or in combination with other chemotherapeutic agents. These medications induce cancer cell apoptosis but also damage testicular germ cells (Hashimoto Y, et al., 2004). By treating cultured mouse seminiferous tubule with DOX, it was demonstrated that HN significantly reduced doxorubicin induced germ cell apoptosis ex vivo. CP has been used in well characterized animal models to study the adverse effects on male germ cells (Cai L, et al., 1997). HN significantly reduced CP-induced germ cell apoptosis in mice mainly in the early and late stages of the seminiferous tubule epithelium. Thus, HN prevents chemotherapeutic agents-induced male germ cell apoptosis.

Recently, a putative trimetric receptor (with three components: CNTFRα, IL-27 receptor WSX-1, and gp130) was found on the neuronal cell membrane that mediates the neuro-protective activity of HN via the STAT3 pathway (Hashimoto Y, et al., 2005, Hashimoto Y, et al., 2009; Matsuoka M, et al., 2010). WSX-1 and gp130 (but not CNTFRα) and downstream activation of STAT3 is critical for HN-induced anti-apoptotic effects in male germ cells. In this study, CP induced male germ cell apoptosis in vivo by reducing pSTAT3 in the testis and HN restored the CP-suppressed STAT3 phosphorylation. This is consistent with the finding that HN reduced heat or GnRH-A-induced apoptosis by reversing the heat or GnRH-A induced suppression of STAT3 phosphorylation (Jia Y, et al., 2013). These data support that the STAT3 phosphorylation pathway is one of the mechanisms for anti-apoptotic effect of HN in male germ cells. The ubiquitous expression of STAT3 in the testis suggests that the action of HN might not only target germ cells.

In present study, the mechanisms of the protective effect of HN were explored by using different HN analogs. HN has 24 amino acids and one amino acid change modifies its function (Yamada M, et al., 2008). For example, HNG (change of the 14th amino acid from serine to glycine, HN-S14G) is more potent than HN in preventing cell damage (Kunesová G, et al., 2008; Miao J, et al., 2008; Yamada M, et al., 2008). Using 1/8 the dose of HN by injection, HNG showed similar cytoprotective effect against CP-induced germ cell apoptosis as HN, indicating that HNG is more potent than HN in vivo. This finding is consistent with the notion that HNG has greater protective effects on neuronal cells or tissues than HN. Double amino-acid substituted analog HNG-F6A does not bind IGFBP-3 (Ikonen M, et al., 2003). The present study showed HNG-F6A and HNG had similar protective effects against CP-induced germ cell apoptosis at equivalent doses, indicating that the cytoprotective effects of HN and its more potent analogs on male germ cells is unrelated to its binding to IGFBP3. This is similar to analogous experiments showing that HNG-F6A and HNG increases glucose stimulated insulin secretion to a similar extent in both isolated islets/cell culture and whole animals (Kuliawat R1, et al., 2013).

The sequence motif from Pro3 to Pro19 forms the core domain of the 24 amino acid sequence of HN. Within the core domain, each amino acid, Pro3, Cys8, Leu9, Leu12, Thr13, Ser14, and Pro19, but not Ser7, have been found to be essential for the neuro-protective function of HN (Hashimoto Y, et al., 2001; Hashimoto Y, et al., 2001). HN-S7A is a dimerization-defective mutant, i.e. HN-S7A does not self-dimerize and does not dimerize with HN. HN-S7A has no cytoprotective effect in neuronal cells in vitro indicating that the self-dimerization process is essential for HN's neuro-protective function culture (Yamagishi Y, et al., 2003). In one in vivo experiment, HN-S7A was effective in preventing CP-induced germ cell apoptosis but did not affect the ability of HN to protect CP-induced male germ cells apoptosis suggesting that the self-dimerization process may not be critical for HN's cytoprotective effect in testis in vivo. Thus the loss of the cytoprotective effect of HN-S7A in neuron cell culture experiments were not replicated in vivo mouse experiments. The action of HN-S7A may be different in vitro versus in vivo where interactions with HN-S7A may enhance its activity. Three components (CNTFRα, WSX-1, and gp130) of a humanin receptor were found on the neuronal cell membrane that mediates the neuro-protective activity of HN. Only WSX-1 and gp130 (but not CNTFRα) are critical for HN-induced anti-apoptotic effects in male germ cells. The assembly of different subunits of membrane receptor of HN in testis may be one of the reasons that self-dimerization may not be necessary for HN's effect in testis as that in neuron. HN-S7A suppressed CP-induced male germ cell apoptosis both in early+late (stages I-IV and XI-XII) as well as middle stages (VII-VIII), while HN only suppressed CP-induced apoptosis in early+late but not in middle stages. This suggests that HN-S7A may have additional mechanism for protecting male germ cells which require further identification. Western blot analyses showed both HN and HN-S7A restored the CP-suppressed STAT3 phosphorylation supporting that the mechanism of the cyto-protective effects of HN and HN-S7A is mediated through the IL6-like trimeric membrane receptor.

Cysteine at position 8 is an amino acid essential for HN's neuro-protective function (Hashimoto Y, et al., 2001; Guo B, et al., 2003; Hashimoto Y, et al., 2001; Sponne I, et al., 2004; Zhai D, et al., 2005; Zhai D, et al., 2005; Arakawa T, et al., 2008; Arakawa T1, et al., 2011). HN-C8P does not bind with BAX and shows no anti-apoptotic effects in cell culture (Guo B, et al., 2003; Yamagishi Y, et al., 2003). In vivo HN-C8P partially prevented CP-induced germ cell apoptosis but was less potent than HN. This finding indicates the intracellular binding to BAX may play a role, but not a major part, in protective effect of HN in CP-induced germ cell death which is consistent with previous observations (Jia Y, et al., 2013). Western blot showed that HN-C8P restored the CP-suppressed STAT3 phosphorylation which suggests but does not prove that the mechanism of HN-C8P's protective effect may be through membrane receptor.

The sequence motif from Leucine 9 to Leucine 12 plays a functional role as a hydrophobic core of the HN peptide (Hashimoto Y, et al., 2001; Yamagishi Y, et al., 2003; Hashimoto Y, et al., 2001). Although replacement of Leu12 with Alanine does not attenuate HN's secretory activity, HN-L12A lacks the ability to bind with membrane receptor and has no anti-apoptotic effect in cell culture (Yamagishi Y, et al., 2003). HN-L12A dimerizes with HN prevents its binding to the receptors acting as a HN antagonist. In the present study, HN-L12A did not prevent CP-induced germ cell apoptosis but completely blocked the cytoprotective effect of HN against CP-induced male germ cell apoptosis at similar dose of HN. These results indicated that membrane receptor binding ability is important for HN and HN analogs cytoprotective activity. Published data from other investigators showed that HN-S7A and HN-C8P had no cytoprotective effect in vitro (Hashimoto Y, et al., 2001; Yamagishi Y, et al., 2003; Hashimoto Y, et al., 2001), while these two HN analogs partially protected male germ cell from CP-induced apoptosis in vivo. The contrasting effects of HN analogs (such as HN-S7A and HN-C8P) in vitro and in vivo suggest that HN and HN analogs may be modified in vivo or may act through different pathways or systems (e.g. IGF-1 pathway, (Yen K, et al., 2013)) instead of directly affecting the target cells or organs. Arakawa et al studied the biological activity and structural stabilities of HN analogs. Theses investigators also concluded that different biological activities of HN analogs could not be explained only by one simple factor (e.g. the structure stabilities) (Arakawa T1, et al., 2011). HN prevents male germ cell apoptosis induced by different stress mainly by binding to the putative membrane receptor and STAT3 pathway but HN also binds extra-cellularly to IGFBP-3 (Miao J, et al., 2008; Jia Y, et al., 2010) or intra-cellularly to BAX (Guo B, et al., (2003); Zhai D, et al., 2005; Jia Y, et al., 2010), thus the mechanism of HN's anti-apoptotic effect in male germ cell is complex and may act through multiple pathways including in vivo modification of HN and its analogs. Understanding of the mechanisms of HN action may help to design specific targets that may be used for drug development, e.g. agonists that protect male germ cells from stress-induced death (e.g. testicular hyperthermia, hormonal deprivation, or chemotherapy). In present study, the germ cells undergoing apoptosis were mainly pachytene spermatocytes and round spermatids. Apoptotic spermatogonia were not observed likely due to the short duration of exposure to CP (12 hours ex vivo and 24 hours in vivo). Male germ cells at different stages of the seminiferous epithelium have different mechanisms regulating the balance between apoptosis/survival homeostasis. Germ cells in early+late stages in acute experiments are more susceptible to heat stress than those middle stage germ cells; while middle stages germ cell apoptosis could be induced by testosterone deprivation (Lue Y H, et al., 1999; Lue Y, et al., 2006; Jia Y, et al., 2007). In the present study, HN showed preventive effects against CP induced apoptosis in early+late but not in middle stages most likely because of the protective effect of intratesticular testosterone present in the middle stages. If the testis were examined after longer exposure to CP, it is expected that the early+late stage apoptosis will progress to involve middle stage germ cells.

In summary, it was demonstrated that 1) HN significantly prevents male germ cell apoptosis induced by chemotherapeutic agents both ex vivo and in vivo; 2) the anti-apoptotic effect of HN, HN-S7A, and HN-C8P on CP-induced male germ cell apoptosis is mainly mediated through the cell membrane receptor and downstream STAT3 pathway; 3) lack of IGFBP-3 binding ability does not neutralize HNG's cytoprotective effect in testis; 4) self-dimerization may not be necessary for HN preventing CP-induced germ cell apoptosis in vivo; 5) BAX-binding pathway may also play a role in HN's protective effect; 6) HN-L12A is an antagonist to HN preventing its cytoprotective effect in germ cell apoptosis in vivo. HN may be an important molecule in the regulation of germ cell homeostasis and may have roles in male infertility and prevention of chemotherapy-induced onco-infertility (Jia Y, et al., 2010).

Example 3: HNG Enhances Tumor Suppression by a Chemotherapeutic Agent CP

Figure 19:
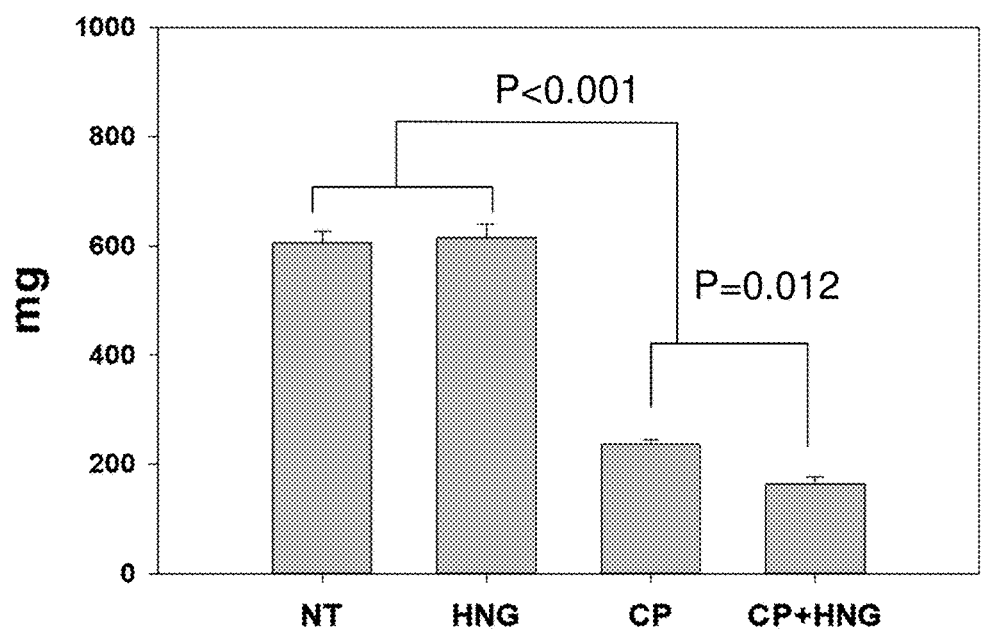
FIG. 19 shows HNG enhanced CP-induced suppression of mammary tumor. Mice bearing 4T1 mammary cancer were treated for 14 days with HNG (5 mg/kg/day), CP (100 mg/kg), HNG+CP or nothing (NT). Mammary tumor weight is shown on the y-axis.

A mouse mammary cancer model was used which utilizes 4T1 cells transfected with the luciferase gene. Growth and size of 4T1 mammary tumors were detected by bioluminescence imaging (IVIS Luminia II, Perkin Elmer, Waltham, Mass.). Mice (n=5 to 7 per group) were inoculated with $1 \times 10^6$ 4T1 cells into the right third mammary gland, and 7 days later they were left untreated or treated with HNG (5 mg/kg/day IP), CP (100 mg/Kg single IP) or HNG+CP for 14 days. Bioluminescence imaging was conducted at days 7 and 12. Animals were sacrificed and tumors were removed on day 14 after the start of treatment. Mammary tumors were smaller in CP and CP+HNG groups compared to the untreated and HNG-treated animals (Data images not shown). Mammary tumors removed from untreated and HNG-treated mice were larger and heavier than the tumors in the CP and CP+HNG group (p<0.001). Mean tumor weight was also significantly lower in the HNG+CP compared to CP treated mice (p<0.012) (FIG. 19). This experiment showed that HNG enhanced the CP-induced suppression of 4T1 mouse mammary cancer growth.

Example 4: HNG Protects Ovaries from Chemotherapy-Induced Damage

Figure 20:
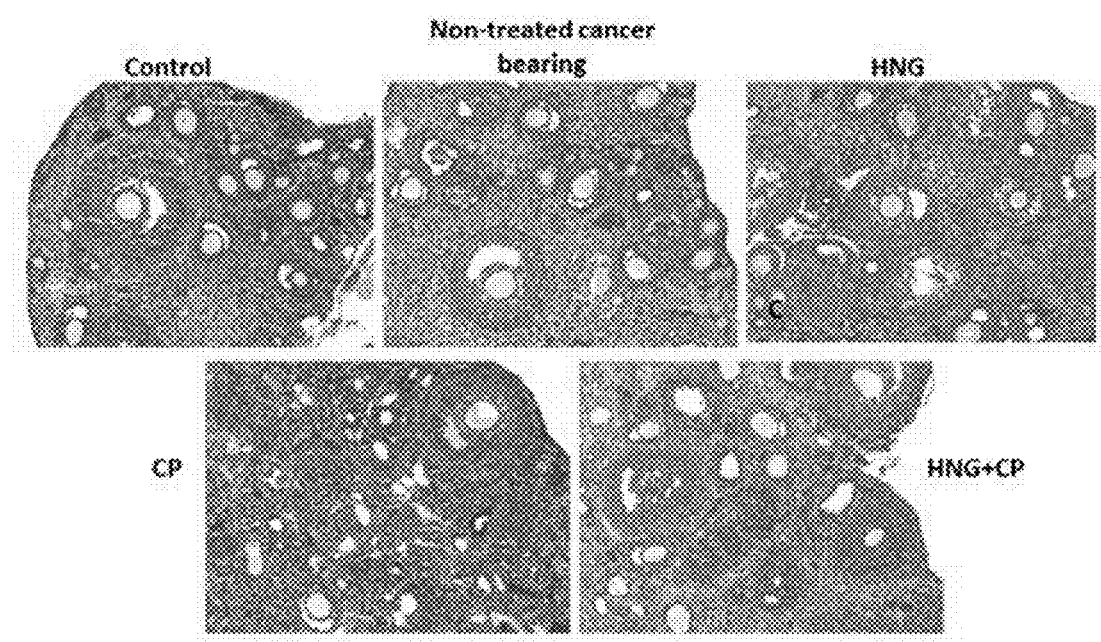
FIG. 20 shows a photomicrograph of ovaries obtained from young mice (control), 4T1 mammary cancer bearing mice were not treated, or treated with HNG (5 mg/kg/day), CP (100 mg/kg IP), HNG+PC (Hematoxyline & Eosin, scale bar=100 micrometers).

A mouse mammary cancer model was used which utilizes 4T1 cells transfected with the luciferase gene. Growth and size of 4T1 mammary tumors were detected by bioluminescence imaging (IVIS Luminia II, Perkin Elmer, Waltham, Mass.). Mice (n=5 to 7 per group) were inoculated with $1\times10^6$ 4T1 cells into the right third mammary gland, and 7 days later they were left untreated or treated with HNG (5 mg/kg/day IP), CP (100 mg/Kg single IP) or HNG+CP for 14 days. Animals were sacrificed and both ovaries were removed from each mouse on day 14 after the start of treatment. Serial 5-micrometer sections were made. Every 5th section was examined and the number of primordial, primary, and secondary follicles counted (Kim S Y, et al., 2013; Bristol-Gould S K, et al., 2006; Roti Roti E C, et al., 2012). In addition, TUNEL staining for apoptotic cells and oocytes was quantified (Perez G I, et al., 1997; Ben-Aharon I, et al., 2010). Representative sections of ovaries showed that control, non-treated tumor-bearing, and HNG treated mice have many primary, secondary, and antral follicles, whereas as CP treated ovaries have less secondary, but more atretic follicles. HNG treatment appeared to reverse the CP-induced decrease in follicles (FIG. 20).

Example 5: Humanin May be a Caloric Restriction Mimetic and can Decreases IGF

Obesity increases the risks of developing breast cancer and recurrence of the cancer (Biglia N, et al., 2013; Garrisi V M, et al., 2012; Kamineni A, et al., 2013; Simpson E R, et al., 2013). Caloric restriction is associated with longevity, resistance to stress, and postponement or attenuation of cancer growth, immunosenescence, and inflammation without permanent side effects across species (Bar-Joseph H, et al., 2010; Desai V G, et al., 2013, Doroshow J H, et al., 1983; O'Brien P J, et al., 1997; Ottewell P D, et al., 2008). A long-term low-fat diet in the Women's Health Initiative did not result in a reduction in breast cancer risk. The reduction of fat intake after 6 years was only 8.1%, well below the goal of fat intake of 20%, indicating that long-term adherence to diet restriction is difficult to maintain (Chlebowski R T, et al., 1993; Prentice R L, et al., 2006). The life-prolonging effects of caloric restriction are most likely related to decreased IGF-1 levels (Ottewell P D, et al., 2008). Mice and men deficient in GH, GH receptor, IGF-1, or IGFR are less susceptible to stress, are protected against age-related diseases including diabetes and cancer, and have longer life span (Ewans A, et al., 2006; Mayle A, et al., 2013; Rundberg Nilsson A, et al., 2013). Lowering IGF-1 levels can result in inhibition of tumorigenesis (Schlueter A J, et al., 2001; Jimenez M, et al., 2005; Sun X, et al., 2001; Panosyan E H, et al., 2014).

Figure 21:
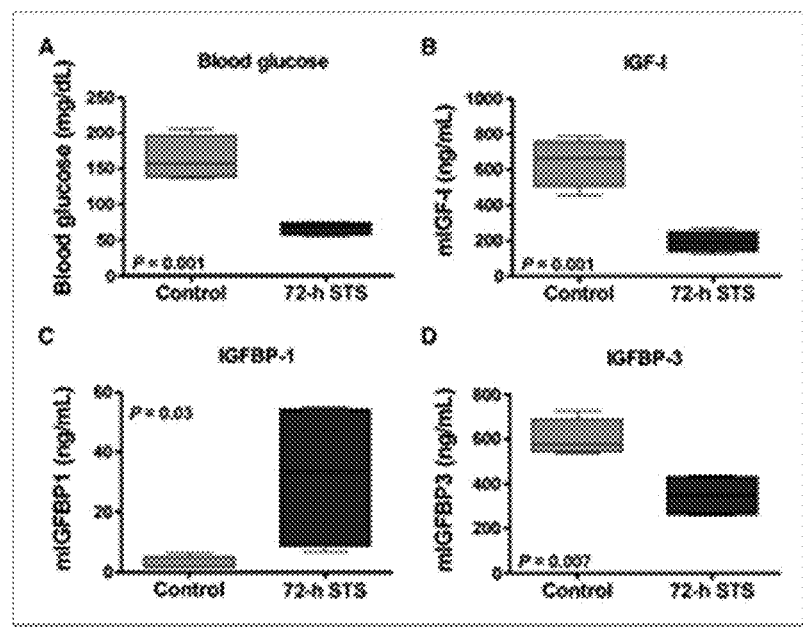
FIG. 21 shows blood levels (y-axis) of glucose, IGF-1, IGFBP-3 and IGFBP-1 in 30-week-old mice before (Control) or after 72 hours fasting (72 h-STS).
Figure 22:
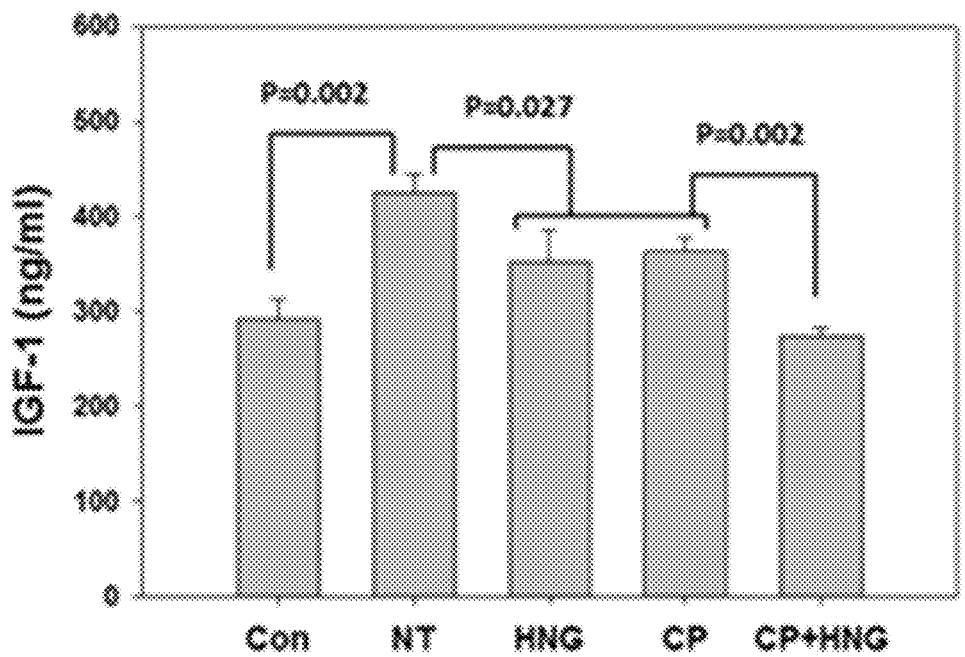
FIG. 22 shows plasma levels of IGF-1 (y axis) in mice bearing metastatic lung melanomas (NT not treated; or treated for 14 days with HNG 5 mg/kg/day IP, CP 200 mg/kg IP single injection; or HNG+CP).
Figure 23:
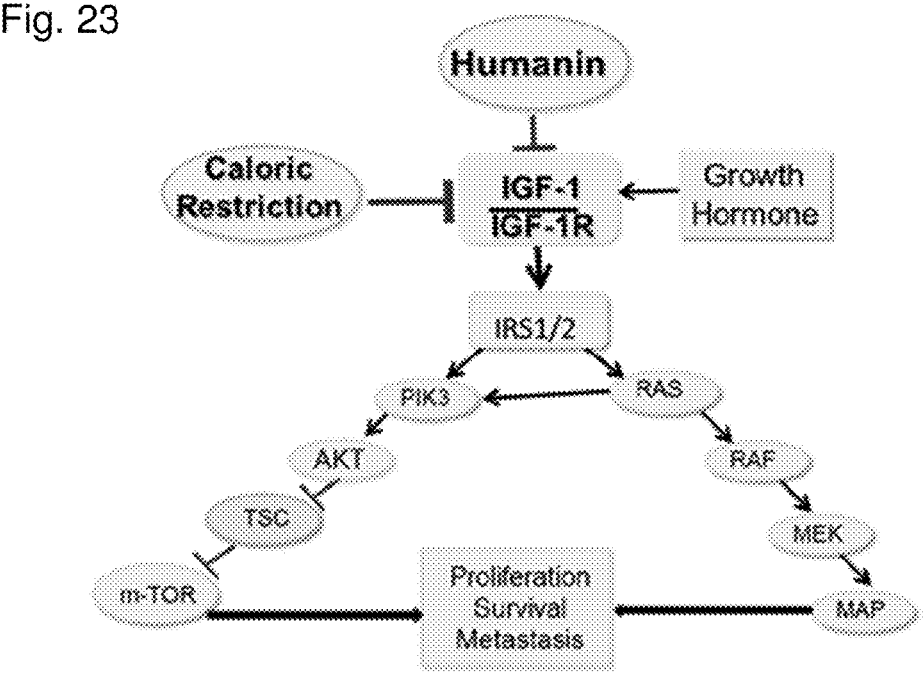
FIG. 23 shows a proposed theory of HN action in cancer where HN mimics caloric restriction and decreases IGF-1 inhibiting downstream signaling of PI3K-Akt-mTOR and RAS-RAF-MEK leading to suppression of proliferation, survival, and metastasis.

After 72 hours of fasting, mice demonstrated lower glucose, IGF-1, and IGFBP-3 levels and increased IGFBP-1 levels (FIG. 21) with slight but non-significant increases in GH and minimal increases in insulin (Goel S, et al., 2013). Mice bearing metastatic melanoma, exogenous HNG alone or CP alone modestly suppressed IGF-1 but HNG+CP further suppressed IGF-1 levels (FIG. 22). Without being limited to theory, the suppression of IGF-1 suggests that HNG may suppress tumor growth via the IGF-1 signaling pathway (RAS/RAF/MAPK and PI3K/Akt/m-TOR) mimicking caloric restriction pathways resulting in tumor growth suppression (FIG. 23). These preliminary data support a concept that HN is a caloric restriction mimetic, and its cytotoxic effects in cancer may be mediated by lowering IGF-1 without increasing GH and insulin.

Example 6: HNG Reduces Cyclophosphamide (CP)-Induced Germ Cell Apoptosis

Figure 24:
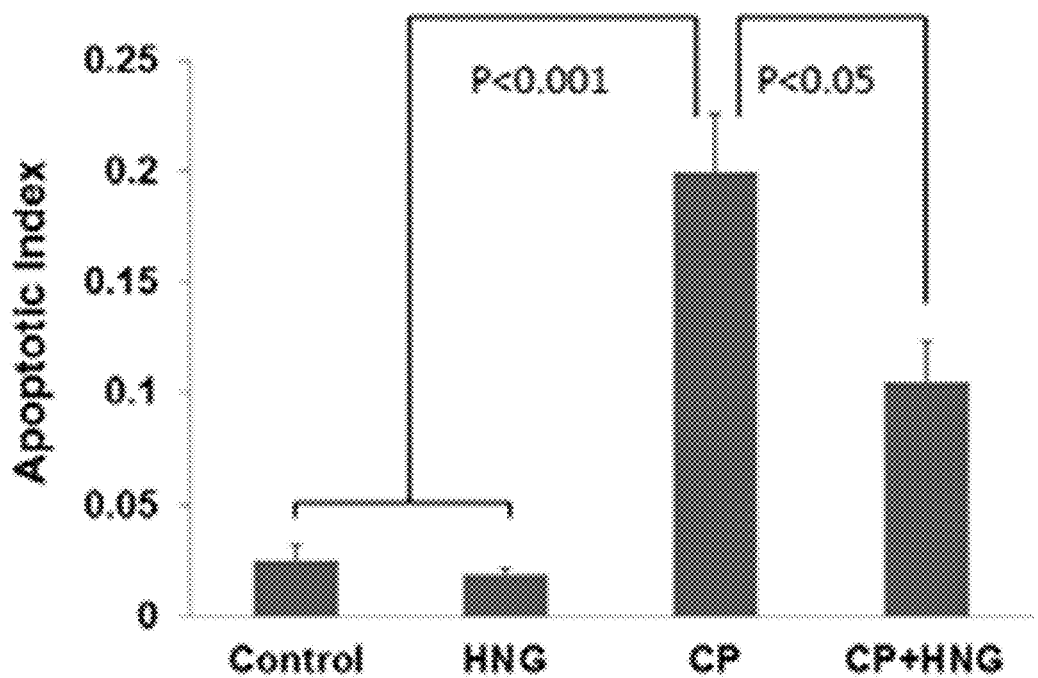
FIG. 24 shows apoptosis of germ cells in mice (apoptotic index, y-axis) treated with HNG, CP, or CP and HNG (CP+HNG). HNG decreased CP-induced germ cell apoptosis in mice. Apoptotic index: # apoptotic cells/Sertoli cell.

Chemotherapeutic agents on mouse germ cells, a single dose of cyclophosphamide (CP) at 200 mg/kg causes significant apoptosis of mouse germ cells after 24 hours. To examine the protective effects of HNG on germ cells, adult mice were treated with vehicle (control); HNG (5 mg/kg/BW, intraperitoneal injection IP); CP (200 mg/kg/BW, IP); and CP+HNG for 24 hours. CP treatment significantly increased germ cell apoptosis in all stages of spermatogenesis (P<0.001). HNG alone had no effect, but HNG significantly decreased CP-induced apoptosis (p<0.05) (FIG. 24).

Example 7: The Mitochondrial Peptide Humanin (HN) is a Potent Inducer of Autophagy In several cell types including HEK293 (normal embryonic kidney cells), SH-SY5Y (neuroblastoma), and B16 (melanoma), HN induces autophagy. The increased level of LC3-II, a marker of autophagosome was examined by Western blot and immunocytochemistry. The increase of autophagosomes and autolysosomes in HEK293 cells stably expressing mRFP-GFP-LC3, a dual-tag reporter of autophagy, was examined following humanin treatment. In addition, the signaling pathways activated by humanin using a phospho-antibody array in SH-SY5Y cells was investigated. This revealed several pathways known to regulate autophagy. Both activation and suppression of autophagy are involved in cancer pathogenesis and treatment, depending on the context.

This study was designed to determine the synergistic/additive effect of humanin on the efficacy of doxorubicin in B16 melanoma cells in culture and more specifically, to reveal whether autophagy is involved in this combination strategy. Fluorescent microscopy and western blot of LC3-II confirmed that the potent humanin analog, HNG, increased autophagy in B16 cells. The combined treatment caused an additive effect on the cytotoxicity versus doxorubicin treatment alone. In addition, inhibiting autophagy by treating cells with autophagy inhibitors, including 3-MA and chloroquine, diminished the additive effect of humanin in doxorubicin treated B16 cells. Taken together, the current study suggests that humanin has direct effects on tumor cells that involves induction of autophagy and thus humanin acts as a chemotherapeutic augmenter and synergistically enhances doxorubicin's anticancer effects. Furthermore, the autophagy induction of humanin may be related to its apparent effects of enhancing longevity observed in other systems.

Figure 25:
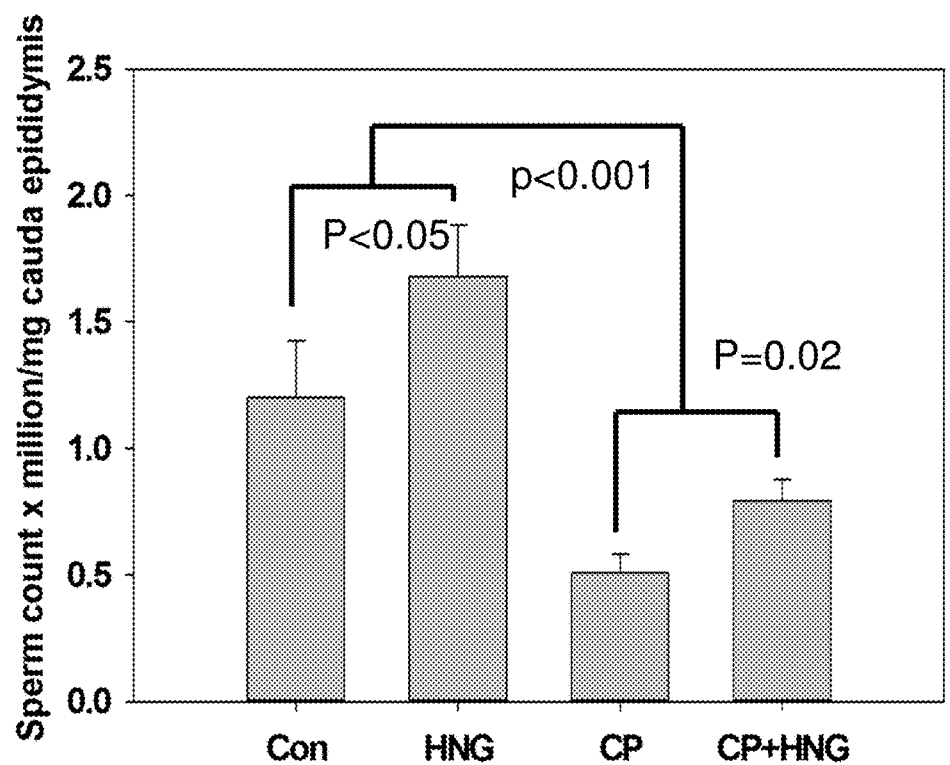
FIG. 25 shows the sperm count (y axis) in Cauda Epididymis from mice treated with repeated CP, HNG or CP and HNG injections (CP+HNG) compared to untreated controls (Con).

Example 8: The Mitochondrial Peptide Analog HNG Protects Against Cyclophosphamide-Induced Decrease in Sperm Output The objective of this study was to investigate whether HNG has protective effect on sperm output after multiple doses of CP in mice. Thirty adult male mice (C57BL/6J) were randomized into 4 groups: 1) 5 as control; 2) 5 received daily subcutaneously injection of HNG (10 mg/kg BW); 3) 10 were given 6 doses of CP (150 mg/kg BW) intraperitoneally at 5-day intervals; 4) 10 received both HNG and CP. All mice were killed at 28 days. Plasma HNG and IGF-1 levels were measured by ELISAs. The cauda epididymal sperm count was performed using a hemocytometer. Plasma HNG levels increased significantly (p<0.001) in HNG treated (80.8±7.8 ng/ml), and HNG+CP treated (64.7±1.8 ng/ml) mice compared to control (1.3±0.1 ng/ml), and CP treated mice (1.7±0.1 ng/ml). Compared to control (413.7±44.9 ng/ml), plasma IGF-1 levels were significantly (p<0.001) suppressed by HNG (347.2±20.1 ng/ml), CP (182.4±10.5 ng/ml), and further suppressed by CP+HNG treatment (148.8±8.1 ng/ml). Epididymal sperm counts were significantly elevated by HNG (1.7±0.2×10$^6$/mg, p=0.04), and significantly suppressed by CP (0.5±0.1×10$^6$/mg, p<0.001) as compared to control (1.2±0.2×10$^6$/mg) (FIG. 25). HNG+CP significantly increased sperm count (0.8±0.1×10$^6$/mg, p=0.02) as compared to CP. It was concluded that HNG prevents CP-induced suppression of sperm output. These findings suggest that HNG is a promising adjuvant to chemotherapy by preventing onco-infertility.

Example 9: Adenosine Monophosphate-Activated Protein Kinase (AMPK) Pathway May be Involved in HNG Treatment in Pulmonary Mouse Metastatic Melanomas Background: Humanin (HN) is a mitochondrial derived peptide with cytoprotective effects in normal cells challenged by various stressors. As shown herein, the potent synthetic HN analog (HNG, HN-S14G) attenuates male germ cell apoptosis induced by cyclophosphamide (CP) treatment in rodents while suppressing CP-induced tumor growth in a mouse lung B16 melanoma metastasis model. HNG has been shown to activate several signal transduction pathways, including promoting AMPK signaling. It was hypothesized that a possible mechanism for HNG enhanced chemotherapy-induced tumor suppression is by changing the energy/nutrient availability by activating AMPK, and suppressing mTOR (mammalian target of rapamycin) dependent pathway.

Methods: Adult male mouse (n=5/group) were seeded with mouse B16 melanoma cells (100,000 cells/mouse) via tail vein on day 1. One week after melanoma cell inoculation, mice were treated either with a single intraperitoneal injection (IP) of CP (200 mg/kg), or daily IP injections of HNG (5 mg/kg), or both for 14 days. Mice were sacrificed at day 21 and lungs were fixed in formaldehyde. Immunohistochemistry was performed on lung metastases with antibodies against phosphorylated-AMPK (p-AMPK), p-4E-BP1 (downstream effector of mTOR) and Ki-67 antigen (a marker of cell proliferation).

Results: Compared to non-treated mice, HNG decreased number of metastatic lung tumors by ~23%, CP by ~50% and HNG+CP by ~61%. The percent p-AMPK positive cells in metastatic lung melanoma treated with HNG alone (40.3±10.7, mean±SD) and HNG+CP (38.0±13.0) were significantly increased compared to CP alone (11.3±15.6, p<0.22). Expression of mTOR downstream effector for proliferation, p-4E-BP1, within the metastatic tumors was very variable and not significantly different among groups. The mean Ki-67 index was significantly lower (p=0.0036) in CP treated (30.0±16.2) and CP+HNG groups (35.8±12.8), compared to untreated (62.0±14.8) and HNG groups (60.0±14.1SD). Co-administration of HNG with CP did not appear to further inhibit Ki-67 index.

Conclusion: HNG activates the key energy homeostasis regulator AMPK without affecting tumor mTOR signaling. The residual tumor cells that survived chemotherapy may have adapted to energy deprivation. AMPK activation may initially lead to mTORC1 (mTOR complex 1) inactivation, followed by mTORC2 mediated reactivation of mTORC1 resulting in increased p-AMPK with no detectable change in p-4EBP1 expression in the tumor after CP±HNG treatment. Other pathways may also be involved to antagonize the inhibition of mTOR by AMPK in the tumor. This suggests that AMPK activation may be sufficient to reduce tumor growth without mTOR suppression. Importantly HN may have differential actions by modulating the host via both AMPK and mTOR pathways mimicking reduced nutrient availability in caloric restriction but increase AMPK signaling only in the tumor.

Figure 26:
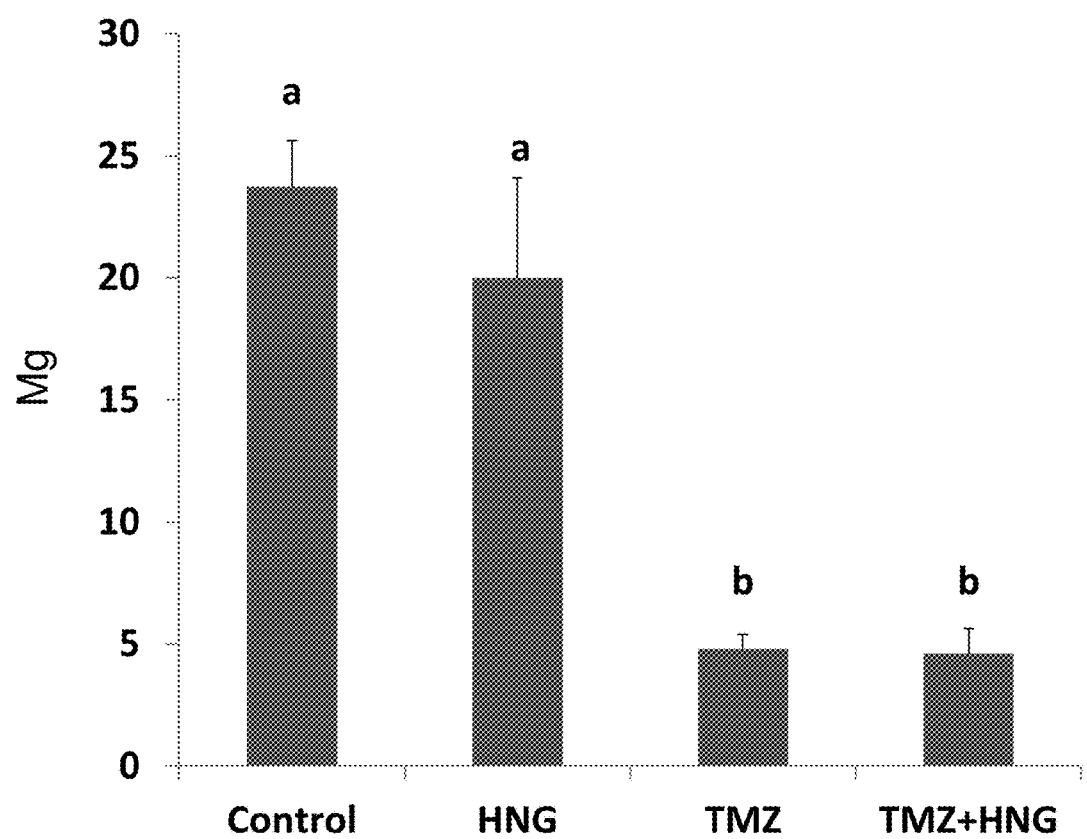
FIG. 26 shows tumor weight of human medulloblastoma (DAOY) tumors removed 26 days after implantation into the right flank of SCID mice treated with nothing (control), HNG, Temozolomide (TMZ) or TMA and HNG (TMZ+ HNG).
Figure 27A:
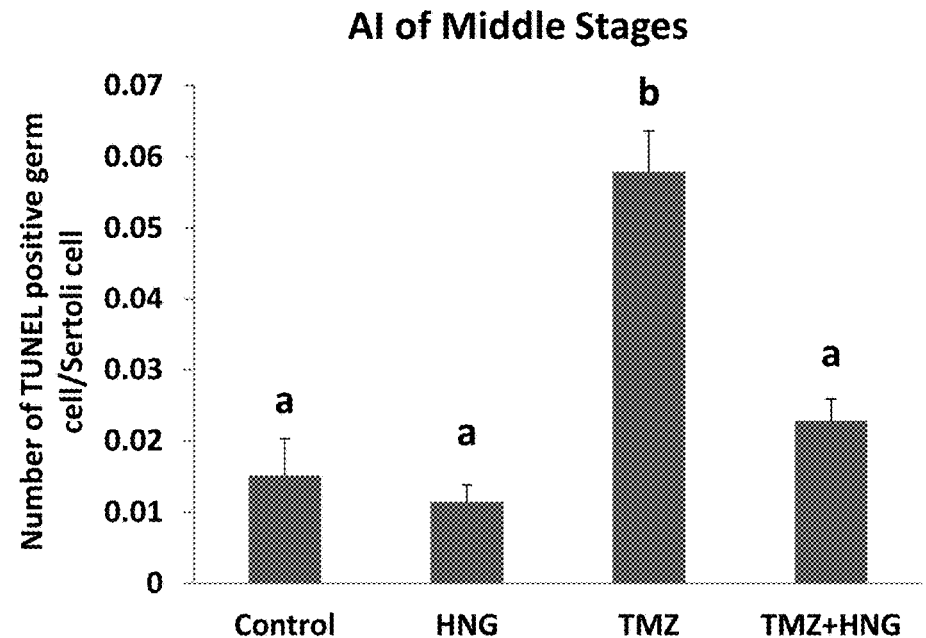
FIGS. 27A-27B show the effect of HN and HN-L12A on TMZe-induced male germ cell apoptosis in middle stages (FIG. 27A) and early-late stages (FIG. 27B). Mice were treated with vehicle (Control), HNG, TMZ or TMZ and HNG (TMZ+HNG) as described in experimental procedures (n=5 each group). Apoptotic cell numbers were determined by TUNEL staining method. HNG alone had no effect on male germ cell apoptosis, but significantly prevented TMZ-induced apoptosis in both middle stages (FIG. 27A) and early+late stages (FIG. 27B). Values are means±SEM. Means with unlike superscripts (e.g., a and b as shown above the histograms) are significantly different (P<0.05)
Figure 27B:
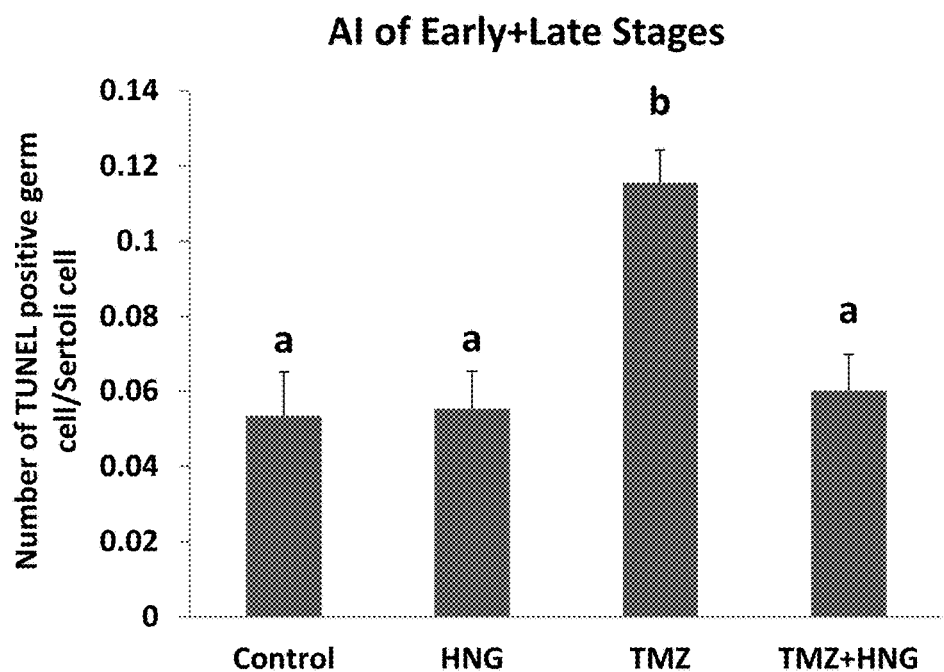

Example 10: Humanin Analog (HNG) Prevents Male Germ Cell Apoptosis Induced by Temozolomide in Severe Combined Immuno-Deficiency (SCID) Mice Bearing Medulloblastoma Onco-infertility is a major concern of cancer survivors. In this study, it was investigated whether HNG will prevent chemotherapy (Temozolomide, TMZ, an alkylating agent used clinically to treat brain tumors) induced male germ cell apoptosis in SCID mice bearing subcutaneous implants of human medulloblastoma. DAOY human pediatric medulloblastoma cells (1.0×10$^8$ cells/animal) were injected subcutaneously into the right flank of 7-week old male SCID mice. After 3 weeks to allow tumor growth, each group of mice (n=4 to 5/group) received one of the following treatments: 1) vehicle (control); 2) HNG intra-peritoneal (IP) injection (HNG, 5 mg/Kg BW/day, 3 days pretreatment +5 days treatment); 3) TMZ IP injection (TMZ, 50 mg/Kg BW/day×5 days); 4) TMZ and HNG IP injections (TMZ+HNG). Mice were sacrificed 24 hours after the last injection, subcutaneous tumors were dissected and weighed (FIG. 26) and male germ cell apoptosis was assessed by TUNEL staining and quantified (Apoptosis Index, AI, number of apoptotic germ cell/Sertoli cell, FIG. 27). TMZ markedly suppressed tumor growth (FIG. 26); addition of HNG did not alter the marked suppression of tumor growth by TMZ. HNG alone had no effect on male germ cell apoptosis, but significantly prevented TMZ-induced apoptosis in both middle stages (TMZ 0.058±0.006, TMZ+HNG 0.023±0.003, p<0.05, FIG. 27A) and early+late stages (TMZ 0.116±0.009, TMZ+HNG 0.060±0.010, p<0.05, FIG. 27B). HNG ameliorated TMZ-induced germ cell apoptosis without affecting the chemotherapeutic effect on transplanted medulloblastoma tumor in an immunocompromised mouse model. This data indicates that HN and its analogs may be used as supportive therapy to preserve fertility.

Example 11: Humanin Protects Against Chemotherapy-Induced Stage Specific Male Germ Cell Apoptosis in Rats Experiments were performed herein to examine whether HN has protective effects on chemotherapy-induced male germ cell apoptosis and to investigate whether the protective effect of HN on germ cells require the presence of Leydig cells. The results show that HN decreased CP and/or EDS-induced germ cell apoptosis in a stage-specific fashion. HN acted directly on germ cells to protect against EDS induced apoptosis despite depletion of Leydig cells and low intratesticular testosterone level in adult rats.

Materials and Methods

Animals

Young adult (3-month-old) male Sprague Dawley rats used for the in vivo and in vitro studies were purchased from Charles River Laboratories (Wilmington, Mass., USA) and housed in a standard animal facility under controlled temperature (22° C.) and photoperiod of 12 h of light and 12 h of darkness with free access to food and water. The animal use protocol was reviewed and approved by the Institutional Animal Care and Use Committee of Los Angeles Biomedical Research Institute at Harbor-UCLA Medical Center.

Experiment A. The Effects of HN on Chemotherapy-Induced Male Germ Cell Apoptosis with or without Pre-Treatment with EDS to Deplete Leydig Cells in Rats Thirty two young adult (60-day-old) male rats were randomly divided into 8 groups with 4 rats per group. To examine the effects of HN on CP-induced male germ cell apoptosis, four groups of rats were treated with 1) vehicle (control); 2) a single intraperitoneal (IP) injection of HN (40 mg/kg BW) (synthesized by CP scientific, Sunnyvale, Calif.); 3) a single IP injection of CP (Cyclophosphamide Monohydrate, 70 mg/kg BW, Sigma, St. Louis, Mo.); or 4) CP+HN to rats. To determine whether Leydig cells were involved in the cytoprotective action of HN on germ cell apoptosis, 4 groups of rats were pre-treated with IP injection of ethane dimethanesulfonate (EDS, 80 mg/kg) to eliminate Leydig cells. EDS was a gift from M. Meistrich, PhD, MD Anderson Cancer Center. EDS was synthesized by the M.D. Anderson Translational Chemistry Core Facility under the direction of Dr. William Bornmann. After 3 days, when depletion of Leydig cells occurred (Morris et al, 1997), a single IP injection of vehicle (control); HN; CP; or HN+CP to 4 groups of EDS pre-treated rats was administered. Twelve hours after treatment, all rats were injected with heparin (130 IU/100 g BW, i.p.) 15 min before being sacrificed by a lethal injection of sodium pentobarbital (200 mg/kg BW i.p.) to facilitate testicular perfusion using a whole-body perfusion technique (Lue, et al., 2010). Body weight was recorded at autopsy and blood samples were collected from the right ventricle of each animal immediately after death, and plasma was separated and stored at ~20 C for subsequent T measurement. One testis from each animal was snap-frozen in liquid nitrogen. The contralateral testis was then fixed by vascular perfusion with Bouin's solution for 40 min. preceded by a brief saline wash. Testes were removed and placed into the same fixative overnight. One slice from the middle region of Bouin's fixed testis was processed for routine paraffin embedding for histological evaluation and terminal deoxynucleotidyl transferase dUTP nick end labeling (TUNEL) assay (Lue, et al., 2010).

Experiment B. The Effects of HN on Cultured Leydig Cells Treated with Ketoconazole Leydig cells were isolated based on a previously described procedure (Gao, et al., 1996; Klinefelter, et al., 1987; Salva, et al., 2001). Briefly, the testes were decapsulated, and then dissociated with collagenase, dispase, DNase and shaking for 15 min at 34° C. The seminiferous tubules were removed by filtration through 40 μm nylon mesh (BD Falcon, Franklin Lakes, N.J.). Leydig cells were then harvested after centrifugation and purified using a Percoll gradient (GE Healthcare, Uppsala, Sweden) and centrifugation (60 minutes at 20,000 g at 4° C.). Enriched Leydig cells were harvested at densities between 1.065 (red) and 1.075 (blue) g/cm$^3$ from the percoll gradient. These Leydig cells were washed by diluting the percoll and excluding residual germ cells and other cells using a BSA density gradient with centrifugation. The purity of the Leydig cells was >90%, as determined by histochemical staining for 3β-hydroxysteroid dehydrogenase. The cell viability, as assessed by trypan blue exclusion, was greater than 90%. In all the in vitro experiments, 2×10$^5$ purified Leydig cells were added to each well of the 6-well plates in 2 ml Leydig cell culture media (Dulbecco's Modified Eagles Medium (DMEM)-Ham's nutrient mixture F-12 (Life Technologies, Grand Island) containing penicillin and streptomycin (Invitrogen Life Technologies, Inc., Paisley, UK). Eight replicate experiments were performed where Leydig cells were incubated respectively with vehicle (control), HN (10 mcg/ml), KTZ (10 mcg/ml, Sigma Aldrich, St. Louis, Mo.), or KTZ+HN at 34° C. for 4 hours. After treatment, the culture medium from each well was collected and stored at ~20° C. for testosterone measurement.

Immunohistochemistry for Localization of HN in Testes

Endogenous HN localization in rat testes was detected by immunohistochemistry using rat humanin (rattin) specific antibody. In brief, after de-paraffinization and rehydration, testicular sections were first incubated with a rabbit polyclonal anti rat-humanin (rattin) antibody (Abcam, Cambridge, Mass.) at a concentration of 10 mcg/ml at 4° C. overnight and then followed by Alexa Fluor-594 conjugated anti-rabbit secondary antibody (Invitrogen, Life Technologies, Grand Island, N.Y.) at a concentration of 20 mcg/ml for 1 hour at room temperature. For negative controls, sections were treated only with secondary antibody. Slides were counterstained with 4',6-diamidino-2-phenylindole (DAPI) and reviewed with a Zeiss Axioskop 40 fluorescent microscope.

TUNEL Assay for Assessment of Apoptotic Cells in Testicular Sections

The in situ detection of cells with DNA strand breaks by terminal deoxynucleotidyl transferase dUTP nick end labeling (TUNEL) was performed in paraffin-embedded testicular sections by using ApopTag Peroxidase in Situ Apoptosis Detection Kit (Millipore, Billerica, Mass.) as described earlier (Lue, et al., 2000). Negative and positive controls were carried out in every assay. For negative controls, tissue sections were processed in an identical manner, except that the terminal deoxynucleotidyl transferase enzyme was substituted with the same volume of PBS. The apoptotic germ cell population was enumerated out by counting TUNEL positive germ cells using the Axioskop 40 microscope (Zeiss, Thornwood, N.Y.). The rate of germ cell apoptosis (Apoptotic Index, AI) was expressed as the percentage (%) of the number of the cross sections of seminiferous tubules containing TUNEL positive apoptotic germ cells/number of cross sections of all seminiferous tubules at early (I-VI) and late (IX-XIV), and middle (VII-VIII) stages on the slide. In addition, the different types of apoptotic germ cells were assessed using the same testicular sections.

Testosterone Measurement

Testosterone concentrations in plasma, testes, and culture medium were measured by a previously described radioimmunoassay (Lue, et al., 2010) with a minimal detection limit of 0.1 ng/ml. The intra- and inter-assay coefficients of variations were 8 and 11%, respectively.

Statistical Analysis

Statistical analyses were performed using SAS 9.3 (SAS Institute, Carey, N.C.). The in vivo and in vitro data were analyzed by unpaired Student's t-test after confirmation by Shapiro-Wilk test to reject statistically significant non-normality. For the in vivo experiments it was first assessed whether or not CP, EDS or both increased the AI using the unpaired student t-test by comparing CP vs control, EDS vs control and EDS+CP vs control, respectively. Contrasts of a priori interest were then examined which were focused on the effects of HN: CP vs CP+HN; EDS vs EDS+HN; and EDS+CP vs EDS+CP+HN. Statistical comparison of AI in these groups of interest were shown in the figures. For the in vitro analyses, the experiment was designed to determine if HN could salvage testosterone production (treated with KTZ) from Leydig cells in vitro. Accordingly, it was first assessed whether or not KTZ reduced testosterone by unpaired student t-test by comparing KTZ vs control. It was next assessed, by unpaired student t-test, whether HN preventing this occurring by comparing KTZ vs KTZ+HN.

Statistical significance was construed when <0.05. All tests were two-sided.

Results

Rat HN Protein (Rattin) is Expressed in Leydig Cells and Germ Cells in Rat Testis Using immunohistochemistry and a specific antibody against rat HN (also named rattin in rat), it was demonstrated that rat HN was expressed in Leydig cells, spermatocytes and round spermatids. HN appeared predominantly localized in the cytoplasm of Leydig cells, and moderately in cytoplasm of spermatocytes and round spermatids in adult rat testes.

EDS Eliminated Leydig Cells and Suppressed Testosterone Production

Figure 28B:
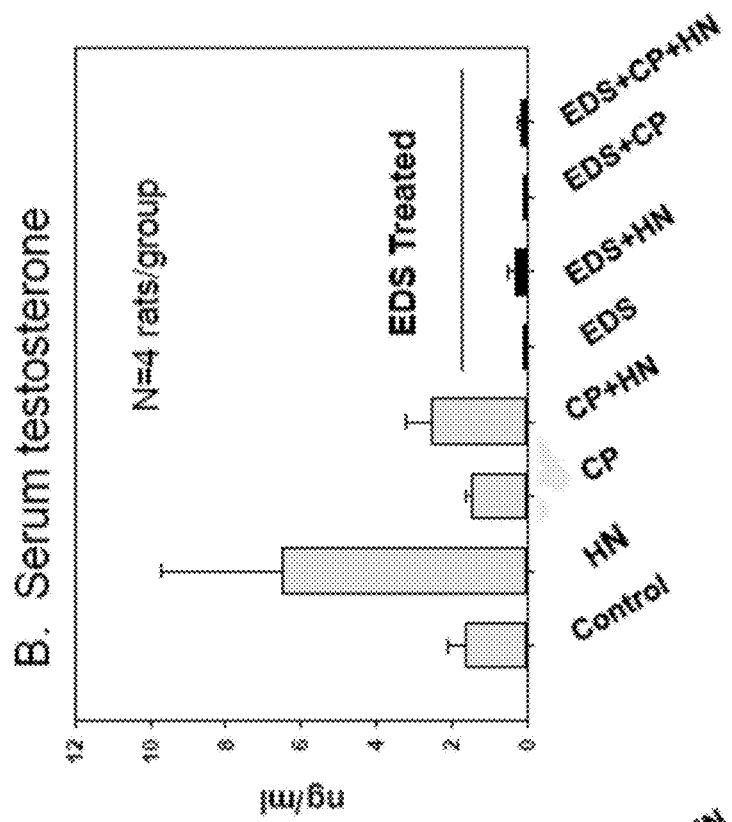
FIGS. 28A-28B show a histogram of intratesticular (FIG. 28A) and serum testicular (FIG. 28B) testosterone (T) levels in animals treated with EDS (Black Bars) or not pre-treated with EDS (Light grey bars). In the EDS treated animals, intratesticular and serum testosterone levels were markedly reduced in all groups (EDS, EDS+HN, EDS+CP, EDS+CP/+HN). HN did not restore intratesticular and serum testosterone levels in the EDS treated rats (Black bars). There were 4 rats in each group.
Figure 28A:
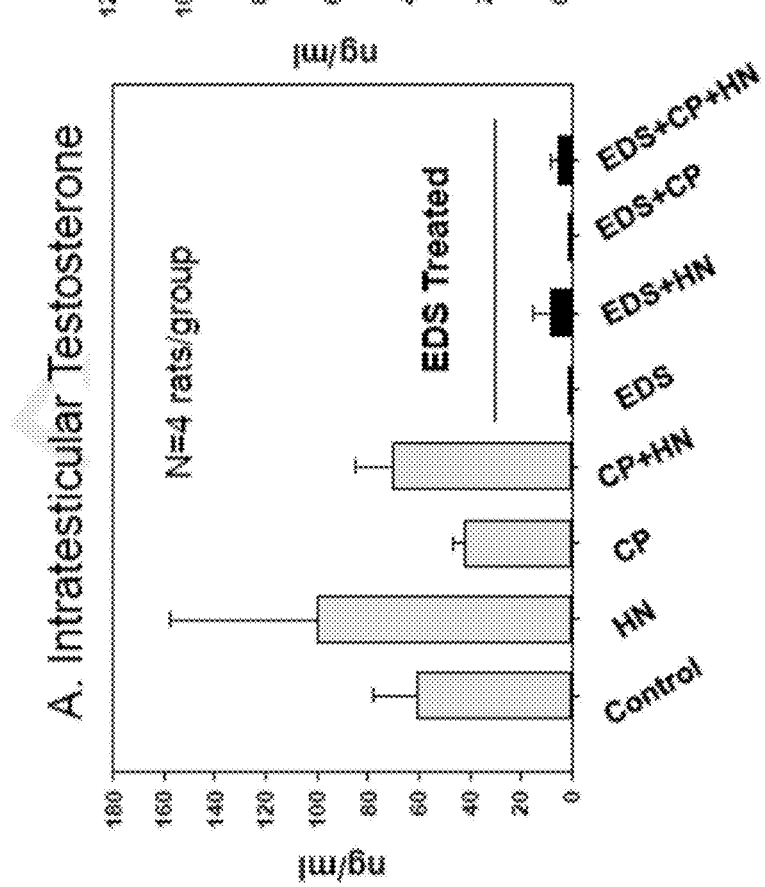

Histology of testes obtained from rats treated with EDS for three days showed the expected depletion of Leydig cells in the interstitial spaces compared to control animals. HN administered 3 days after EDS pre-treatment did not reverse the EDS-induced Leydig cell loss. In all groups treated with EDS, intratesticular (FIG. 28A) and serum testosterone levels (FIG. 28B) were decreased to very low levels (both p<0.0005) compared to those without EDS pre-treatment. CP or HN had no significant effects (p>0.05 in all comparisons) on serum and intratesticular testosterone levels with or without EDS pre-treatment (FIG. 28).

HN Attenuates CP-Induced Germ Cell Apoptosis in Early (I-VI) and Late (IX-XIV) Stages of the Seminiferous Epithelial Cycle CP was used to induce germ cell apoptosis and examined the cytoprotective efficacy of HN on germ cells against apoptosis in adult rats with or without EDS pre-treatment. In both FIG. 29A and FIG. 29B, the light bars represent animals not pre-treated with EDS where Leydig cells were present in the interstitial space, and the dark bars represent EDS pre-treated animals with testes depleted of Leydig cells. FIG. 29A presents germ cell apoptosis index (AI) obtained in early (I-VI) and late (IX-XIV) stages, and FIG. 29B middle (VII-VIII) stages of the seminiferous epithelium cycle.

In these short term experiments, CP significantly increased germ cell apoptosis at early (I-VI) and late (IX-XIV) stages of the seminiferous epithelial cycle compared to control (p=0.0019) (FIG. 29A. light bars). At these early and late stages, CP treatment mainly induced apoptosis of spermatocytes, round spermatid, and differentiated spermatogonia. HN co-treatment significantly reduced CP-induced apoptosis at early and late stages (p=0.021, FIG. 29A, light bars) of seminiferous epithelial cycle in adult rats. Because CP treatment at this dose level for such a short duration did not increase apoptosis in the middle (VII-VIII) stages of the seminiferous epithelial cycle (p=0.328), HN had no effect on CP treated testis (p=0.427) (FIG. 29B, light bars).

HN Attenuates EDS Induced Germ Cell Apoptosis in Middle Stages (VII-VIII) of the Seminiferous Epithelial Cycle Pre-treatment with EDS had significant acute cytotoxic effects on germ cells (p=0.0014) when compared to control in the androgen sensitive middle (VII-VIII) stages (FIG. 29B, dark bars). EDS pre-treatment mainly induced apoptosis of preleptotene and pachytene spermatocytes, round spermatids, and elongated spermatids at the middle stages. The EDS effect may be a direct cytotoxic effect or mediated by the extremely low intratesticular testosterone levels and the depletion of Leydig cells. HN administered 3 days after treatment by EDS significantly reduced the EDS-induced apoptosis of germ cells (p=0.018). Addition of CP treatment in EDS pre-treated rats increased germ cell apoptosis (p=0.0011) as compared to control, but did not additively increased germ cell apoptosis caused by EDS treatment at middle stages (p=0.248). The increase in apoptosis in CP+EDS group was reduced by concomitant HN treatment (p=0.04) at the middle-stages (FIG. 29B dark bars).

EDS pre-treatment did not significantly increase germ cell apoptosis at the early (I-VI) and late (IX-XIV) stages compared to controls (p=0.169) and addition of HN did not significantly reduced germ cell apoptosis (p=0.251) (FIG. 29A, dark bars). Similarly in these early and late stages, CP also did not significantly increased germ cell apoptosis compared to control (p=0.617) and HN did not change the CP effects in EDS pre-treated animals where Leydig cells were absent (p=0.173) (FIG. 29A dark bars). However the comparison of the CP effect on germ cell apoptosis in rats with or without EDS pre-treatment (CP in FIG. 29A, light versus dark bars) showed that when Leydig cells were depleted and intratesticular testosterone was very low, CP induced germ cell apoptosis was significantly lower in EDS pre-treated rats (p=0.0023).

HN has No Effect on KTZ-Induced Suppression of Testosterone (T) of Leydig Cells In Vitro.

Figure 30:
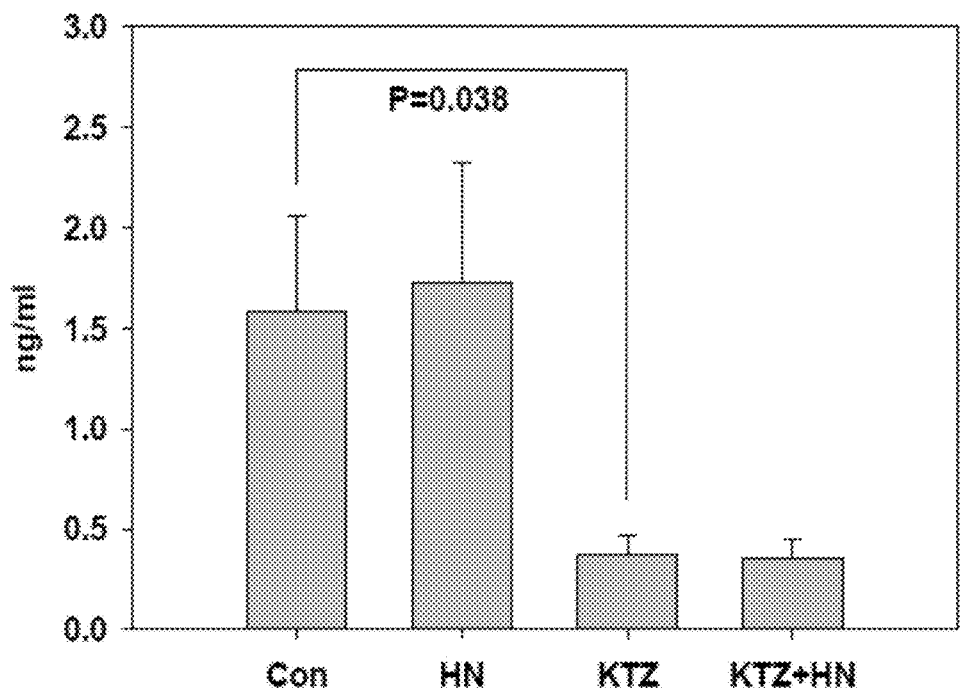
FIG. 30 shows the effect of HN on testosterone levels of Leydig cells exposed to KTZ for 4 hours in vitro. KTZ markedly reduced testosterone levels in cultured Leydig cells. HN did not restore testosterone levels suppressed by KTZ to baseline. Eight replicate experiments were performed where culture Leydig cells were treated with vehicle (control), HN, KTZ, and HN+KTZ respectively The drawings illustrate embodiments of the technology and are not limiting. For clarity and ease of illustration, the drawings are not made to scale and, in some instances, various aspects may be shown exaggerated or enlarged to facilitate an understanding of particular embodiments.

KTZ, compared to control, lowered the testosterone levels significantly (p=0.038, FIG. 30) within in 4 hours. HN treatment, compared with control, did not salvage the KTZ induced decrease in testosterone production by the Leydig cells in vitro.

Discussion

Testicular stressors that induce germ cell apoptosis include agents that lower intratesticular testosterone, testicular hyperthermia, and agents that can cause direct germ cell damage (e.g. alkylating agents such as CP).

In this study using a rat humanin (rattin) specific antibody, it was observed that rat HN was expressed in stress-sensitive primary spermatocytes and round spermatids.

The chemotherapeutic agent CP was used to induce germ cell apoptosis. In these studies, it was demonstrated that HN was able to differentially protect against CP-induced stage-specific (early and late) germ cell apoptosis in rats.

When Leydig cells were eliminated by EDS, CP failed to increase germ cell apoptosis in early and late stages which were not sensitive to androgens. This data suggests that Leydig cells may be involved in CP-induced germ cell apoptosis and absence of Leydig cells was protective for germ cells. In prior studies, GnRH antagonist plus the anti-androgen flutamide treatment suppressed testosterone levels and action in rats and protected spermatogonial stem cell damage induced by CP or irradiation and restored spermatogenesis and fertility (Meistrich, et al., 1995; Shetty & Meistrich, 2005). However, when the same principle was translated to non-human primates, suppression of testosterone by GnRH antagonist did not restore spermatogenesis induced by irradiation indicating species differences in testicular responses to GnRH antagonist and irradiation (Boekelheide, et al., 2005; Shetty & Meistrich, 2005). The observation that CP-induced apoptosis of germ cells requires Leydig cells and testosterone does not distract from the point that HN protects against germ cell apoptosis in the absence of Leydig cells and despite the fact that intratesticular testosterone levels are very low.

To show that the cytoprotective effect of HN against chemotherapy-induced apoptosis of male germ cells was a direct effect on germ cells required evidence that the cytoprotective effects of HN did not require Leydig cell and its products. EDS is a cytotoxic agent that effectively eliminates Leydig cell by activating caspase-3 inducing Leydig cell apoptosis (Morris, et al., 1997; Rommerts, et al., 2004;

Rommerts, et al., 1988; Sprando, et al., 1990). By selectively eliminating Leydig cells with EDS in the present study, it was demonstrated that EDS induced germ cell apoptosis in short term treatment mainly at the androgen sensitive middle stages of the seminiferous epithelium but not at non-androgen sensitive early and late stages. This suggests that EDS induces apoptosis by reducing intratesticular testosterone to very low levels. Administration of exogenous HN protected germ cells at the middle stages from apoptosis in response to EDS despite the absence of Leydig cells and testosterone. Although effects of HN on serum and intratesticular testosterone level in vivo were not observed (FIG. 28), the possibility that this was due to a large variation of serum and intratesticular T levels or a small number of animals examined could not be ruled out. It was also observed that CP failed to enhance EDS induced germ cell apoptosis in the middle stages. This might be due to the following: 1) absence of testosterone protects germ cell from CP action (Meistrich, et al., 1995; Shetty & Meistrich, 2005); 2) CP does not affect germ cell apoptosis in the middle stages after 12 hours treatment; and 3) the very potent cytotoxic effect of pre-treatment of EDS may have obliterated the small effect if any of CP in the middle stages. When there was no increase in CP-induced apoptosis in middle stages or EDS-induced apoptosis in early or late stages, HN has no effect on promoting germ cell survival.

Data herein demonstrates that HN protects against CP-induced germ cell apoptosis at early and late stages. HN reduced EDS-induced germ cell apoptosis at middle stages despite depletion of Leydig cells by EDS. Thus, the data herein provides strong supportive evidence that HN has direct cytoprotective action on male germ cells after chemotherapy in a stage-specific fashion. It should be emphasized that the stage specificity of the cytoprotective effects of humanin are evident in short term experiments. It was anticipated that chronic treatment with cytotoxic agent will spread from the early and late stages where they begin, to all stages of the seminiferous epithelium. Once apoptosis occurs in one stage(s), with time and with continued treatment, the spermatogenic cycle will be arrested. If spermatogonia are damaged by the cytotoxic agent, the spermatogenic cycle may not recover leading to onco-infertility.

Endogenous HN is expressed in both immature and adult Leydig cells (Colon, et al., 2006); the latter is confirmed in the current study. To investigate the direct effects of HN on testosterone production from Leydig cells, in vitro experiments were performed to investigate synthetic HN's action on cultured adult Leydig cells treated with ketoconazole (KTZ). KTZ is known to reduce testosterone levels by acting at multiple steps in testosterone synthesis. When HN was added to Leydig cells in vitro, synthetic HN at a dose examined was not able to prevent the decreased testosterone production of Leydig cells induced by treatment with KTZ.

In summary, it was demonstrated that with short term treatment: 1) HN significantly reduced CP and EDS induced germ cell apoptosis at different stages of the seminiferous epithelium; 2) HN protected EDS-induced germ cell apoptosis in middle stages of the seminiferous cycle despite depletion of Leydig cells and lower intratesticular testosterone levels in adult rats.

REFERENCE LIST

Arakawa T, Kita Y, Niikura T. (2008) A rescue factor for Alzheimer's diseases: discovery, activity, structure, and mechanism. Curr Med Chem 15(21): 2086-2098.

Arakawa T1, Niikura T, Kita Y. (2011) The biological activity of Humanin analogs correlates with structure stabilities in solution. Int J Biol Macromol 49(1): 93-97. doi: 10.1016/j.ijbiomac.2011.04.003.

Bachar A R, Scheffer L, Schroeder A S, Nakamura H K, Cobb L J, Oh Y K, Lerman L O, Pagano R E, Cohen P & Lerman A. (2010) *Humanin is expressed in human vascular walls and has a cytoprotective effect against oxidized LDL-induced oxidative stress*. Cardiovasc. Res. 88, 360-366.

Bar-Joseph H, Ben-Aharon I, Rizel S, Stemmer S M, Tzabari M, Shalgi R. Doxorubicin-induced apoptosis in germinal vesicle (GV) oocytes. Reprod Toxicol. 2010; 30(4):566-72.

Ben-Aharon I, Bar-Joseph H, Tzarfaty G, Kuchinsky L, Rizel S, Stemmer S M, Shalgi R. Doxorubicin-induced ovarian toxicity. Reprod Biol Endocrinol. 2010; 8:20. PMCID: Pmc2838903.

Biglia N, Peano E, Sgandurra P, Moggio G, Pecchio S, Maggiorotto F, Sismondi P. Body mass index (BMI) and breast cancer: impact on tumor histopathologic features, cancer subtypes and recurrence rate in pre and postmenopausal women. Gynecol Endocrinol. 2013; 29(3):263-7.

Boekelheide K, Schoenfeld H A, Hall S J, Weng C C, Shetty G, Leith J, Harper J, Sigman M, Hess D L & Meistrich M L. (2005) Gonadotropin-releasing hormone antagonist (Cetrorelix) therapy fails to protect nonhuman primates (*Macaca arctoides*) from radiation-induced spermatogenic failure. J. Androl. 26, 222-234.

Bristol-Gould S K, Kreeger P K, Selkirk C G, Kilen S M, Mayo K E, Shea L D, Woodruff T K. Fate of the initial follicle pool: empirical and mathematical evidence supporting its sufficiency for adult fertility. Dev Biol. 2006; 298(1):149-54.

Cai L, Hales B F, Robaire B. (1997) Induction of apoptosis in the germ cells of adult male rats after exposure to cyclophosphamide. Biol Reprod 56(6): 1490-1497.

Chlebowski R T, Blackburn G L, Buzzard I M, Rose D P, Martino S, Khandekar J D, York R M, Jeffery R W, Elashoff R M, Wynder E L. Adherence to a dietary fat intake reduction program in postmenopausal women receiving therapy for early breast cancer. The Women's Intervention Nutrition Study. J Clin Oncol. 1993; 11(11): 2072-80.

Choy J T & Brannigan R E. (2013) *The determination of reproductive safety in men during and after cancer treatment*. Fertil. Steril. 100, 1187-1191.

Collisson E A, De A, Suzuki H, Gambhir S S & Kolodney M S. (2003) *Treatment of metastatic melanoma with an orally available inhibitor of the Ras-Raf-MAPK cascade*. Cancer Res. 63, 5669-5673.

Colon E, Strand M L, Carlsson-Skwirut C, Wahlgren A, Svechnikov K V, Cohen P & Soder O. (2006) *Anti-apoptotic factor humanin is expressed in the testis and prevents cell-death in leydig cells during the first wave of spermatogenesis*. J. Cell. Physiol. 208, 373-385.

Craft N, Bruhn K W, Nguyen B D, Prins R, Liau L M, Collisson E A, De A, Kolodney M S, Gambhir S S & Miller J F. (2005) *Bioluminescent imaging of melanoma in live mice*. J. Invest. Dermatol. 125, 159-165.

Delbes G, Vaisheva F, Luu T, Marcon L, Hales B F & Robaire B. (2010) *Reversibility of the effects of the* chemotherapeutic regimen for non-Hodgkin lymphoma, cyclophosphamide, doxorubicin, vincristine, and prednisone, on the male rat reproductive system and progeny outcome. Reprod. Toxicol. 29, 332-338.

Desai V G, Herman E H, Moland C L, Branham W S, Lewis S M, Davis K J, George N I, Lee T, Kerr S, Fuscoe J C. Development of doxorubicin-induced chronic cardiotoxicity in the B6C3F1 mouse model. Toxicol Appl Pharmacol. 2013; 266(1):109-21.

Dohle G R. (2010) *Male infertility in cancer patients: Review of the literature*. Int. J. Urol. 17, 327-331.

Doroshow J H. Anthracycline antibiotic-stimulated superoxide, hydrogen peroxide, and hydroxyl radical production by NADH dehydrogenase. Cancer Res. 1983; 43(10): 4543-51.

Drumond A L, Weng C C, Wang G, Chiarini-Garcia H, Eras-Garcia L & Meistrich M L. (2011) *Effects of multiple doses of cyclophosphamide on mouse testes: accessing the germ cells lost, and the functional damage of stem cells.* Reprod. Toxicol. 32, 395-406.

Erkkila K, Henriksen K, Hirvonen V, Rannikko S, Salo J, Parvinen M & Dunkel L. (1997) *Testosterone regulates apoptosis in adult human seminiferous tubules in vitro*. J. Clin. Endocrinol. Metab. 82, 2314-2321.

Garrisi V M, Tufaro A, Trerotoli P, Bongarzone I, Quaranta M, Ventrella V, Tommasi S, Giannelli G, Paradiso A. Body mass index and serum proteomic profile in breast cancer and healthy women: a prospective study. PLoS One. 2012; 7(11):e49631. PMCID: Pmc3511468.

Goel S, Gupta N, Walcott B P, Snuderl M, Kesler C T, Kirkpatrick N D, Heishi T, Huang Y, Martin J D, Ager E, Samuel R, Wang S, Yazbek J, Vakoc B J, Peterson R T, Padera T P, Duda D G, Fukumura D, Jain R K. Effects of vascular-endothelial protein tyrosine phosphatase inhibition on breast cancer vasculature and metastatic progression. J Natl Cancer Inst. 2013; 105(16):1188-201. PMCID: Pmc3748004.

Gor P P, Su H I, Gray R J, Gimotty P A, Horn M, Aplenc R, Vaughan W P, Tallman M S, Rebbeck T R, DeMichele A. (2010) Cyclophosphamide-metabolizing enzyme polymorphisms and survival outcomes after adjuvant chemotherapy for node-positive breast cancer: a retrospective cohort study. Breast cancer research 12: R26.

Guo B, Zhai D, Cabezas E, Welsh K, Nouraini S, Satterthwait A C, Reed J C. (2003) Humanin peptide suppresses apoptosis by interfering with Bax activation. Nature 423: 456-461.

Hartmann T B, Mattern E, Wiedemann N, van Doorn R, Willemze R, Niikura T, Hildenbrand R, Schadendorf D & Eichmuller S B. (2008) *Identification of selectively expressed genes and antigens in CTCL*. Exp. Dermatol. 17, 324-334.

Hashimoto Y, Kurita M, Aiso S, Nishimoto I, Matsuoka M. (2009) Humanin inhibits neuronal cell death by interacting with a cytokine receptor complex or complexes involving CNTF receptor α/WSX-1/gp130. Mol Biol Cell 20: 2864-2873.

Hashimoto Y, Niikura T, Ito Y, Sudo H, Hata M, Arakawa E, Abe Y, Kita Y & Nishimoto I. (2001) *Detailed characterization of neuroprotection by a rescue factor humanin against various Alzheimer's disease-relevant insults.* J. Neurosci. 21, 9235-9245.

Hashimoto Y, Niikura T, Tajima H, Yasukawa T, Sudo H, Ito Y, Kita Y, Kawasumi M, Kouyama K, Doyu M, Sobue G, Koide T, Tsuji S, Lang J, Kurokawa K & Nishimoto I. (2001) *A rescue factor abolishing neuronal cell death by a wide spectrum of familial Alzheimer's disease genes and Abeta*. Proc. Natl. Acad. Sci. U.S.A. 98, 6336-6341.

Hashimoto Y, Suzuki H, Aiso S, Niikura T, Nishimoto I, Matsuoka M. (2005) Involvement of tyrosine kinases and STAT3 in Humanin-mediated neuroprotection. Life Sci 77: 3092-3104.

Hashimoto Y, Terashita K, Niikura T, Yamagishi Y, Ishizaka M, Kanekura K, Chiba T, Yamada M, Kita Y, Aiso S, Matsuoka M & Nishimoto I. (2004) Humanin antagonists: mutants that interfere with dimerization inhibit neuroprotection by Humanin. Eur J Neurosci 19, 2356-2364.

Hoang P T, Park P, Cobb L J, Paharkova-Vatchkova V, Hakimi M, Cohen P & Lee K W. (2010) *The neurosurvival factor Humanin inhibits beta-cell apoptosis via signal transducer and activator of transcription 3 activation and delays and ameliorates diabetes in nonobese diabetic mice*. Metabolism. 59, 343-349.

Ikonen M, Liu B, Hashimoto Y, Ma L, Lee K W, Niikura T, Nishimoto I, and Cohen P. (2003) Interaction between the Alzheimer's survival peptide Humanin and insulin-like growth factor-binding protein 3 regulates cell survival and apoptosis. Proc Natl Acad Sci USA 100: 13042-13047.

Jia Y, Castellanos J, Wang C, Sinha-Hikim I, Lue Y, Swerdloff R S, Sinha-Hikim A P. (2009) Mitogen-Activated Protein Kinase Signaling in Male Germ Cell Apoptosis in the Rat: Biol.Reprod 80: 771-780.

Jia Y, Lee K W, Swerdloff R, Hwang D, Cobb L J, Sinha Hikim A, Lue Y H, Cohen P, and Wang C. (2010) Interaction of insulin-like growth factor-binding protein-3 and BAX in mitochondria promotes male germ cell apoptosis. J Biol Chem 285: 1726-1732.

Jia Y, Lue Y H, Swerdloff R, Lee K W, Cobb L J, Cohen P & Wang C. (2013) The cytoprotective peptide humanin is induced and neutralizes Bax after pro-apoptotic stress in the rat testis. Andrology 1, 651-659.

Jia Y, Sinha Hikim A P, Swerdloff R S, Lue Y H, Vera Y, Zhang X S, Hu Z Y, Li Y C, Liu Y X, Wang C. (2007) Signaling pathways for germ cell death in adult Cynomolgus monkeys (*Macaca fascicularis*) induced by mild testicular hyperthermia and exogenous testosterone treatment. Biol Reprod 77: 83-92.

Jimenez M, Spaliviero J A, Grootenhuis A J, Verhagen J, Allan C M, Handelsman D J. Validation of an ultrasensitive and specific immunofluorometric assay for mouse follicle-stimulating hormone. Biol Reprod. 2005; 72(1): 78-85.

Kamineni A, Anderson M L, White E, Taplin S H, Porter P, Ballard-Barbash R, Malone K, Buist D S. Body mass index, tumor characteristics, and prognosis following diagnosis of early-stage breast cancer in a mammographically screened population. Cancer Causes Control. 2013; 24(2):305-12. PMCID: Pmc3557530.

Kim S Y, Cordeiro M H, Serna V A, Ebbert K, Butler L M, Sinha S, Mills A A, Woodruff T K, Kurita T. Rescue of platinum-damaged oocytes from programmed cell death through inactivation of the p53 family signaling network. Cell Death Differ. 2013; 20(8):987-97. PMCID: Pmc3705595.

Kuliawat R1, Klein L, Gong Z, Nicoletta-Gentile M, Nemkal A, Cui L, Bastie C, Su K, Huffman D, Surana M, Barzilai N, Fleischer N, Muzumdar R. (2013) Potent humanin analog increases glucose-stimulated insulin secretion through enhanced metabolism in the β cell. FASEB J 27(12): 4890-4898. doi: 10.1096/fj.13-231092. Epub 2013 Aug. 30.

Kunesová G, Hlavaácek J, Patocka J, Evangelou A, Zikos C, Benaki D, Paravatou-Petsotas M, Pelecanou M, Livaniou E, Slaninova J. (2008) The multiple T-maze in vivo testing of the neuroprotective effect of humanin analogs. Peptides 29: 1982-1987.

Loren A W, Mangu P B, Beck L N, Brennan L, Magdalinski A J, Partridge A H, Quinn G, Wallace W H & Oktay K. (2013) *Fertility preservation for patients with cancer: American Society of Clinical Oncology clinical practice guideline update.* J. Clin. Oncol. 31, 2500-2510.

Lue Y H, Sinha Hikim A P, Swerdloff R S, Im P, Taing K S, Bui T, Leung A, Wang C. (1999) Single exposure to heat induces stage-specific germ cell apoptosis in rats: role of intratesticular testosterone (T) on stage specificity. Endocrinology 140: 1709-1717.

Lue Y H, Wang C, Liu P Y, Erkilla K & Swerdloff R S. (2010) *Insights into the pathogenesis of XXY phenotype from comparison of the clinical syndrome with an experimental XXY mouse model.* Pediatr Endocrinol Rev 8 Suppl 1, 140-144.

Lue Y, Swerdloff R, Liu Q, Mehta H, Hikim A S, Lee K W, Jia Y, Hwang D, Cobb L J, Cohen P & Wang C. (2010) *Opposing roles of insulin-like growth factor binding protein 3 and humanin in the regulation of testicular germ cell apoptosis.* Endocrinology 151, 350-357.

Lue Y, Wang C, Cui Y, Wang X, Sha J, Zhou Z, Xu J, Hikim A P & Swerdloff R S. (2009) *Levonorgestrel enhances spermatogenesis suppression by testosterone with greater alteration in testicular gene expression in men.* Biol. Reprod. 80, 484-492.

Lue Y, Wang C, Liu Y X, Hikim A P, Zhang X S, Ng C M, Hu Z Y, Li Y C, Leung A, and Swerdloff R S. (2006) Transient testicular warming enhances the suppressive effect of testosterone on spermatogenesis in adult cynomolgus monkeys (*Macaca fascicularis*). J Clin Endocrinol Metab 91: 539-545.

Marcon L, Hales B F, Robaire B. (2008) Reversibility of the effects of subchronic exposure to the cancer chemotherapeutics bleomycin, etoposide, and cisplatin on spermatogenesis, fertility, and progeny outcome in the male rat. J Andrology 29: 4.

Marcon L, Zhang X, Hales B F, Robaire B & Nagano M C. (2011) *Effects of Chemotherapeutic Agents for Testicular Cancer on Rat Spermatogonial Stem/Progenitor Cells.* J. Androl.

Matsuoka M, Hashimoto Y. (2010) Humanin and the receptors for humanin. Mol Neurobiol 41: 22-28.

Maximov V, Martynenko A, Hunsmann G & Tarantul V. (2002) *Mitochondrial 16S rRNA gene encodes a functional peptide, a potential drug for Alzheimer's disease and target for cancer therapy.* Med. Hypotheses 59, 670-673.

Mayle A, Luo M, Jeong M, Goodell M A. Flow cytometry analysis of murine hematopoietic stem cells. Cytometry Part A: the journal of the International Society for Analytical Cytology. 2013; 83(1):27-37. PMCID: Pmc3638885.

Meistrich M L, Finch M, da Cunha M F, Hacker U & Au W W. (1982) *Damaging effects of fourteen chemotherapeutic drugs on mouse testis cells.* Cancer Res. 42, 122-131.

Meistrich M L. (2013) *Effects of chemotherapy and radiotherapy on spermatogenesis in humans.* Fertil. Steril. 100, 1180-1186.

Meistrich M L. (2009) Male gonadal toxicity. Pediatr Blood Cancer 53:261-266.

Miao J, Zhang W, Yin R, Liu R, Su C, Lei G, Li Z. (2008) S14G HN ameliorates Abeta25-35-induced behavioral deficits by reducing neuroinflammatory responses and apoptosis in mice. Neuropeptides 42: 557-567.

Moretti E, Giannerini V, Rossini L, Matsuoka M, Trabalzini L & Collodel G. (2010) *Immunolocalization of humanin in human sperm and testis.* Fertil. Steril. 94, 2888-2890.

Mottaghi-Dastjerdi N, Soltany-Rezaee-Rad M, Sepehrizadeh Z, Roshandel G, Ebrahimifard F & Setayesh N. (2014) *Genome expression analysis by suppression subtractive hybridization identified overexpression of Humanin, a target gene in gastric cancer chemoresistance.* Daru: journal of Faculty of Pharmacy, Tehran University of Medical Sciences 22, 14.

Muzumdar R H, Huffman D M, Calvert J W, Jha S, Weinberg Y, Cui L, Nemkal A, Atzmon G, Klein L, Gundewar S, Ji S Y, Lavu M, Predmore B L & Lefer D J. (2010) *Acute humanin therapy attenuates myocardial ischemia and reperfusion injury in mice.* Arterioscler. Thromb. Vac. Biol. 30, 1940-1948.

Nangia A K, Krieg S A & Kim S S. (2013) *Clinical guidelines for sperm cryopreservation in cancer patients.* Fertil. Steril. 100, 1203-1209.

memory deficit in triple transgenic mice. PLoS One. 2011; 6(1):e16259. PMCID: 3022031.

O'Brien P J, Dameron G W, Beck M L, Kang Y J, Erickson B K, Di Battista T H, Miller K E, Jackson K N, Mittelstadt S. Cardiac troponin T is a sensitive, specific biomarker of cardiac injury in laboratory animals. Lab Anim Sci. 1997; 47(5):486-95.

Ottewell P D, Monkkonen H, Jones M, Lefley D V, Coleman R E, Holen I. Antitumor effects of doxorubicin followed by zoledronic acid in a mouse model of breast cancer. J Natl Cancer Inst. 2008; 100(16):1167-78.

Panosyan E H, Wang Y, Xia P, Lee W N, Pak Y, Laks D R, Lin H J, Moore T B, Cloughesy T F, Kornblum H I, Lasky J L, 3rd. Asparagine depletion potentiates the cytotoxic effect of chemotherapy against brain tumors. Molecular cancer research: MCR. 2014; 12(5):694-702. PMCID: Pmc4020976.

Perez G I, Knudson C M, Leykin L, Korsmeyer S J, Tilly J L. Apoptosis-associated signaling pathways are required for chemotherapy-mediated female germ cell destruction. Nat Med. 1997; 3(11):1228-32.

Prentice R L, Caan B, Chlebowski R T, Patterson R, Kuller L H, Ockene J K, Margolis K L, Limacher M C, Manson J E, Parker L M, Paskett E, Phillips L, Robbins J, Rossouw J E, Sarto G E, Shikany J M, Stefanick M L, Thomson C A, Van Horn L, Vitolins M Z, Wactawski-Wende J, Wallace R B, Wassertheil-Smoller S, Whitlock E, Yano K, Adams-Campbell L, Anderson G L, Assaf A R, Beresford S A, Black H R, Brunner R L, Brzyski R G, Ford L, Gass M, Hays J, Heber D, Heiss G, Hendrix S L, Hsia J, Hubbell F A, Jackson R D, Johnson K C, Kotchen J M, LaCroix A Z, Lane D S, Langer R D, Lasser N L, Henderson M M. Low-fat dietary pattern and risk of invasive breast cancer: the Women's Health Initiative Randomized Controlled Dietary Modification Trial. JAMA. 2006; 295(6):629-42.

Roti Roti E C, Leisman S K, Abbott D H, Salih S M. Acute doxorubicin insult in the mouse ovary is cell- and follicle-type dependent. PLoS One. 2012; 7(8):e42293. PMCID: Pmc3410926.

Rundberg Nilsson A, Bryder D, Pronk C J. Frequency determination of rare populations by flow cytometry: a hematopoietic stem cell perspective. Cytometry Part A: the journal of the International Society for Analytical Cytology. 2013; 83(8):721-7.

Russell L. (1977) Movement of spermatocytes from the basal to the adluminal compartment of the rat testes. Am J Anat 148: 313-328.

Schlueter A J, Bhatia S K, Li X, Tygrett L T, Yamashita Y, de Vries P, Waldschmidt T J. Delineation among eight major hematopoietic subsets in murine bone marrow using a two-color flow cytometric technique. Cytometry. 2001; 43(4):297-307.

Serradj N, Jamon M. Age-related changes in the motricity of the inbred mice strains 129/sv and C57BL/6j. Behav Brain Res. 2007; 177(1):80-9.

Simpson E R, Brown K A. Obesity and breast cancer: role of inflammation and aromatase. J Mol Endocrinol. 2013; 51(3):T51-9.

Sinha Hikim A P, Rajavashisth T B, Sinha Hikim I, Lue Y, Bonavera J J, Leung A, Wang C, Swerdloff R S. (1997) Significance of apoptosis in the temporal and stage-specific loss of germ cells in the adult rat after gonadotropin deprivation. Biol Reprod 57: 1193-1201;

Sloderbach A, Gorska A, Sikorska M, Misiura K & Hladon B. (2013) *Classical oxazaphosphorines—metabolism and therapeutic properties—new implications*. Postepy higieny i medycyny doswiadczalnej (Online) 67, 1235-1253.

Sponne I, Fifre A, Koziel V, Kriem B, Oster T, Pillot T. (2004) Humanin rescues cortical neurons from prion-peptide-induced apoptosis. Mol Cell Neurosci 25(1): 95-102.

Sprando R L, Santulli R, Awoniyi C A, Ewing L L & Zirkin B R. (1990) Does ethane 1,2-dimethanesulphonate (EDS) have a direct cytotoxic effect on the seminiferous epithelium of the rat testis? J. Androl. 11, 344-352.

Sun X, Zhou Z, Kang Y J. Attenuation of doxorubicin chronic toxicity in metallothionein-overexpressing transgenic mouse heart. Cancer Res. 2001; 61(8):3382-7.

Tarantul V Z & Hunsmann G. (2001) *Mitochondrial polypeptides of the oxidative phosphorylation pathway as potential new targets for anti-cancer therapy*. Med. Hypotheses 56, 386-387.

Toppari J & Parvinen M. (1985) *In vitro differentiation of rat seminiferous tubular segments from defined stages of the epithelial cycle morphologic and immunolocalization analysis*. J. Androl. 6, 334-343.

Trost L W & Brannigan R E. (2012) *Oncofertility and the male cancer patient*. Current treatment options in oncology 13, 146-160.

Watring W G, Byfield J E, Lagasse L D, Lee Y D, Juillard G, Jacobs M, Smith M L. (1974) Combination Adriamycin and radiation therapy in gynecologic cancers. Gynecol Oncol 2(4):518-526.

Yamada M, Chiba T, Sasabe J, Terashita K, Aiso S, Matsuoka M. (2008) Nasal colivelin treatment ameliorates memory impairment related to Alzheimer's disease. Neuropsychopharmaco 33: 2020-2032.

Yamagishi Y, Hashimoto Y, Niikura T, Nishimoto I. (2003) Identification of essential amino acids in Humanin, a neuroprotective factor against Alzheimer's disease-relevant insults. Peptides 24(4): 585-595.

Yen K, Lee C, Mehta H, Cohen P. (2013) The emerging role of the mitochondrial-derived peptide humanin in stress resistance. J Mol Endocrinol 50(1): R11-19. doi: 10.1530/JME-12-0203. Print 2013 February.

Zhai D, Luciano F, Zhu X, Guo B, Satterthwait A C, Reed J C. (2005) Humanin binds and nullifies Bid activity by blocking its activation of Bax and Bak. J Biol Chem 280: 15815-15824.

The entirety of each patent, patent application, publication and document referenced herein hereby is incorporated by reference. In case of conflict, the specification, including definitions will control. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed.

Unless otherwise defined, all technical and scientific terms used herein have the same meaning as commonly understood by one of ordinary skill in the art to which this invention belongs.

As used herein, the singular forms "a", "and," and "the" include plural referents unless the context clearly indicates otherwise. Thus, the term "a" or "an" can refer to one of or a plurality of the elements it modifies (e.g., "a reagent" can mean one or more reagents) unless it is contextually clear either one of the elements or more than one of the elements is described.

The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%).

It is understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method of treating an adult subject having a metastatic neoplasia, tumor, cancer or malignancy, comprising administering to the adult subject an amount of humanin or a humanin analog and a chemotherapeutic agent sufficient to reduce or inhibit proliferation of the metastatic neoplasia, tumor, cancer or malignancy, wherein (i) the amount of the humanin or the humanin analog is in the range of 0.5 to 15 mg/kg body weight, (ii) the chemotherapeutic agent is a DNA intercalating agent or an alkylating agent, and (iii) the humanin or humanin analog increases efficacy or activity of the chemotherapeutic agent.

2. The method of claim 1, wherein the humanin comprises the sequence: MAPRGFSCLLLLTSEIDLPVKRRA (SEQ ID NO:1).

3. The method of claim 1, wherein the humanin analog comprises the sequence: MAPRGFSCLLLLT-GEIDLPVKRRA (HN-S14G) (SEQ ID NO:2), or any sequence set forth in Tables 1-4.

4. The method of claim 1, wherein the chemotherapeutic agent comprises an alkylating agent.

5. The method of claim 1, wherein the chemotherapeutic agent comprises a DNA intercalating agent or an agent that attaches to DNA.

6. The method of claim 1, wherein the chemotherapeutic agent comprises cyclophosphamide, doxorubicin, azathioprine, cyclosporin A, prednisolone, melphalan, chlorambucil, mechlorethamine, busulphan, methotrexate, 6-mercaptopurine, thioguanine, 5-fluorouracil, cytosine arabinoside, 5-azacytidine (5-AZC) and 5-azacytidine related compounds, bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, a taxane, vinblastine, vincristine, dibromomannitol, gemcitabine, Temozolomide, or pemetrexed.

7. The method of claim 1, wherein the neoplasia, tumor, cancer or malignancy comprises a solid cellular mass.

8. The method of claim 1, wherein the neoplasia, tumor, cancer or malignancy comprises hematopoietic cells.

9. The method of claim 1, wherein the neoplasia, tumor, cancer or malignancy comprises a carcinoma, sarcoma, lymphoma, leukemia, adenoma, adenocarcinoma, melanoma, glioma, glioblastoma, medulloblastoma, meningioma, neuroblastoma, retinoblastoma, astrocytoma, oligodendrocytoma, mesothelioma, reticuloendothelial, lymphatic or haematopoietic neoplasia, tumor, cancer or malignancy.

10. The method of claim 9, wherein the haematopoietic neoplasia, tumor, cancer or malignancy comprises a myeloma, lymphoma or leukemia.

11. The method of claim 1, wherein the neoplasia, tumor, cancer or malignancy comprises a metastatic myeloma.

12. The method of claim 1, wherein the neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, skin, biliary tract, or hematologic neoplasia, tumor, or cancer.

13. The method of claim 1, wherein the method inhibits or reduces relapse or progression of the neoplasia, tumor, cancer or malignancy.

14. The method of claim 1, wherein the treatment results in partial or complete destruction of the neoplasia, tumor, cancer or malignancy; stimulating, inducing or increasing necrosis, lysis or apoptosis of the neoplasia, tumor, cancer or malignancy; reducing volume size or cell mass of the neoplasia, tumor, cancer or malignancy; inhibiting or preventing progression or an increase in the neoplasia, tumor, cancer or malignancy volume, mass, size or cell numbers; or prolonging lifespan.

15. The method of claim 1, wherein the subject is a mammal.

16. The method of claim 1, wherein the subject is a human.

17. The method of claim 1, wherein the adult is a fertile adult.

18. The method of claim 17, wherein the amount of humanin or a humanin analog administered is an amount sufficient to inhibit a decrease or reduction of fertility due to the administration of the chemotherapeutic agent.

* * * * *

```
                               SEQUENCE LISTING

<160> NUMBER OF SEQ ID NOS: 62

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 1

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 2

Met Ala Pro Arg Gly Phe Ser Cys Leu Leu Leu Leu Thr Gly Glu Ile
1               5                   10                  15

Asp Leu Pro Val Lys Arg Arg Ala
            20

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is D-Serine

<400> SEQUENCE: 3

Met Ala Pro Arg Gly Phe Ser Cys Leu Leu Leu Leu Thr Xaa Glu Ile
1               5                   10                  15

Asp Leu Pro Val Lys Arg Arg Ala
            20

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 4

Met Ala Pro Ala Gly Ala Ser Cys Leu Leu Leu Leu Thr Gly Glu Ile
1               5                   10                  15

Asp Leu Pro Val Lys Arg Arg Ala
            20

<210> SEQ ID NO 5
```

```
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is D-Serine

<400> SEQUENCE: 5

Met Ala Pro Ala Gly Ala Ser Cys Leu Leu Leu Leu Thr Xaa Glu Ile
1               5                   10                  15

Asp Leu Pro Val Lys Arg Arg Ala
            20

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (12)..(12)
<223> OTHER INFORMATION: Xaa is D-Serine

<400> SEQUENCE: 6

Pro Ala Gly Ala Ser Cys Leu Leu Leu Leu Thr Xaa Glu Ile Asp Leu
1               5                   10                  15

Pro

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 7

Pro Ala Gly Ala Ser Arg Leu Leu Leu Leu Thr Gly Glu Ile Asp Leu
1               5                   10                  15

Pro

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 8

Glu Phe Leu Ile Val Ile Lys Ser Met Ala Pro Arg Gly Phe Ser Cys
1               5                   10                  15

Leu Leu Leu Leu Thr Ser Glu Ile Asp Leu Pro Val Lys Arg Arg Ala
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Humanin
```

Polypeptide

<400> SEQUENCE: 9

Glu Phe Leu Ile Val Ile Lys Ser Met Ala Pro Arg Gly Phe Ser Cys
1               5                   10                  15
Leu Leu Leu Leu Thr Gly Glu Ile Asp Leu Pro Val Lys Arg Arg Ala
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 10

Glu Phe Leu Ile Val Ile Lys Ser Met Ala Pro Ala Gly Ala Ser Cys
1               5                   10                  15
Leu Leu Leu Leu Thr Gly Glu Ile Asp Leu Pro Val Lys Arg Arg Ala
            20                  25                  30

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 11

Ser Ala Leu Leu Arg Ser Ile Pro Ala Pro Ala Gly Ala Ser Arg Leu
1               5                   10                  15
Leu Leu Leu Thr Gly Glu Ile Asp Leu Pro
            20                  25

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 12

Met Ala Pro Arg Gly Phe Ser Cys Arg Leu Leu Leu Thr Ser Glu Ile
1               5                   10                  15
Asp Leu Pro Val Lys Arg Arg Ala
            20

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 13

Met Thr Pro Arg Gly Phe Ser Cys Leu Leu Leu Pro Thr Ser Glu Thr
1               5                   10                  15

Asp Leu Pro Val Lys Arg Arg Xaa
            20

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: misc_feature
<222> LOCATION: (23)..(24)
<223> OTHER INFORMATION: Xaa can be any naturally occurring amino acid

<400> SEQUENCE: 14

Met Ala Pro Arg Gly Phe Ser Cys Leu Leu Leu Ser Thr Ser Glu Ile
1               5                   10                  15

Asp Leu Pro Val Lys Arg Xaa Xaa
            20

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 15

Met Ala Pro Arg Gly Phe Ser Cys Leu Leu Leu Ser Thr Ser Glu Ile
1               5                   10                  15

Asp Leu Pro Val Lys Arg Arg Ala
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 16

Met Cys His Trp Ala Gly Gly Ala Ser Asn Thr Gly Asp Ala Arg Gly
1               5                   10                  15

Asp Val Phe Gly Lys Gln Ala Gly
            20

<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 17

Met Gly Val Lys Phe Phe Thr Leu Ser Thr Arg Phe Phe Pro Ser Val
1               5                   10                  15

Gln Arg Ala Val Pro Leu Trp Thr Asn Ser
            20                  25

<210> SEQ ID NO 18
<211> LENGTH: 38
<212> TYPE: PRT

<213> ORGANISM: Artificial Sequence
<220> FEATURE:
<223> OTHER INFORMATION: Description of Artificial Sequence: Humanin
      Polypeptide

<400> SEQUENCE: 18

Met Leu Gly Tyr Asn Phe Ser Ser Phe Pro Cys Gly Thr Ile Ser Ile
1               5                   10                  15

Ala Pro Gly Phe Asn Phe Tyr Arg Leu Tyr Phe Thr Trp Val Asn Gly
            20                  25                  30

Leu Ala Lys Val Val Trp
        35

<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 19

Met Leu Glu Val Met Phe Leu Val Asn Arg Arg Gly Lys Ile Cys Arg
1               5                   10                  15

Val Pro Phe Thr Phe Phe Asn Leu Ser Leu
            20                  25

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 20

Met Tyr Cys Ser Glu Val Gly Phe Cys Ser Glu Val Ala Pro Thr Glu
1               5                   10                  15

Ile Phe Asn Ala Gly Leu Val Val
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 21

Met Leu Asp Gln Asp Ile Pro Met Val Gln Pro Leu Ile Lys Val Arg
1               5                   10                  15

Leu Phe Asn Asp
            20

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 22

Met Ala Pro Arg Gly Ala Ser Cys Leu Leu Leu Leu Thr Ser Glu Ile

```
Asp Leu Pro Val Lys Arg Arg Ala
            20

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 23

Met Ala Pro Arg Gly Ala Ser Cys Leu Leu Leu Thr Gly Glu Ile
1               5                   10                  15

Asp Leu Pro Val Lys Arg Arg Ala
            20

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 24

Met Ala Pro Arg Gly Phe Ala Cys Leu Leu Leu Thr Ser Glu Ile
1               5                   10                  15

Asp Leu Pro Val Lys Arg Arg Ala
            20

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 25

Met Ala Pro Arg Gly Phe Ser Pro Leu Leu Leu Thr Ser Glu Ile
1               5                   10                  15

Asp Leu Pro Val Lys Arg Arg Ala
            20

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is P-Serine

<400> SEQUENCE: 26

Met Ala Pro Arg Gly Phe Ser Cys Leu Leu Leu Thr Xaa Glu Ile
1               5                   10                  15

Asp Leu Pro Val Lys Arg Arg Ala
            20

<210> SEQ ID NO 27
```

```
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is P-Serine

<400> SEQUENCE: 27

Met Ala Pro Arg Gly Phe Xaa Cys Leu Leu Leu Leu Thr Ser Glu Ile
1               5                   10                  15

Asp Leu Pro Val Lys Arg Arg Ala
            20

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is P-Serine
<220> FEATURE:
<221> NAME/KEY: SITE
<222> LOCATION: (14)..(14)
<223> OTHER INFORMATION: Xaa is P-Serine

<400> SEQUENCE: 28

Met Ala Pro Arg Gly Phe Xaa Cys Leu Leu Leu Leu Thr Xaa Glu Ile
1               5                   10                  15

Asp Leu Pro Val Lys Arg Arg Ala
            20

<210> SEQ ID NO 29
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is D-Serine

<400> SEQUENCE: 29

Met Ala Pro Arg Gly Phe Ser Cys Leu Leu Leu Leu Thr Xaa Glu Ile
1               5                   10                  15

Asp Leu Pro Val Lys Arg Arg Ala
            20

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is D-Serine

<400> SEQUENCE: 30
```

Met Ala Pro Arg Gly Phe Xaa Cys Leu Leu Leu Leu Thr Ser Glu Ile
1               5                   10                  15

Asp Leu Pro Val Lys Arg Arg Ala
            20

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is D-Serine
<220> FEATURE:
<221> NAME/KEY: SITE
<222> LOCATION: (14)..(14)
<223> OTHER INFORMATION: Xaa is D-Serine

<400> SEQUENCE: 31

Met Ala Pro Arg Gly Phe Xaa Cys Leu Leu Leu Leu Thr Xaa Glu Ile
1               5                   10                  15

Asp Leu Pro Val Lys Arg Arg Ala
            20

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is D-Serine

<400> SEQUENCE: 32

Met Ala Pro Ala Gly Ala Ser Cys Leu Leu Leu Leu Thr Xaa Glu Ile
1               5                   10                  15

Asp Leu Pro Val Lys Arg Arg Ala
            20

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (12)..(12)
<223> OTHER INFORMATION: Xaa is D-Serine

<400> SEQUENCE: 33

Pro Ala Gly Ala Ser Cys Leu Leu Leu Leu Thr Xaa Glu Ile Asp Leu
1               5                   10                  15

Pro

<210> SEQ ID NO 34
<211> LENGTH: 32
<212> TYPE: PRT
<213> ORGANISM: Artificial Sequence
<220> FEATURE:

<223> OTHER INFORMATION: Description of Artificial Sequence: Humanin
     Polypeptide

<400> SEQUENCE: 34

Glu Phe Leu Ile Val Ile Lys Ser Met Ala Pro Arg Gly Phe Ala Cys
1               5                   10                  15

Leu Leu Leu Leu Thr Ser Glu Ile Asp Leu Pro Val Lys Arg Arg Ala
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Humanin
     Polypeptide

<400> SEQUENCE: 35

Glu Phe Leu Ile Val Ile Lys Ser Met Ala Pro Arg Gly Phe Ser Cys
1               5                   10                  15

Leu Leu Leu Leu Thr Gly Glu Ile Asp Leu Pro Val Lys Lys Lys Lys
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Humanin
     Polypeptide

<400> SEQUENCE: 36

Glu Phe Leu Ile Val Ile Lys Ser Met Ala Pro Arg Gly Phe Ser Cys
1               5                   10                  15

Leu Leu Leu Leu Thr Ser Glu Ile Asp Leu Pro Val Lys Arg Arg Ala
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Humanin
     Polypeptide

<400> SEQUENCE: 37

Glu Phe Leu Ile Val Ile Lys Ser Met Ala Pro Arg Gly Phe Ser Ala
1               5                   10                  15

Leu Leu Leu Leu Thr Ser Glu Ile Asp Leu Pro Val Lys Arg Arg Ala
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Humanin
     Polypeptide

<400> SEQUENCE: 38

Glu Phe Leu Ile Val Ile Lys Ser Met Ala Pro Arg Gly Phe Ser Cys
1               5                   10                  15

Leu Leu Leu Leu Thr Gly Glu Ile Asp Leu Pro Val Lys Arg Arg Ala
            20                  25                  30

```
<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 39

Glu Phe Leu Ile Val Ile Lys Ser Met Ala Pro Ala Gly Ala Ser Cys
1               5                   10                  15

Leu Leu Leu Leu Thr Gly Glu Ile Asp Leu Pro Val Lys Arg Arg Ala
            20                  25                  30

<210> SEQ ID NO 40
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 40

Met Ala Pro Arg Gly Phe Ser Cys Leu Leu Leu Leu Thr Ser Glu Ile
1               5                   10                  15

Asp Leu Pro Val Lys Arg Arg Ala
            20

<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 41

Met Ala Pro Arg Gly Phe Ser Cys Leu Leu Leu Leu Thr Gly Glu Ile
1               5                   10                  15

Asp Leu Pro Val Lys Arg Arg Ala
            20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 42

Met Ala Pro Arg Gly Phe Ser Ala Leu Leu Leu Leu Thr Ser Glu Ile
1               5                   10                  15

Asp Leu Pro Val Lys Arg Arg Ala
            20

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
```

<223> OTHER INFORMATION: Xaa is P-Serine

<400> SEQUENCE: 43

Met Ala Pro Arg Gly Phe Ser Cys Leu Leu Leu Thr Xaa Glu Ile
1               5                   10                  15

Asp Leu Pro Val Lys Arg Arg Ala
            20

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is P-Serine

<400> SEQUENCE: 44

Met Ala Pro Arg Gly Phe Xaa Cys Leu Leu Leu Thr Ser Glu Ile
1               5                   10                  15

Asp Leu Pro Val Lys Arg Arg Ala
            20

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is P-Serine
<220> FEATURE:
<221> NAME/KEY: SITE
<222> LOCATION: (14)..(14)
<223> OTHER INFORMATION: Xaa is P-Serine

<400> SEQUENCE: 45

Met Ala Pro Arg Gly Phe Xaa Cys Leu Leu Leu Thr Xaa Glu Ile
1               5                   10                  15

Asp Leu Pro Val Lys Arg Arg Ala
            20

<210> SEQ ID NO 46
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is D-Serine

<400> SEQUENCE: 46

Met Ala Pro Arg Gly Phe Ser Cys Leu Leu Leu Thr Xaa Glu Ile
1               5                   10                  15

Asp Leu Pro Val Lys Arg Arg Ala
            20

<210> SEQ ID NO 47

```
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is D-Serine

<400> SEQUENCE: 47

Met Ala Pro Arg Gly Phe Xaa Cys Leu Leu Leu Leu Thr Ser Glu Ile
1               5                   10                  15

Asp Leu Pro Val Lys Arg Arg Ala
            20

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (7)..(7)
<223> OTHER INFORMATION: Xaa is D-Serine
<220> FEATURE:
<221> NAME/KEY: SITE
<222> LOCATION: (14)..(14)
<223> OTHER INFORMATION: Xaa is D-Serine

<400> SEQUENCE: 48

Met Ala Pro Arg Gly Phe Xaa Cys Leu Leu Leu Leu Thr Xaa Glu Ile
1               5                   10                  15

Asp Pro Pro Val Lys Arg Arg Ala
            20

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (14)..(14)
<223> OTHER INFORMATION: Xaa is D-Serine

<400> SEQUENCE: 49

Met Ala Pro Ala Gly Ala Ser Cys Leu Leu Leu Leu Thr Xaa Glu Ile
1               5                   10                  15

Asp Leu Pro Val Lys Arg Arg Ala
            20

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide
<220> FEATURE:
<221> NAME/KEY: SITE
<222> LOCATION: (12)..(12)
<223> OTHER INFORMATION: Xaa is D-Serine

<400> SEQUENCE: 50
```

```
Pro Ala Gly Ala Ser Cys Leu Leu Leu Leu Thr Xaa Glu Ile Asp Leu
1               5                   10                  15

Pro
```

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 51

```
Met Ala Pro Arg Gly Phe Ala Cys Leu Leu Leu Thr Ser Glu Ile
1               5                   10                  15

Asp Leu Pro Val Lys Arg Arg Ala
            20
```

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 52

```
Pro Arg Gly Phe Ala Cys Leu Leu Leu Leu Thr Ser Glu Ile Asp Leu
1               5                   10                  15

Pro
```

<210> SEQ ID NO 53
<211> LENGTH: 25
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 53

```
Tyr Met Ala Pro Arg Gly Phe Ser Cys Leu Leu Leu Leu Thr Gly Glu
1               5                   10                  15

Ile Asp Leu Pro Val Lys Lys Lys Lys
            20                  25
```

<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 54

```
Glu Phe Leu Ile Val Ile Lys Ser Met Ala Pro Arg Gly Phe Ala Cys
1               5                   10                  15

Leu Leu Leu Leu Thr Ser Glu Ile Asp Leu Pro Val Lys Arg Arg Ala
            20                  25                  30
```

<210> SEQ ID NO 55
<211> LENGTH: 32
<212> TYPE: PRT
<213> ORGANISM: Artificial Sequence
<220> FEATURE:

```
<223> OTHER INFORMATION: Description of Artificial Sequence: Humanin
      Polypeptide

<400> SEQUENCE: 55

Glu Phe Leu Ile Val Ile Lys Ser Met Ala Pro Arg Gly Phe Ser Cys
1               5                   10                  15
Leu Leu Leu Leu Thr Gly Glu Ile Asp Leu Pro Val Lys Lys Lys Lys
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 56

Glu Phe Leu Ile Val Ile Lys Ser Met Ala Pro Arg Gly Phe Ser Cys
1               5                   10                  15
Leu Leu Leu Leu Thr Ser Glu Ile Asp Leu Pro Val Lys Arg Arg Ala
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 57

Glu Phe Leu Ile Val Ile Lys Ser Met Ala Pro Arg Gly Phe Ser Ala
1               5                   10                  15
Leu Leu Leu Leu Thr Ser Glu Ile Asp Leu Pro Val Lys Arg Arg Ala
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 58

Glu Phe Leu Ile Val Ile Lys Ser Met Ala Pro Arg Gly Phe Ser Cys
1               5                   10                  15
Leu Leu Leu Leu Thr Gly Glu Ile Asp Leu Pro Val Lys Arg Arg Ala
            20                  25                  30

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 59

Glu Phe Leu Ile Val Ile Lys Ser
1               5

<210> SEQ ID NO 60
<211> LENGTH: 24
```

```
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 60

Met Ala Pro Ala Gly Ala Ser Cys Leu Leu Leu Leu Thr Gly Glu Ile
1               5                   10                  15

Asp Leu Pro Val Lys Arg Arg Ala
            20

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 61

Glu Phe Leu Ile Val Ile Lys Ser Met Ala Pro Ala Gly Ala Ser Cys
1               5                   10                  15

Leu Leu Leu Leu Thr Gly Glu Ile Asp Leu Pro Val Lys Arg Arg Ala
            20                  25                  30

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Humanin
      Polypeptide

<400> SEQUENCE: 62

Pro Arg Gly Phe Ser Cys Leu Leu Leu Leu Thr Gly Glu Ile Asp Leu
1               5                   10                  15

Pro
```